(12) United States Patent
Huang et al.

(10) Patent No.: US 11,946,002 B2
(45) Date of Patent: Apr. 2, 2024

(54) METHOD AND DEVICE FOR TREATING OIL GAS

(71) Applicants: SINOPEC ENGINEERING INCORPORATION, Beijing (CN); SINOPEC ENGINEERING (GROUP) CO., LTD., Beijing (CN)

(72) Inventors: Mengqi Huang, Beijing (CN); Longhong Yu, Beijing (CN); Lei Wu, Beijing (CN); Shengyang Jiang, Beijing (CN); Yuwen Ding, Beijing (CN); Na Gao, Beijing (CN); Di Wu, Beijing (CN); Dan Duan, Beijing (CN)

(73) Assignees: SINOPEC ENGINEERING INCORPORATION, Beijing (CN); SINOPEC ENGINEERING (GROUP) CO., LTD., Beijing (CN)

( * ) Notice: Subject to any disclaimer, the term of this patent is extended or adjusted under 35 U.S.C. 154(b) by 0 days.

(21) Appl. No.: 17/281,980

(22) PCT Filed: Jun. 5, 2020

(86) PCT No.: PCT/CN2020/094728
§ 371 (c)(1),
(2) Date: Apr. 1, 2021

(87) PCT Pub. No.: WO2020/244639
PCT Pub. Date: Dec. 10, 2020

(65) Prior Publication Data
US 2021/0371760 A1    Dec. 2, 2021

(30) Foreign Application Priority Data

| Jun. 6, 2019 | (CN) | 201910492804.0 |
| Jun. 28, 2019 | (CN) | 201910575665.8 |
| Aug. 12, 2019 | (CN) | 201910740666.3 |

(51) Int. Cl.
  *C10G 53/08* (2006.01)
  *B01D 53/14* (2006.01)
  *C10G 53/02* (2006.01)

(52) U.S. Cl.
  CPC ......... *C10G 53/08* (2013.01); *B01D 53/1406* (2013.01); *B01D 53/1425* (2013.01);
  (Continued)

(58) Field of Classification Search
None
See application file for complete search history.

(56) References Cited

U.S. PATENT DOCUMENTS 3,339,342 A * 9/1967 Blaker ................. B01D 53/526
                                                      95/236
3,738,086 A * 6/1973 Bellisio ............. B01D 53/1418
                                                      95/180

(Continued)

FOREIGN PATENT DOCUMENTS

| CN | 105503492 A | 4/2016 |
| CN | 107433107 A * | 12/2017 |

OTHER PUBLICATIONS

International search report of PCT Patent Application No. PCT/CN2020/094728 dated Aug. 27, 2020.

*Primary Examiner* — Tam M Nguyen

(57) ABSTRACT

Provided is a method for treating an oil gas, which can realize high-efficiency separation for and recovery of gasoline components, $C_2$, $C_3$, and $C_4$ components. The method first conducts separation of light hydrocarbon components from gasoline components, and then performs subsequent treatment on a stream rich in the light hydrocarbon components, during which it is no longer necessary to use gasoline to circularly absorb liquefied gas components, which significantly reduces the amount of gasoline to be circulated and reduces energy consumption throughout the separation (Continued)

process. Besides, in this method, impurities, such as $H_2S$ and mercaptans, in the stream rich in the light hydrocarbon components are removed first before the separation for the components. This ensures that impurities will not be carried to a downstream light hydrocarbon recovery section, thus avoiding corrosion issues caused by hydrogen sulfide in the light hydrocarbon recovery section.

13 Claims, 11 Drawing Sheets

(52) U.S. Cl.
CPC .......... *B01D 2252/205* (2013.01); *C10G 2300/1037* (2013.01); *C10G 2300/202* (2013.01); *C10G 2300/207* (2013.01)

(56) References Cited

U.S. PATENT DOCUMENTS

| | | | | |
|---|---|---|---|---|
| 4,167,402 | A * | 9/1979 | Davis | F25J 3/0233 |
| | | | | 62/935 |
| 5,019,143 | A * | 5/1991 | Mehrta | C01B 3/52 |
| | | | | 62/635 |
| 5,220,097 | A * | 6/1993 | Lam | C10G 5/04 |
| | | | | 585/259 |
| 7,273,542 | B2 * | 9/2007 | Duhon | C10G 70/06 |
| | | | | 585/271 |
| 10,365,038 | B2 * | 7/2019 | Schwint | C07C 7/005 |
| 10,894,929 | B1 * | 1/2021 | Mohammad | F25J 3/0233 |
| 11,198,661 | B2 * | 12/2021 | Reyneke | C07C 7/09 |
| 2018/0318750 | A1 * | 11/2018 | Zhong | C10K 1/002 |

* cited by examiner

METHOD AND DEVICE FOR TREATING OIL GAS

CROSS-REFERENCE TO RELATED APPLICATIONS

The present application claims priorities of Chinese patent application No. 201910492804.0 entitled "Device and method for high-pressure desulfurization and separation of oil gas" and filed on Jun. 6, 2019, Chinese patent application No. 201910575665.8 entitled "Method and device for treatment of oil gas" and filed on Jun. 28, 2019, and Chinese patent application No. 201910740666.3 entitled "Method and device for recovery of oil gas" and filed on Aug. 12, 2019, the entire contents of which are incorporated herein by reference.

FIELD OF INVENTION

The present invention relates to the field of oil refining and chemical engineering, in particular to a method and a device for treating an oil gas.

BACKGROUND OF INVENTION

Light hydrocarbons refer to components such as methane, ethane, ethylene, propane, propylene, $C_4$, etc. obtained in a petrochemical process. Processes for separation of light hydrocarbons have always been the focus in petrochemical processes. Processes for separation between $C_2$, $C_3$, and $C_4$ are now relatively mature, and such separation usually adopts a rectification method. Methane has a low boiling point, and therefore separation of methane from $C_2$ by a rectification method requires that methane and $C_2$ be cooled to a temperature of $-100°$ C. or lower, which is, in other words, cryogenic separation. Cryogenic separation is usually used in an ethylene unit, and it requires large investment and can lead to huge consumption. For this reason, separation for methane has always been the focus in processes for separation of light hydrocarbons, and the development of processes and technologies for separation of light hydrocarbons and the design of process flows thereof are all based around the separation for methane.

Existing fluid catalytic cracking processes usually recover liquefied gas ($C_3/C_4$) components and realizes separation of the liquefied gas components from dry gas ($H_2/C_1/C_2$) components by way of absorption and stabilization. The fluid catalytic cracking process has a high yield of dry gases. The dry gases have a content of $C_2$ component of up to 25-40 wt %, which is mainly ethylene and ethane. Among them, ethylene can be used for producing polyethylene, styrene, etc., and ethane can be used for producing ethylene by cracking. Cyclic cracking of ethane can result in a yield of ethylene of up to 80% as well as a high yield of hydrogen. Therefore, it is of great interest to recover $C_2$ resources in the dry gases. Generally, a recovered $C_2$ resource can be sent to a separation unit of an ethylene unit to produce ethylene and ethane, and can also be sent to a downstream device for producing ethylbenzene/styrene. The existing technologies focus on recovering $C_2$ from the dry gas by way of absorption, and they have the following defects.

(1) The dry gas and the $C_4$ component have to be separated twice. Specifically, during the absorption and the stabilization, the dry gas and the liquefied gas components are separated, but during recovery of $C_2$, $C_4$ is used to absorb $C_2$, in which way, $C_4$ and the dry gas are mixed again, and have to be separated again.

(2) An absorption and stabilization system uses stable gasoline as an absorbent to recover the liquefied gas components. The fluid catalytic cracking process has a high yield of the liquefied gas components, and gasoline circulates between a gasoline absorption column, a dethanizer, and a stabilizer, which requires a large amount of gasoline to be circulated. In addition, the dethanizer and the stabilizer have a high temperature level at bottoms thereof and thermal loads of reboilers at the bottoms of the dethanizer and the stabilizer are relatively large, which can lead to huge energy consumption.

(3) The entire process is relatively long, which increases the investment and energy consumption. In order to recover light hydrocarbon components such as $C_2/C_3/C_4$ and so on from the fluid catalytic cracking process, simplify the separation procedure, and reduce the investment and energy consumption, the present invention is provided.

(4) When a recovered $C_2$ product is sent to the separation unit of the ethylene unit, components such as part of propylene and the like carried in the $C_2$ product can be recovered through the separation unit of the ethylene unit. However, when the recovered $C_2$ product is sent downstream for production of ethylbenzene, the propylene component contained therein can bring many adverse effects to the production of ethylbenzene, which not only greatly increases consumption of benzene, but also directly affects quality of ethylbenzene and styrene products. Because the boiling point of the $C_2$ component is low, the separation of the $C_2$ component from the $C_3$ component usually needs a temperature of from $-5$ to $-20°$ C., which requires dehydration and removal of $CO_2$ as well as a refrigerant of a lower temperature level, leading to increased investment and energy consumption.

(5) In the existing process, after the absorption and stabilization, the dry gas and the liquefied gases are subjected to desulfurization and sweetening, during which $H_2S$ and mercaptans circulate in the entire absorption and stabilization system, which can lead to corrosion problems, and may also lead safety problems in the entire absorption and stabilization system possibly caused by $H_2S$ leakage.

SUMMARY OF INVENTION

In view of the above-mentioned problems in the existing technologies, a first objective of the present invention is to provide a method for treating an oil gas which is simple in its process flow and operated at moderate conditions and can be used to realize high-efficiency separation for and recovery of a gasoline component, a $C_2$ component, a $C_3$ component, and a $C_4$ component.

A second objective of the present invention is to provide a device for treating an oil gas corresponding to the above first objective.

In order to realize the first objective, the present invention provides the following technical solutions.

A method for treating an oil gas, comprising the following steps:

(1) subjecting a hydrocarbon material to a first gas-liquid separation to obtain a first gas-phase material mainly containing $H_2$ and $C_1$-$C_4$ and a first liquid-phase material mainly containing $C_{5+}$; and (2) separating the first gas-phase material to obtain a dry gas product mainly containing $H_2$ and $C_1$, a $C_2$ product mainly containing $C_2$, a $C_3$ product mainly containing $C_3$, and a $C_4$ product mainly containing $C_4$.

In order to realize the second objective, the present invention provides the following technical solutions.

A system for treating an oil gas, comprising, connected in sequence, a light hydrocarbon extraction unit for extracting a first gas-phase material mainly containing $H_2$ and $C_1$-$C_4$, and a separation unit for separating the first gas-phase material to obtain a dry gas product mainly containing $H_2$ and $C_1$, a $C_2$ product mainly containing $C_2$, a $C_3$ product mainly containing $C_3$, and a $C_4$ product mainly containing $C_4$.

The present invention has the following beneficial effects.

(1) The present invention separates $C_4$ and $C_{4-}$ components from gasoline components without using gasoline to circularly absorb liquefied gas components, which greatly reduces the amount of the gasoline to be circulated and reduces the energy consumption of the whole separation process.

(2) The present invention is simple in its process flow and operated at moderate conditions, consumes less energy, and can realize the separation for and recovery of gasoline and light hydrocarbons in an oil-gas mixture by using fewer devices, and can, in particular, realize high-efficiency separation and recovery of $C_2$, $C_3$ and $C_4$ components. A second separation between the $C_2$ component and the various other components is not needed. Meanwhile, the present invention can ensure a total recovery rate of the $C_2$ component of more than 98 wt %, a recovery rate of a propylene component of more than 99 wt %, a content of methane in the recovered $C_2$ component of not more than 1 vol %, and a content of ethane in the recovered $C_3$ component of not more than 200 ppmv.

(3) The deethanizer in the present invention uses propane or a mixed $C_4$ absorbent in the separation for the $C_2$ component. The $C_2$ component separated out basically contains no propylene, and can be directly sent to a downstream device for preparation of ethylbenzene/styrene. The propane or mixed $C_4$ absorbent is available in the system, and does not need to be introduced from the outside of the system, which saves energy consumption.

(4) The present invention realizes the high-efficiency recovery of $C_2$ and propylene components and the like under a subcooled condition. The recovered $C_2$ product basically contains no propylene, and can be directly sent downstream for preparation of ethylbenzene/styrene, which can reduce energy consumption during the downstream preparation of ethylbenzene/styrene, reduce benzene consumption, and ensure the quality of ethylbenzene and styrene products. Meanwhile, under the subcooled condition, dehydration and removal of impurities such as $CO_2$ and the like are not needed, and a refrigerant of a lower temperature level is not needed either, which further decreases investment and consumption.

(5) In the present invention, the recovered $C_3$ component is further separated into propylene and propane. The recovery rates of propylene and propane can both be more than 99 wt %. The purity of the propylene product is not less than 99.6 v %, and can be used as polymer-grade propylene without being further treated.

(6) In the present invention, the dry gas collected from the top of the absorbent recovery column is mainly methane and hydrogen, and contains relatively small amounts of impurities and a content of $C_2$ and $C_{2+}$ components of not more than 2 vol %. The dry gas has a pressure of 2.1-2.7 MPaG, and a purity of more than 40-70 mol %. The hydrogen resource in the dray gas can be directly recovered by a pressure swing adsorption method.

(7) The present invention can desulfurize and sweeten the gas phase and the liquid phase, respectively. Because the gas phase is desulfurized at a higher pressure, it requires a device of a relatively small volume, which needs less investment and can achieve better desulfurization effects. Meanwhile, as a content of heavy hydrocarbons in the gas phase is reduced, heavy hydrocarbons can be prevented from being condensed into the amine solution, which effectively avoids foam entrainment in a desulfurization device caused by amine solution foaming, and thus ensures stable operation of the device.

(8) In the present invention, hydrogen sulfide and mercaptans are removed before entering the absorption column and cannot be brought to a downstream light hydrocarbon recovery section, which avoids corrosion related problems in the light hydrocarbon recovery section caused by hydrogen sulfide, greatly reduces the concentration of hydrogen sulfide in the downstream section, and thus improves safety. To separate hydrogen sulfide and carbon dioxide out in advance can decrease load and energy consumption of a downstream light hydrocarbon recovery system, and improve the quality of a downstream product due to the removal of $CO_2$.

BRIEF DESCRIPTION OF THE DRAWINGS

The above and other objectives, features and advantages of the present invention will become more apparent by describing exemplary embodiments of the present invention in detail with reference to the accompanying drawings. In the exemplary embodiments of the present invention, same reference numerals generally represent same components.

DESCRIPTION OF REFERENCE NUMERALS

Figure 1:
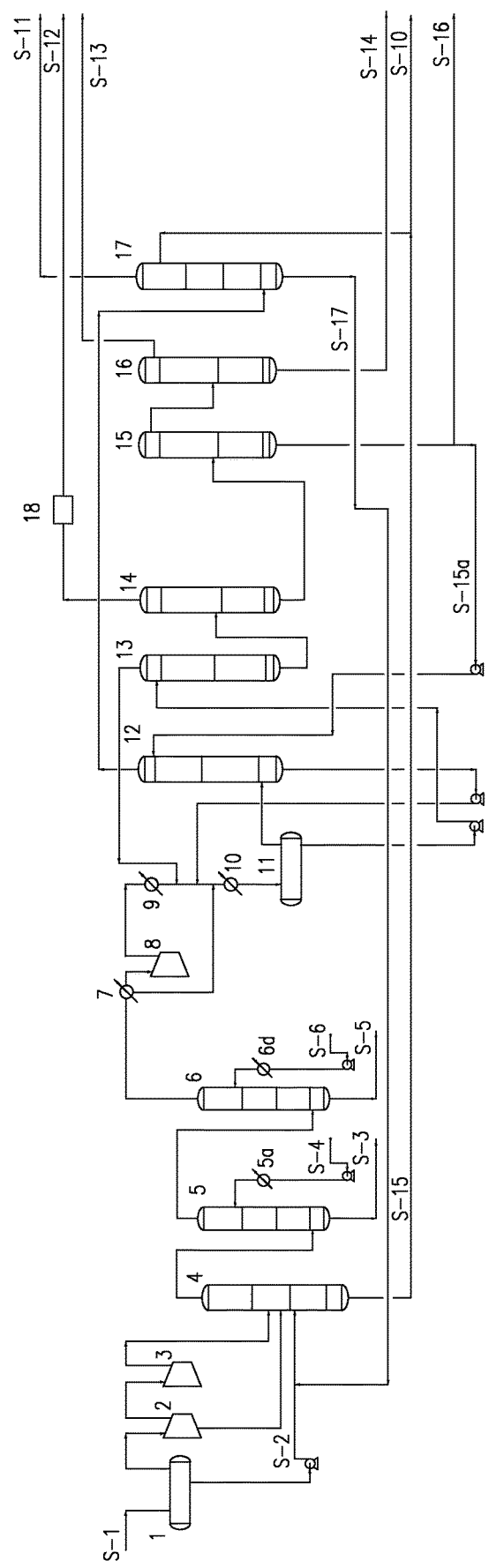
FIG. 1 is a flow diagram of a process according to Example 1 of the present invention.

1: gas-liquid separation tank I; 2: compressor I; 3: compressor II; 4: debutanizer; 4a: light-heavy gasoline separation column; 4b: light hydrocarbon-light gasoline separation column; 5: rich gas desulfurizing column; 5a: liquid hydrocarbon desulfurizing column; 5b: lean amine solution circulating pump; 5c: solvent regeneration column; 5d: lean amine solution cooling unit; 6: rich gas sweetening column; 6a: liquid hydrocarbon sweetening reactor; 6b: rich gas water washing circulating pump; 6c: water washing used water heating unit; 6d: alkali liquor cooling unit; 6e: rich gas water washing tank; 7: cooling unit I; 7a: gas-liquid separation tank II; 8: compressor III; 9: cooling unit II; 10: cooling unit III; 11: feeding tank; 12: absorption column; 13: demethanizer; 14: deethanizer; 15: depropanizer; 16: propylene rectifying column; 17: absorbent recovery column; 18: impurity treatment unit; 19: drying unit; 20: cooling unit IV;

S-1: oil gas from an upstream device; S-2: crude gasoline; S-3: rich amine solution; S-4: lean amine solution; S-5: alkali liquor to be regenerated; S-6: alkali liquor; S-7: water washing used water discharge; S-8: alkaline gas; S-9: impurity-removed rich gas; S-9a: impurity-removed liquid hydrocarbon; S-10: stable gasoline product; S-10a: light gasoline product; S-10b: heavy gasoline product; S-11: dry gas; S-12: mixed $C_2$ product; S-13: propylene product; S-14: propane product; S-14a: circulated propane; S-15: stable gasoline absorbent; S-15a: $C_4$ absorbent; S-15b: circulated $C_4$; S-16: mixed $C_4$ product; S-17: rich gas absorbing gasoline.

DETAILED DESCRIPTION OF THE EMBODIMENTS

Embodiments of the present invention will be described in detail below with reference to examples. Those skilled in the art however should appreciate that the following examples are only illustrative of the present invention and should not be construed as limiting the scope of the present invention.

In order to realize the first objective above, the present invention adopts the following technical solutions.

A method for treating an oil gas comprising the following steps:

(1) subjecting a hydrocarbon material to a first gas-liquid separation to obtain a first gas-phase material mainly containing $H_2$ and $C_1$-$C_4$ and a first liquid-phase material mainly containing $C_{5+}$;

(2) separating the first gas-phase material to obtain a dry gas product mainly containing $H_2$ and $C_1$, a $C_2$ product mainly containing $C_2$, a $C_3$ product mainly containing $C_3$, and a $C_4$ product mainly containing $C_4$.

The inventors of the present invention found through research that to first realize separation of light hydrocarbon components from gasoline components so as to obtain a stream rich in the light hydrocarbon components, and then to carry out subsequent treatment on the stream rich in the light hydrocarbon components renders it unnecessary to use gasoline to circularly absorb liquefied gas components, which significantly reduces an amount of gasoline to be circulated and thus decreases energy consumption of the entire separation process.

According to the present invention, at least part of the first liquid-phase material rich in $C_{5+}$ is collected as a stabilized gasoline product.

According to the present invention, in the context of the present application, the gas-phase material is compressed and then enters a downstream step; and/or the liquid-phase material is pressurized and then enters a downstream step. A compression treatment of the gas-phase material can be one-stage or multi-stage compression.

In some preferred embodiments of the present invention, the separation in step (2) is performed after the first gas-liquid separation is subjected to impurity removal in step (2). Preferably, the impurity removal is used to remove an acidic substance and a mercaptan. The acidic substance is specifically hydrogen sulfide and/or carbon dioxide.

The inventors of this application also found through research that before carrying out the separation for the components, to remove impurities such as $H_2S$, $CO_2$ and mercaptans in the stream rich in light hydrocarbon components ensures that the impurities will not be brought to a downstream light hydrocarbon recovery section, which can simplify setting of an impurity removal device in the entire process, avoid relevant corrosion problems in the light hydrocarbon recovery section caused by hydrogen sulfide, enhance safety due to enormously decreased concentration of hydrogen sulfide in the downstream section, and can guarantee quality of a downstream product.

In some preferred embodiments of the present invention, in step (2), the first gas-phase material is subjected to impurity removal to obtain an impurity-removed first gas-phase material, and then the impurity-removed first gas-phase material is subjected to separation to obtain the dry gas product, the $C_2$ product, the $C_3$ product, and the $C_4$ product.

In some preferred embodiments of the present invention, the impurity removal includes sequentially subjecting the first gas-phase material to amine washing and/or alkali washing and/or water washing. Preferably, the amine washing is operated conditions including: a temperature of 35-50° C., and a pressure of 1.0-1.5 MPaG.

In some preferred embodiments of the present invention, the alkali washing is operated conditions including: a temperature of 35-50° C., and a pressure of 0.9-1.4 MPaG.

In some preferred embodiments of the present invention, the water washing is operated conditions including: a temperature of 35-50° C., and a pressure of 0.9-1.4 MPaG.

In some preferred embodiments of the present invention, in step (2), the first gas-phase material is subjected to a second gas-liquid separation to obtain a second gas-phase material mainly containing $H_2$ and $C_1$-$C_4$ and a second liquid-phase material mainly containing $H_2$ and $C_1$-$C_4$. The second gas-phase material is then subjected to gas phase impurity removal to obtain an impurity-removed second gas-phase material, and the second liquid-phase material is subjected to liquid phase impurity removal to obtain an impurity-removed second liquid-phase material. The impurity-removed second gas-phase material and the impurity-removed second liquid-phase material are mixed and then subjected to separation to obtain the dry gas product, the $C_2$ product, the $C_3$ product, and the $C_4$ product.

Preferably, the gas phase impurity removal includes sequentially subjecting the second gas-phase material to gas phase amine washing and/or gas phase alkali washing and/or gas phase water washing, and the liquid phase impurity removal includes sequentially subjecting the second liquid-phase material to liquid phase amine washing and/or liquid phase alkali washing and/or liquid phase water washing.

In some preferred embodiments of the present invention, the gas phase amine washing is operated at conditions including: a temperature of 35-50° C., and a pressure of 2.2-3.0 MPaG.

In some preferred embodiments of the present invention, the gas phase alkali washing is operated at conditions including: a temperature of 35-50° C., and a pressure of 2.2-2.9 MPaG.

In some preferred embodiments of the present invention, the gas phase water washing is operated at conditions including: a temperature of 35-50° C., and a pressure of 2.2-2.9 MPaG.

In some preferred embodiments of the present invention, the liquid phase amine washing is operated at conditions including: a temperature of 35-50° C., and a pressure of 3.0-3.5 MPaG.

In some preferred embodiments of the present invention, the liquid phase alkali washing is operated at conditions including: a temperature of 35-50° C., and a pressure of 3.0-3.5 MPaG.

In some preferred embodiments of the present invention, the liquid phase water washing is operated at conditions including: a temperature of 35-50° C., and a pressure of 3.0-3.5 MPaG.

In some preferred embodiments of the present invention, in step (2), the separation specifically includes the following steps:
(a) cooling the impurity-removed first gas-phase material or the mixture material of the impurity-removed second gas-phase material and the impurity-removed second liquid-phase material, and then subjecting the cooled impurity-removed first gas-phase material or the cooled mixture material of the impurity-removed second gas-phase material and the impurity-removed second liquid-phase material to the first separation, to obtain a gas-phase material mainly containing $H_2$ and $C_1$ and a liquid-phase material mainly containing $C_1$-$C_4$;
(b) subjecting the liquid-phase material mainly containing $C_1$-$C_4$ to a second separation to obtain a gas-phase material mainly containing $C_1$ and a liquid-phase material mainly containing $C_2$-$C_4$;
(c) subjecting the liquid-phase material mainly containing $C_2$-$C_4$ to a third separation to obtain the $C_2$ product mainly containing $C_2$ and a liquid-phase material mainly containing $C_3$-$C_4$ or obtain the $C_3$ product mainly containing $C_3$ and a liquid-phase material mainly containing $C_2$ and $C_4$; and
(d) subjecting the liquid-phase material mainly containing $C_3$-$C_4$ or the liquid-phase material mainly containing $C_2$ and $C_4$ to a fourth separation to obtain the $C_4$ product mainly containing $C_4$ and the $C_3$ product mainly containing $C_3$ or the $C_2$ product mainly containing $C_2$.

In some preferred embodiments of the present invention, the separation further includes step (e) of subjecting the $C_3$ product to obtain a propane product mainly containing propane and a propylene product mainly containing propylene.

In some preferred embodiments of the present invention, in step (a), the gas-phase material mainly containing $H_2$ and $C_1$ is treated with an absorbent to obtain the dry gas product containing $H_2$ and $C_1$ and a liquid-phase material mainly containing the absorbent. Preferably, the absorbent is a mixture of $C_4$/C5. More preferably, the liquid-phase material mainly containing the absorbent is recycled to step (d).

According to the present invention, the first liquid-phase material mainly containing $C_{5+}$ obtained in step (1) also contains a mixture of $C_4$/C5, and therefore in the present invention, the first liquid-phase material mainly containing $C_{5+}$ can be partially or completely used as the absorbent.

In some preferred embodiments of the present invention, the gas-phase material mainly containing $C_1$ is recycled to step (a). Preferably, the cooling is conducted one or more times, and the gas-phase material mainly containing $C_1$ is recycled to a first cooling step.

In some preferred embodiments of the present invention, the hydrocarbon material is derived from a top of a fluid catalytic cracking fractionator, a top of a deep catalytic cracking fractionator, a top of a catalytic pyrolysis fractionator, or a top of a coking fractionator.

In some preferred embodiments of the present invention, the hydrocarbon material is a condensed and cooled material.

In some preferred embodiments of the present invention, the condensed and cooled material has a temperature of 30-60° C. and a pressure of 0.01-0.3 MPa G.

In some preferred embodiments of the present invention, in step (1), the first gas-liquid separation is selected from mode I and mode II. Mode I is to directly separate the hydrocarbon material into the first gas-phase material mainly containing $H_2$ and $C_1$-$C_4$ and the first liquid-phase material mainly containing $C_{5+}$. Mode II is to first separate the hydrocarbon material into a gas-phase material mainly containing $H_2$, light hydrocarbons and light gasoline, and a liquid-phase material mainly containing heavy gasoline, and then separate the gas-phase material mainly containing $H_2$, light hydrocarbons and light gasoline into the first gas-phase material mainly containing $H_2$ and $C_1$ to $C_4$ and the first liquid-phase material mainly containing $C_{5+}$.

According to the present invention, when the hydrocarbon material does not contain a heavy gasoline component, the first gas-liquid separation can be mode I, and when the hydrocarbon material contains a heavy gasoline component, the first gas-liquid separation is selected from mode I and mode II.

According to the present invention, the term "directly" referred in mode I means that compared with mode II, mode I does not include a step of removing heavy gasoline and is a way of directly obtaining, by separation, the first gas-phase material mainly containing $H_2$ and $C_1$-$C_4$ and the first liquid-phase material mainly containing $C_{5+}$.

According to the present invention, light hydrocarbons refer to all hydrocarbons of $C_1$-$C_4$, comprising all alkanes, alkenes, naphthenes, alkynes, and diolefins.

According to the present invention, light gasoline refers to fractions of $C_5$ to boiling point of 75° C. (ASTM D86).

According to the present invention, heavy gasoline refers to fractions having a boiling range (ASTM D86) from an initial boiling point of 75° C. to a final boiling point of 200° C.

In some preferred embodiments of the present invention, mode I is performed in a debutanizer, and mode II is performed in a light-heavy gasoline separation column and a light hydrocarbon-light gasoline separation column.

In some preferred embodiments of the present invention, the debutanizer has an operating temperature at a top thereof of 40-70° C., preferably 45-65° C., and more preferably 45-55° C., and/or an operating temperature at a bottom thereof of 180-220° C., preferably 150-200° C., and more preferably 150-200° C., and/or an internal operating pressure of 1.0-1.6 MPa G, preferably 1.0-1.5 MPa G; and/or, the light-heavy gasoline separation column has an operating temperature at a top thereof of 60-85° C., and/or an operating temperature at a bottom thereof of 140-190° C., and/or an internal operating pressure 0.25-0.5 MPaG; and/or, the light hydrocarbon-light gasoline separation column has an operating temperature of 55-90° C., preferably 55-80° C., more preferably 65-80° C., and/or an internal operating pressure of 1.0-1.35 MPaG.

In some preferred embodiments of the present invention, in step (a), the first separation is performed at conditions including: a temperature of 5-25° C., a pressure of 2.0-3.5 MPaG, preferably 2.2-2.9 MPaG, more preferably 2.2-2.8 MPaG, further preferably 2.4-2.8 MPaG. Preferably, the first separation is performed in a feeding tank.

In some preferred embodiments of the present invention, in step (b), the second separation is performed in a demethanizer. The demethanizer has a temperature at a top thereof of 10-40° C., a temperature at a bottom thereof of 70-95° C., and an internal pressure of 2.3-2.9 MPaG.

In some preferred embodiments of the present invention, in step (c), when it is intended to obtain the $C_2$ product mainly containing $C_2$ and the liquid-phase material mainly containing $C_3$-$C_4$, the third separation is performed in a deethanizer. The deethanizer has a temperature at a top thereof of −20-30° C., preferably 5-30° C., a temperature at a bottom thereof of 50-110° C., preferably 22-85° C., and an internal pressure of 2.2-3.8 M PaG, preferably 2.5-3.2 MPaG, more preferably 2.6-3.0 MPaG. When it is intended to obtain the $C_3$ product mainly containing $C_3$ and the liquid-phase material mainly containing $C_2$ and $C_4$, the third separation is performed in a depropanizer. The depropanizer has a temperature at a top thereof of 20-60° C., a temperature at a bottom thereof of 70-120° C., and an internal pressure of 1.2-2.5 MPaG.

In some preferred embodiments of the present invention, in step (d), when it is intended to obtain the $C_4$ product mainly containing $C_4$ and the $C_3$ product mainly containing $C_3$, the fourth separation is performed in a depropanizer. The depropanizer has a temperature at a top thereof of 20-60° C., a temperature at a bottom thereof of 70-120° C., and an internal pressure of 1.2-2.5 MPaG. When it is intended to obtain the $C_4$ product mainly containing $C_4$ and the $C_2$ product mainly containing $C_2$, the fourth separation is performed in a deethanizer. The deethanizer has a temperature at a top thereof of −20-30° C., preferably 5-30° C., a temperature at a bottom thereof of 50-110° C., preferably 22-85° C., and an internal pressure of 2.2-3.8 MPaG, preferably 2.5-3.2 MPaG, and more preferably 2.6-3.0 MPaG.

In some preferred embodiments of the present invention, in step (e), the rectification is performed at conditions including: a temperature of 45-65° C., preferably 45-60° C., and a pressure of 1.8-2.0 MPaG. The rectification is preferably performed in a rectifying column.

In some preferred embodiments of the present invention, the gas-phase material mainly containing $H_2$ and $C_1$ is treated with the absorbent at conditions including: a temperature of 5-25° C., and a pressure of 2.0-3.5 MPaG, preferably 2.1-2.9 MPaG, more preferably 2.2-2.7 MPaG.

According to the present invention, amine washing can be performed in a desulfurizing column, and a solvent to be used can be selected based on a content of $CO_2$ in a stream to be treated. Preferably, when the content of $CO_2$ in the stream to be treated by amine washing is less than or equal to 1000 ppmv, a lean amine solution is MDEA solvent, and because the use of a conventional MDEA solvent does not lead to a large consumption of alkali liquor in a downstream liquefied gas sweetening column, it is not necessary to provide a separate amine solution regeneration system, and a rich amine solution at a bottom of the desulfurizing column is collected. When the content of $CO_2$ in the stream to be treated is greater than 1000 ppmv, the lean amine solution is a composite solvent (i.e., a modified solvent based on MDEA), and it is necessary to provide a separate amine solution regeneration system, which, in particular, serves to send the lean amine solution having absorbed $H_2S$ and $CO_2$ in the desulfurizing column to a solvent regeneration column, and return the lean amine solution after regeneration to the desulfurizing column as an absorbent.

In the present invention, in the desulfurizing column, $H_2S$ and $CO_2$ are removed as the stream to be amine-washed comes into gas-liquid contact with the lean amine solution solvent, which can not only result in a content of hydrogen sulfide in the stream to be amine-washed of less than 20 ppmv, but also achieve a removal efficiency of $CO_2$ of up to 90-95 wt %, thereby effectively reducing the content of $CO_2$ in the stream entering into the alkaline sweetening reactor, and further decreasing the consumption of alkali liquor. Meanwhile, preferably, a temperature of the lean amine solution absorbent is controlled to be 3-8° C. higher than that of the stream to be amine-washed, so that the $C_3$/$C_4$ components in the stream to be amine-washed can be effectively prevented from being condensed into the amine solution to cause amine solution foaming.

According to the present invention, alkali washing can be performed in the sweetening column. In the sweetening column, mercaptans are removed by using alkali liquor, during which the alkali liquor is contacted with the stream to be alkali washed, which has better effects than liquid-liquid contact in the existing technologies as it can reduce a content of mercaptans in the stream to be alkali washed to be less than 20 ppmw. The mercaptans-removed stream to be treated can be sent to a water washing tank, in which the stream to be alkali washed is subjected to water washing to reach acid-base equilibrium to prevent the stream to be alkali washed from carrying alkali to corrode a downstream device.

According to the present invention, water washing can be performed in a washing tank. A temperature of water washing used water in the washing tank is 3-8° C. higher than that of the stream to be water washed, so that the $C_3$/$C_4$ components in the stream to be water washed can be prevented from being condensed into the water washing used water and thus the water washing used water can be prevented from carrying hydrocarbons.

According to the present invention, cold water refrigerated by lithium bromide is used as a coolant in the absorption column.

According to the present invention, an absorbent used in the absorption column can be derived from a self-balanced $C_4$/C5 component in the system and does not need to be introduced from the outside of the system.

According to the present invention, if the depropanization is performed first, it can cause the problem that mixed $C_2$ component separated out in the subsequent deethanization will contain about 20 v % of mixed $C_3$ component, and further cause the problem that the impurity-removed mixed $C_2$ component will still need to be sent to a downstream ethylene unit for continued recovery of $C_2$ and $C_3$.

According to the present invention, if the depropanization is performed first, then when the deethanization is performed, to perform fine separation in the deethanizer can ensure that the $C_2$ separated out contains basically no $C_3$, and the impurity-removed stream at the top of the deethanizer can be directly sent to a downstream ethylene unit for recovery of $C_2$ or for direct use. But at this moment, it is required that a lowest temperature at the top of the deethanizer be as low as −20° C., and the conventional lithium bromide refrigeration cannot meet this requirement; it is therefore necessary to provide a propylene refrigeration compressor, and a distillate at the top of the depropanizer needs to be dried and then sent into the deethanizer.

According to the present invention, if fine separation is not conducted in the deethanizer, the lowest temperature at the top of the deethanizer needs to be merely about 15° C., and the conventional lithium bromide refrigeration can meet this requirement.

In order to achieve the above-mentioned second objective, the present invention adopts the following technical solutions.

A system for treating oil gas comprising, connected in sequence, a light hydrocarbon extraction unit for extracting a first gas-phase material mainly containing $H_2$ and $C_1$-$C_4$, and a separation unit for separating the first gas-phase material to obtain a dry gas product mainly containing $H_2$ and $C_1$, a $C_2$ product mainly containing $C_2$, a $C_3$ product mainly containing $C_3$, and a $C_4$ product mainly containing $C_4$.

In some preferred embodiments of the present invention, an impurity removing unit is further provided between the light hydrocarbon extraction unit and the separation unit. The impurity removing unit is used for removing an acidic substance and a mercaptan. The acidic substance is specifically hydrogen sulfide and/or carbon dioxide.

In some preferred embodiments of the present invention, the impurity removing unit includes a gas phase impurity removing unit and optionally a liquid phase impurity removing unit. The gas phase impurity removing unit includes a rich gas desulfurizing column and a rich gas sweetening column, and preferably includes a gas phase water washing column. The liquid phase impurity removing unit includes a liquid hydrocarbon desulfurizing column and a liquid hydrocarbon sweetening reactor, and preferably includes a liquid-hydrocarbon water washing column.

In some preferred embodiments of the present invention, the separation unit includes, connected in sequence, a first separation device, a second separation device, a third separation device, and a fourth separation device.

The first separation device is used for separating the first gas-phase material mainly containing $H_2$ and $C_1$-$C_4$ into a gas-phase material mainly containing $H_2$ and $C_1$ and a liquid-phase material mainly containing $C_1$-$C_4$.

The second separation device is used for separating the liquid-phase material mainly containing $C_1$-$C_4$ into a gas-phase material mainly containing $C_1$ and a liquid-phase material mainly containing $C_2$-$C_4$.

The third separation device is used for separating the liquid-phase material mainly containing $C_2$-$C_4$ into a product mainly containing $C_2$ and a liquid-phase material mainly containing $C_3$-$C_4$, or into a $C_3$ product mainly containing $C_3$ and a liquid-phase material mainly containing $C_2$ and $C_4$.

The fourth separation device is used for separating the liquid-phase material mainly containing $C_3$-$C_4$ or the liquid-phase material mainly containing $C_2$ and $C_4$ into a $C_4$ product mainly containing $C_4$ and a $C_3$ product mainly containing $C_3$ or a $C_2$ product mainly containing $C_2$.

In some preferred embodiments of the present invention, the separation unit further includes a fifth separation device connected with the first separation device. The fifth separation device is used for treating the gas-phase material mainly containing $H_2$ and $C_1$ to obtain the dry gas product mainly containing $H_2$ and $C_1$ and a liquid-phase material mainly containing an absorbent.

In some preferred embodiments of the present invention, the separation unit further includes a sixth separation device for rectifying the $C_3$ product to obtain a propane product mainly containing propane and a propylene product mainly containing propylene.

In order to realize the aforementioned objectives, the present invention provides a method for separation of light hydrocarbons. The method for separation of light hydrocarbons includes the following steps.

(1) Gas-liquid separation: an oil gas from an upstream device, for example, a gas phase at a top of a fluid catalytic cracking fractionator, is condensed and cooled and then sent to a gas-liquid separation tank I for gas-liquid separation; a resulting liquid phase at a bottom of the gas-liquid separation tank I is sent to a debutanizer, and a resulting gas phase at a top of the gas-liquid separation tank I is compressed and sent to the debutanizer.

(2) Debutanization: The gas phase and the liquid phase from step (1) enter into the debutanizer; a resulting gas phase at a top of the debutanizer is distilled off from the top of the debutanizer, subjected to amine washing and alkali washing, and then sent to a cooling unit, and at least part of a resulting liquid phase at a bottom of the debutanizer is collected as a stable gasoline product.

(3) Cooling: Light hydrocarbons having been subjected to the amine washing and the alkali washing are cooled preliminarily in the cooling unit; a resulting cooled liquid phase is pressurized and then sent to a cooling unit III, and a resulting cooled gas phase is compressed, re-cooled, and then sent to the cooling unit III.

(4) Post-cooling: The gas phase and the liquid phase from step (3) are preliminarily mixed and cooled in the cooling unit III and then sent to a feeding tank as a mixed stream.

(5) Feeding: The mixed stream from the cooling unit III is mixed and pre-absorbed to reach gas-liquid equilibrium in the feeding tank; a resulting gas phase at a top of the feeding tank is sent to an absorption column, and a resulting liquid phase at a bottom of the feeding tank is sent to a demethanizer.

(6) Absorption: In the absorption column, a mixture of $C_4$/$C_5$ is used as an absorbent to absorb $C_2$ and $C_{2+}$ components present in the gas phase from the top of the feeding tank, and to simultaneously absorb part of methane; a resulting gas phase at a top of the absorption column is sent downstream for further recovery of the absorbent, and a resulting liquid phase at a bottom of the absorption column is returned to the cooling unit III.

(7) Demethanization: The liquid phase from the bottom of the feeding tank is subjected to removal of methane and simultaneously to removal of small part of $C_2$ and $C_{2+}$ components in a demethanizer; a resulting gas phase at a top of the demethanizer is sent to the cooling unit III, and a resulting liquid phase at a bottom of the demethanizer is sent to a deethanizer.

(8) Deethanization: The liquid phase from the bottom of the demethanizer is subjected to separation in the deethanizer to obtain a $C_2$ component; a mixed $C_2$ component obtained from the separation is collected from a top of the deethanizer as a mixed $C_2$ product, and resulting liquid-phase $C_3$ and $C_{3+}$ components at a bottom of the deethanizer are sent to a depropanizer.

(9) Depropanization: The liquid-phase components from the bottom of the deethanizer are subjected to further separation in the depropanizer; a $C_3$ component obtained from the separation is collected from a top of the depropanizer and sent to a propylene rectifying column for further rectification; at least part of components at a bottom of the depropanizer is sent as a mixed $C_4/C_5$ absorbent to an absorption column, and the rest is collected as a mixed $C_4/C_5$ product.

(10) Propylene rectification: The gas phase from the top of the depropanizer is subjected to further rectification in the propylene rectifying column; a resulting gas phase at a top of the propylene rectifying column is collected as a propylene product, and a resulting liquid phase at a bottom of the propylene rectifying column is collected as a propane product.

According to the present invention, preferably, the method for separation of light hydrocarbons further includes a following step (11).

(11) Recovery of absorbent: In an absorbent recovery column, at least part of the stable gasoline product collected in step (2) is used as an absorbent to absorb $C_4$ and $C_{4+}$ components present in the gas phase from the top of the absorption column, and simultaneously to absorb small amounts of $C_2/C_3$ components; a resulting gas phase at a top of the absorbent recovery column is collected as a dry gas, and a resulting liquid phase at a bottom of the absorbent recovery column is sent to a debutanizer.

According to the present invention, preferably, the debutanizer has an operating temperature of 40-70° C., and an operating pressure of 1.0-1.6 MPaG. Total reflux is adopted at a top of the debutanizer. A gas phase resulted at the top of the debutanizer is collected from a reflux tank at the top of the debutanizer. The reflux tank at the top of the debutanizer has a temperature of 15-40° C. The gas phase at the top of the debutanizer has contents of $C_5$ and $C_{5+}$ components of less than 5 wt %. The stable gasoline at the bottom of the debutanizer has a dry point of less than 204° C.

In the present invention, the whole gas phase at the top of the debutanizer is collected. In order to meet requirements for recovery of related products, it is necessary to subject the whole gas phase to impurity removal before it is subjected to separation in a next step. The impurity removal mainly includes amine washing for removing $H_2S$ and alkali washing for removing mercaptans. Meanwhile, in the present invention, the stable gasoline is separated out in advance in the debutanizer, and the stable gasoline does not participate in the downstream separation process for light hydrocarbons, which greatly reduce energy consumption during the process.

In the present invention, the impurity-removed gas-phase component is cooled and compressed before being sent into the feeding tank. The gas phase can be pressurized by adopting one-stage or multi-stage compression. The cooled liquid phase and the cooled and compressed gas phase are both sent into the feeding tank. Preferably, the feeding tank has an operating temperature of 5-25° C., and an operating pressure of 2.0-3.5 MPaG.

According to the present invention, preferably, the absorption column has an operating pressure of 2.0-3.5 MPaG; the whole absorption column has an operating temperature of 5-25° C.; cold water refrigerated by lithium bromide is used as a coolant for cooling. In the present invention, the mixed $C_4/C5$ absorbent adopted in the absorption column comes from the bottom of the depropanizer and is self-balanced $C_4/C5$ components in the system, and does not need to be introduced from the outside of the system.

According to the present invention, preferably, the deethanizer has an operating temperature of 5-20° C. and an operating pressure of 2.5-3.8 MPaG at the top thereof. The mixed $C_2$ product at the top of the deethanizer contains 10-25 vol % of propylene. In the present invention, the mixed $C_2$ product at the top of the deethanizer can be subjected to impurity removal and then sent to an ethylene unit to recover a $C_2$ component and a propylene component. The impurity removal can be performed by a person skilled in the art using a conventional impurity removal method in the art based on specific situations, which can be hydrogenation to remove $O_2$, alkyne and $NO_x$, drying to remove $H_2O$ by using a molecular sieve, and adsorption to remove COS, mercury, etc.

According to the present invention, preferably, the absorbent recovery column has an operating temperature of 5-50° C., and an operating pressure of 1.9-3.4 MPaG; the stable gasoline absorbent has a dry point of less than 204° C.

The present invention, in another aspect, provides a device for separation of light hydrocarbons. The device for separation of light hydrocarbons comprises: a light hydrocarbon feeding pipeline, a gas-liquid separation tank I, a compressor I, a compressor II, a debutanizer, a rich gas desulfurizing column, a rich gas sweetening column, a cooling unit I, a compressor III, a cooling unit II, a cooling unit III, a feeding tank, an absorption column, a demethanizer, a deethanizer, a depropanizer, and a propylene rectifying column.

The light hydrocarbon feeding pipeline is connected with an inlet of the gas-liquid separation tank I. The gas-liquid separation tank I is connected at a top thereof sequentially with the compressor I, the compressor II, and the debutanizer, and is connected at a bottom thereof with the debutanizer.

The debutanizer is connected at a top thereof sequentially with the rich gas desulfurizing column, the rich gas sweetening column, the cooling unit I, the compressor III, the cooling unit II, the cooling unit III, and the feeding tank, and is provided at a bottom thereof with a stable gasoline collecting pipeline.

The cooling unit I is directly connected with the cooling unit III through a pipeline.

The feeding tank is connected at a top thereof with the absorption column, and is connected at a bottom thereof with the demethanizer.

The absorption column is connected at a top thereof with a downstream device, is connected at a bottom thereof with the cooling unit III, and is provided on an upper portion thereof with a mixed $C_4$ absorbent feeding pipeline.

The demethanizer is connected at a top thereof with the cooling unit III, and is connected at a bottom thereof with the deethanizer.

The deethanizer is provided at a top thereof with a mixed $C_2$ collecting pipeline, and is connected at a bottom thereof with the depropanizer.

The depropanizer is connected at a top thereof with the propylene rectifying column, and is provided at a bottom thereof with a mixed $C_4/C5$ product collecting pipeline which is connected with a mixed $C_4/C5$ absorbent feeding pipeline.

The propylene rectifying column is provided at a top thereof with a propylene product collecting pipeline, and is provided at a bottom thereof with a propane product collecting pipeline.

According to the present invention, preferably, the downstream device includes an absorbent recovery column. The absorbent recovery column is provided at a top thereof with a dry gas collecting pipeline, is connected at a bottom thereof with the debutanizer, and is provided on an upper portion thereof with a stable gasoline absorbent feeding pipeline which is connected with the stable gasoline collecting pipeline of the debutanizer.

In the present invention, the compressor I can be divided into multiple stages. A liquid phase collecting pipeline between the stages is connected with the debutanizer.

In the present invention, in order to maintain a stable operating temperature in the entire absorption column, the absorption column is preferably provided with two to five middle-stage refluxes, and it is not necessary to provide a condenser at the top and a reboiler at the bottom of the absorption column. A gas phase from the feeding tank is fed from the bottom of the absorption column, and an absorbent is fed from the top of the absorption column.

According to the present invention, preferably, the demethanizer is not provided with a condenser at the top thereof, but a reboiler is provided at the bottom thereof. A liquid phase from the feeding tank is fed from the top of the demethanizer. The device for separation of light hydrocarbons does not include a dehydration device.

In order to achieve the above objectives, the present invention provides a method for low-pressure desulfurization of an oil gas. The method comprises the following steps.

(1) Gas-liquid separation: an oil gas from an upstream device is condensed and cooled, and then sent to a gas-liquid separation tank I for gas-liquid separation. A resulting liquid phase at a bottom of the gas-liquid separation tank is pressurized and then sent to a debutanizer, and a resulting gas phase at a top of the gas-liquid separation tank is compressed by a compressor and then sent to the debutanizer.

(2) Debutanization: The gas phase and the liquid phase from step (1) enter into the debutanizer. A gas phase distilled off at a top of the debutanizer is condensed and then sent into a reflux tank at the top of the debutanizer for separation to obtain a rich gas and a liquid phase. The rich gas is subjected further to impurity removal, and the liquid phase is returned to the debutanizer. At least part of a resulting liquid phase at the bottom of the debutanizer is collected as a stable gasoline product.

(3) Impurity removal: The rich gas from the top of the debutanizer is subjected sequentially to removal of $H_2S$ and $CO_2$ in a rich gas desulfurizing column by using a lean amine solution as an absorbent, to removal of mercaptans in a rich gas sweetening column by using an alkali liquor as an absorbent, and to water washing in a rich gas water washing tank to reach acid-base equilibrium. The impurity-removed rich gas is collected from a top of the rich gas water washing tank.

The present invention adopts a pre-positioned debutanizer for separating the oil gas in advance into gasoline and a rich gas. All hydrogen sulfide and lighter mercaptans go into the rich gas. The rich gas is then sequentially passed through the rich gas desulfurizing column, the rich gas sweetening column, and the rich gas water washing tank to remove impurities contained therein.

In the present invention, a solvent used in the desulfurizing column can be selected based on a content of $CO_2$ in the rich gas. Preferably, when the content of $CO_2$ in the rich gas is less than or equal to 1000 ppmv, the lean amine solution is MDEA solvent, and because the use of a conventional MDEA solvent does not lead to a large consumption of alkali liquor in a downstream liquefied gas sweetening column, it is not necessary to provide a separate amine solution regeneration system, and a rich amine solution at a bottom of the desulfurizing column is collected. When the content of $CO_2$ in the rich gas is greater than 1000 ppmv, the lean amine solution is a composite solvent (i.e., a modified solvent based on MDEA), and it is necessary to provide a separate amine solution regeneration system, which, in particular, serves to send the lean amine solution having absorbed $H_2S$ and $CO_2$ in the desulfurizing column to a solvent regeneration column, and return the lean amine solution after regeneration to the desulfurizing column as an absorbent.

In the present invention, in the desulfurizing column, $H_2S$ and $CO_2$ are removed as the rich gas and the lean amine solution solvent come into gas-liquid contact, which can not only reduce a content of hydrogen sulfide in the rich gas to be less than 20 ppmv, but also achieve a removal efficiency of $CO_2$ of up to 90-95 wt %, by way of which the content of $CO_2$ in a stream entering a reactor for alkali washing to remove mercaptans can be effectively reduced, and thus consumption of alkali liquor can be reduced. Meanwhile, preferably, the lean amine solution absorbent is controlled to have a temperature that is 3-8° C. higher than that of the rich gas, so that the $C_3/C_4$ components in the rich gas can be effectively prevented from being condensed into the amine solution to cause the amine solution to foam.

In the present invention, the rich gas having been removed of $H_2S$ and $CO_2$ is sent to a rich gas sweetening column for further impurity removal. Alkali liquor is used in the sweetening column for removing mercaptans. The alkali liquor and the rich gas form gas-liquid contact, which has better effects than the liquid-liquid contact in the existing technologies, and can reduce a content of mercaptans in the rich gas to less than 20 ppmw. The mercaptans-removed rich gas is sent to a rich gas water washing tank and subjected to water washing to reach acid-base equilibrium, so as to prevent the rich gas from carrying an alkali to corrode a downstream device. Preferably, water washing used water in the water washing tank has a temperature 3-8° C. higher than a temperature of the rich gas, so as to prevent the $C_3/C_4$ components in the rich gas from being condensed into the water washing used water, and prevent the water washing used water from carrying hydrocarbon.

According to the present invention, preferably, a liquid phase between stages of the compressor is sent to a debutanizer.

The debutanizer has an operating temperature of 45-65° C. and an operating pressure of 1.0-1.5 MPaG at a top thereof, and has an operating temperature of 150-200° C. at a bottom thereof. The reflux tank has a temperature of 35-50° C.

The rich gas desulfurizing column has an operating temperature of 35-50° C., and an operating pressure of 1.0-1.5 MPaG.

The rich gas sweetening column has an operating temperature of 35-50° C., and an operating pressure of 0.9-1.4 MPaG;

The rich gas water washing tank has an operating temperature of 35-50° C., and an operating pressure of 0.9-1.4 MPaG.

In the present invention, the impurity-removed rich gas is subjected to further separation. Preferably, the method for treating the oil gas further comprises the following step (4). Step (4) Separation: The impurity-removed rich gas is cooled, subjected to gas-liquid separation, compressed, re-cooled and then passed through an absorption column, a demethanizer, a depropanizer, a deethanizer, and optionally a propylene rectifying column for further separation to obtain a dry gas, a $C_2$ component, a $C_3$ component, and a $C_4$ component, among which the $C_2$ component and the $C_3$ component are collected as a $C_2$ product and a $C_3$ product, respectively, and at least part of the $C_4$ component is sent as a mixed $C_4$ absorbent to the absorption column and the rest is collected as a mixed $C_4$ product.

The above separation may be specifically as follows.

Cooling: The impurity-removed rich gas is cooled preliminarily in a cooling unit I and then sent to a gas-liquid separation tank II; a resulting gas phase at a top of the gas-liquid separation tank II is compressed and re-cooled and then sent to a cooling unit III, and a resulting liquid phase at a bottom of the gas-liquid separation tank II is pressurized and then sent to a cooling unit III.

Post-cooling: The preliminarily pressurized and cooled gas phase and the pressurized liquid phase are further mixed and cooled in the cooling unit III and then sent to a feeding tank as a mixed stream.

Feeding: The mixed stream from the cooling unit III is mixed and pre-absorbed to reach gas-liquid equilibrium in the feeding tank; a resulting gas phase at a top of the feeding tank is sent to an absorption column, and a resulting liquid phase at a bottom of the feeding tank is sent to a demethanizer.

Absorption: In the absorption column, a mixed $C_4$ is used as an absorbent to absorb $C_2$ and $C_{2+}$ components present in the gas phase from the top of the feeding tank, and to simultaneously co-absorb part of methane; a resulting gas phase at a top of the absorption column is sent to an absorbent recovery column for further recovery of the absorbent, and a resulting liquid phase at a bottom of the absorption column is returned to the cooling unit III.

Demethanization: the liquid phase from the bottom of the feeding tank is subjected to removal of methane and simultaneously to removal of small part of $C_2$ and $C_{2+}$ components in the demethanizer; a resulting gas phase at a top of the demethanizer is sent to the cooling unit III, and a resulting liquid phase at a bottom of the demethanizer is sent to a depropanizer.

Depropanization: The liquid phase from the bottom of the demethanizer is subjected to separation in the depropanizer; $C_3$ and $C_{3-}$ components obtained from the separation are collected from an upper portion of the depropanizer, optionally dried, and then sent to a deethanizer; at least part of resulting components at a bottom of the depropanizer is sent as a mixed $C_4$ absorbent to the absorption column, and the rest is collected as a mixed $C_4$ product.

Deethanization: The gas phase from the upper portion of the depropanizer is subjected to further separation in the deethanizer; a mixed $C_2$ component obtained from the separation is optionally subjected to impurity removal, and then collected from a top of the deethanizer as a mixed $C_2$ product, and a resulting liquid phase at a bottom of the deethanizer is collected as a mixed $C_3$ component.

According to the present invention, preferably, the feeding tank has an operating temperature of 5-25° C., and an operating pressure of 2.2-2.8 MPaG.

The absorption column has an operating temperature of 5-25° C., and an operating pressure of 2.1-2.7 MPaG. The absorbent in the absorption column is derived from the self-balanced mixed $C_4$ component in the system and does not need to be introduced from outside of the system.

The demethanizer has an operating temperature at a top thereof of 10-40° C., an operating temperature at a bottom thereof of 70-95° C., and an operating pressure of 2.3-2.9 MPaG.

The deethanizer has an operating temperature at a top thereof of from −20 to 20° C., an operating temperature at a bottom thereof of 55-85° C., and an operating pressure of 2.2-3.2 MPaG.

In the present invention, the order of conducting the depropanization and the deethanization is not particularly limited, and each possible order can meet the requirements of the process.

However, conducting the depropanation and the deethanization in a different order can lead to different operation conditions of the deethanizer and different components of the recovered mixed $C_2$. Those skilled in the art can make adjustment according to conventional technical means in the art.

In the present invention, the mixed $C_3$ component obtained from the separation can be further rectified to obtain a propylene product and a propane product. Preferably, the separation further includes the following.

Propylene rectification: The mixed $C_3$ component collected from the bottom of the deethanizer is sent to a propylene rectifying column for further rectification; a resulting gas phase at a top of the propylene rectifying column is cooled and then collected as a propylene product, and a resulting liquid phase at a bottom of the propylene rectifying column is collected as a propane product.

According to the present invention, preferably, the propylene rectifying column has an operating temperature of 45-60° C., and an operating pressure of 1.8-2.0 MPaG.

In order to further recover the mixed $C_4$ absorbent entrained in the stream at the top of the absorption column, preferably, the separation further includes the following.

Absorbent recovery: In an absorbent recovery column, at least part of the stable gasoline product collected in step (2) is used as an absorbent to absorb $C_4$ and $C_{4+}$ components present in the gas phase from the top of the absorption column, and to simultaneously absorb small amounts of $C_2/C_3$ components; a resulting gas phase at a top of the absorbent recovery column is collected as a dry gas, and a resulting liquid phase at a bottom of the absorbent recovery column is returned to the debutanizer.

In the above method for separation of light hydrocarbons according to the present invention, the stream is first subjected to removal of $C_4$ and $C_{4+}$ components and then subjected to separation for $C_2$, by way of which the mixed $C_2$ obtained from the separation will contain about 20 v % of a mixed $C_3$ component, and the impurity-improved mixed $C_2$ component still needs to be sent to a downstream ethylene unit for continued recovery of $C_2$ and $C_3$. However, because fine separation is not used in the deethanizer, and a minimum temperature at the top of the deethanizer needs only to be around 15° C., conventional lithium bromide refrigeration can meet this requirement. When fine separation is used in the deethanizer, it can be ensured that the $C_2$ component obtained from the separation basically contains no $C_3$, and the impurity-removed stream at the top of the deethanizer can be directly sent to the downstream ethylene unit for recovery of $C_2$ or for direct use. Accordingly, due to the fine separation in the deethanizer, the minimum temperature at the top of the deethanizer needs to be as low as −20° C., and the conventional lithium bromide refrigeration cannot meet this requirement; a propylene refrigeration compressor thus needs to be provided, and a distillate at the top of the depropanizer has to be dried and then sent to the deethanizer.

The present invention, in another aspect, provides a device for treating an oil gas. The device for treating an oil gas comprises: an oil gas feeding pipeline, a gas-liquid separation tank I, a compressor I, a compressor II, a debutanizer, a rich gas desulfurizing column, a rich gas sweetening column, and a rich gas water washing tank.

The oil gas feeding pipeline is connected with an inlet of the gas-liquid separation tank I. The gas-liquid separation tank I is connected at a top thereof sequentially with the compressor I, the compressor II, and the debutanizer, and is connected at a bottom thereof with the debutanizer.

The debutanizer is provided at a top thereof with a reflux tank. The reflux tank is connected at a top thereof with the rich gas desulfurizing column, and is connected at a bottom thereof with the debutanizer. The debutanizer is provided at a bottom thereof with a stable gasoline collecting pipeline.

The rich gas desulfurizing column is provided on an upper portion thereof with a lean amine solution feeding pipeline which is optionally provided thereon with a lean amine solution cooling unit. The rich gas desulfurizing column is connected at a top thereof with the rich gas sweetening column, and is provided at a bottom thereof with a rich amine solution collecting pipeline.

The rich gas sweetening column is provided on an upper portion thereof with an alkali liquor feeding pipeline, is connected at a top thereof with a rich gas water washing tank, and is provided at a bottom thereof with a rich amine solution collecting pipeline.

The rich gas water washing tank is provided at a top thereof with a light hydrocarbon collecting pipeline, and is connected at a bottom thereof first with a rich gas water washing circulating pump and then with a water washing used water heating unit and a water washing discharge pipeline, respectively. The water washing used water heating unit is connected with an upper portion of the rich gas water washing tank.

According to the present invention, preferably, the device for treating the oil gas further comprises a solvent regeneration column with which the rich amine solution collecting pipeline is connected. The solvent regeneration column is connected at a bottom thereof with the lean amine solution feeding pipeline, and is provided at a top thereof with an acidic gas collecting pipeline.

According to the present invention, preferably, the device further includes a separation unit with which the light hydrocarbon collecting pipeline is connected.

The separation unit includes: a cooling unit I, a gas-liquid separation tank II, a compressor III, a cooling unit II, a cooling unit III, a feeding tank, an absorption column, a demethanizer, a deethanizer, and a depropanizer.

The deethanizer is provided at a top thereof with a mixed $C_2$ collecting pipeline which is optionally provided thereon with an impurity treatment unit. The depropanizer is provided at a bottom thereof with a mixed $C_4$ product collecting pipeline. The mixed $C_4$ product collecting pipeline is divided into two branches, one of which serves as a mixed $C_4$ absorbent feeding pipeline.

Preferably, the light hydrocarbon collecting pipeline is sequentially connected with the cooling unit I and the gas-liquid separation tank II. The gas-liquid separation tank II is sequentially connected at a top thereof with the compressor III, the cooling unit II, the cooling unit III, and the feeding tank, and is connected at a bottom thereof sequentially with the cooling unit III and the feeding tank.

The feeding tank is connected at a top thereof with the absorption column, and is connected at a bottom thereof with the demethanizer.

The absorption column is optionally connected at a top thereof with an absorbent recovery column, is connected at a bottom thereof with the cooling unit III, and is provided on an upper portion thereof with a mixed $C_4$ absorbent feeding pipeline.

The demethanizer is connected at a top thereof with the cooling unit III, and is connected at a bottom thereof to the depropanizer.

The depropanizer is connected on an upper portion thereof first with a drying unit optionally then with the deethanizer, and is provided at a bottom thereof with a mixed $C_4$ product collecting pipeline. The mixed $C_4$ product collecting pipeline is divided into two branches, one of which serves as a mixed $C_4$ absorbent feeding pipeline.

The deethanizer is provided at a top thereof with a mixed $C_2$ collecting pipeline optimally provided thereon with an impurity treatment unit, and is provided on a bottom thereof with a $C_3$ collecting pipeline optionally connected with a propylene rectifying column.

More preferably, the separation unit further includes the propylene rectifying column and/or the absorbent recovery column.

The absorbent recovery column is provided at a top thereof with a dry gas collecting pipeline, and is connected at a bottom thereof with the debutanizer. The absorbent recovery column is provided on an upper portion thereof with a stable gasoline absorbent feeding pipeline. The stable gasoline collecting pipeline of the debutanizer is divided into two branches, one of which serves as the stable gasoline absorbent feeding pipeline.

The propylene rectifying column is provided at a top thereof with a propylene product collecting pipeline, and is provided at a bottom thereof with a propane product collecting pipeline.

In the present invention, the compressor I can be divided into multiple stages. A liquid phase collecting pipeline between the stages is connected with the debutanizer.

In the present invention, in order to maintain a uniform operating temperature throughout the absorption column and ensure absorption effects, the absorption column can be provided with two to five middle-stage refluxes. Besides, it is not necessary to provide a condenser at the top of the absorption column and to provide a reboiler at the bottom of the absorption column. The gas phase from the feeding tank is fed from the bottom of the absorption column, and the absorbent is fed from the upper portion of the absorption column.

In the present invention, it is not necessary to provide the separation unit with a dehydration device. The demethanizer may not be provided at the top thereof with a condenser, and may be provided at the bottom thereof with a reboiler. The liquid phase from the feeding tank is fed from the top of the demethanizer.

In order to achieve the above objectives, the present invention provides a method for high-pressure desulfurization and separation of an oil gas. The method includes the following steps.

(1) First gas-liquid separation: an oil gas from an upstream device is condensed and cooled and then sent to a gas-liquid separation tank I for gas-liquid separation. A resulting liquid phase at a bottom of the gas-liquid separation tank I is pressurized and then sent to a debutanizer, and a gas phase at a top of the gas-liquid separation tank I is compressed by a compressor and then sent to the debutanizer.

(2) Debutanization: The gas phase and the liquid phase from step (1) enter into the debutanizer. A gas phase distilled off at a top of the debutanizer is condensed and then sent into a reflux tank at the top of the debutanizer. A resulting gas phase at a top of the reflux tank at the top of the debutanizer is compressed and cooled and then sent to a gas-liquid separation tank II, and a resulting liquid phase at a bottom of the reflux tank is pressurized and then sent to the gas-liquid separation tank II. At least part of a resulting liquid phase at a bottom of the debutanizer is collected as a stable gasoline product.

(3) Second gas-liquid separation: Materials are mixed to reach gas-liquid equilibrium in the gas-liquid separation tank II, and then subjected to separation to obtain a gas phase and a liquid phase. The gas phase and the liquid phase are then subjected to impurity removal, respectively.

(4) Gas phase impurity removal: The gas phase at a top of the gas-liquid separation tank II obtained from the separation in the gas-liquid separation tank II is sequentially subjected to removal of $H_2S$ and $CO_2$ in a rich gas desulfurizing column with a lean amine solution as an absorbent, to removal of mercaptans in a rich gas sweetening column with an alkali liquor as an absorbent, and then sent to a cooling unit III.

(5) Liquid phase impurity removal: The liquid phase at a bottom of the gas-liquid separation tank II obtained from the separation in the gas-liquid separation tank II is sequentially subjected to removal of $H_2S$ and $CO_2$ in a liquid hydrocarbon desulfurizing column, to removal of mercaptans in a liquid hydrocarbon sweetening reactor, and then sent to a cooling unit III.

(6) Cooling: Impurity-removed gaseous light hydrocarbons and impurity-removed liquid hydrocarbons are mixed and cooled in the cooling unit III and then sent to a feeding tank as a mixed steam.

(7) Feeding: The mixed stream from the cooling unit III is mixed and pre-absorbed to reach gas-liquid equilibrium in the feeding tank. A resulting gas phase at a top of the feeding tank is sent to an absorption column, and a resulting liquid phase at a bottom of the feeding tank is sent to a separation unit.

(8) Absorption: In the absorption column, a mixed $C_4$ is used as an absorbent to absorb $C_2$ and $C_{2+}$ components present in the gas phase from the top of the feeding tank, and to simultaneously co-absorb part of methane. A resulting gas phase at a top of the absorption column is sent to a downstream device for further recovery of the absorbent, and a resulting liquid phase at a bottom of the absorption column is returned to the cooling unit III.

(9) Separation: The liquid phase from the bottom of the feeding tank is passed through a demethanizer, a deethanizer, a depropanizer, and optionally a propylene rectifying column in the separation unit for further separation to obtain a $C_2$ component, a $C_3$ component, and a $C_4$ component, among which the $C_2$ component and the $C_3$ component are collected as a $C_2$ product and a $C_3$ product, respectively, and at least part of the $C_4$ component is sent as a mixed $C_4$ absorbent to the absorption column and the rest is collected as a mixed $C_4$ product.

The present invention has a wide range of applications. Oil gas (comprising $H_2$, $C_1$-$C_4$, gasoline components, and small amounts of non-hydrocarbon components) produced in processes with high gas yields, such as catalytic cracking, catalytic pyrolysis, delayed coking and so on, can all be subjected to separation for light hydrocarbons and recovery of liquefied gases by using the device of the present invention.

In the present invention, the oil gas from the upstream device is condensed and cooled, and then sent to the gas-liquid separation tank I for gas-liquid separation. The liquid phase at the bottom of the feeding tank I is pressurized by a pump and then sent to the debutanizer, and the gas phase at the top of the feeding tank I is compressed by the compressor and then sent to the debutanizer. Preferably, the compressor is divided into multiple stages, and a liquid phase generated between the stages of the compressor is sent to the debutanizer.

In the present invention, the stable gasoline is separated out in advance in the debutanizer. The stable gasoline does not participate in the downstream light hydrocarbon separation process, which can greatly reduce energy consumption during the process. Preferably, the debutanizer has an operating temperature of 45-50° C. and an operating pressure of 1.0-1.5 MPaG at a top thereof, and has an operating temperature of 180-220° C. at a bottom thereof. The reflux tank has a temperature of 40-45° C.

In the present invention, in order to meet requirements for the recovery of related products, it is necessary to remove impurities before a next step of separation. The impurity removal mainly includes amine washing for removal of $H_2S$ and alkali washing for removal of mercaptans. Desulfurization and sweetening of a gas phase conducted under a high pressure produces better effects, and to conduct the desulfurization and sweetening under a high pressure requires a desulfurization device of a small relatively volume; therefore, in the present invention, light hydrocarbons are separated into a gas phase and a liquid phase first, and then the gas phase and the liquid phase are respectively subjected to impurity removal. Preferably, the gas phase at the top of the reflux tank is compressed to 2.5-3.0 MPaG, cooled to 35-45° C., and then sent to the gas-liquid separation tank II. The liquid phase at the bottom of the reflux tank is pressurized to 2.8-3.3 MPaG and then sent to the gas-liquid separation tank II. After the compressed gas phase and the pressurized liquid phase in the gas-liquid separation tank II are mixed to reach gas-liquid equilibrium, the resulting mixture is subjected to separation again to obtain a gas phase and a liquid phase; the gas phase and the liquid phase are then subjected to impurity removal, respectively. Due to the low content of heavy hydrocarbons in the gas phase separated out, the amounts of heavy hydrocarbons condensed into the amine solution during desulfurization are also small, which effectively avoids foam entrainment of the desulfurization device caused by foaming of the amine solution and thus avoids effects on smooth operation of the device.

In the present invention, in order to meet requirements for the recovery of related products, preferably, a composite amine solution solvent (i.e., a modified solvent based on MDEA) is used in the amine washing for removal of $H_2S$ to simultaneously remove $H_2S$ and $CO_2$. $H_2S$ can be removed to a content of less than 10 ppmv, and $CO_2$ removal efficiency can be up to 90-95 wt %. The content of $CO_2$ in the stream within the alkali washing sweetening reactor is thus effectively decreased, and further the consumption of alkali liquor is decreased.

According to the present invention, preferably, the rich gas desulfurizing column has an operating temperature of 35-45° C., and an operating pressure of 2.5-3.0 MPaG; the rich gas sweetening column has an operating temperature of 35-45° C., and an operating pressure of 2.4-2.9 MPaG; the liquid hydrocarbon desulfurizing column has an operating temperature of 35-45° C., and an operating pressure of 3.0-3.5 MPaG.

In the present invention, the impurity-removed gas phase components need to be cooled and compressed before being sent into the feeding tank. The compression of the gas phase can be one-stage or multi-stage compression. The cooled liquid phase and the compressed and cooled gas phase are both sent to the feeding tank. Preferably, the feeding tank has an operating temperature of 5-25° C. and an operating pressure of 2.4-2.9 MPaG.

According to the present invention, preferably, the absorption column has an operating temperature of 5-25° C., and an operating pressure of 2.4 to 2.9 MPaG. In the present invention, the absorbent mixed $C_4$ absorbent used in the absorption column comes from the bottom of the depropanizer, and is a self-balanced $C_4$ component in the system and does not need to be introduced from outside the system.

According to the present invention, preferably, the separation in step (9) is performed according to one of the following two processes.

Process I: The separation includes the following steps in sequence.

Demethanization: The liquid phase from the bottom of the feeding tank is subjected to removal of methane and simultaneously to removal of small part of $C_2$ and $C_{2+}$ components in a demethanizer; a resulting gas phase at a top of the demethanizer is sent to the cooling unit, and a resulting liquid phase at a bottom of the demethanizer is sent to a deethanizer.

Deethanization: The liquid phase from the bottom of the demethanizer is subjected to separation in the deethanizer to obtain a $C_2$ component. A mixed $C_2$ component obtained from the separation is optionally subjected to impurity removal, and then collected from a top of the deethanizer as a mixed $C_2$ product, and resulting liquid-phase components of $C_3$ and $C_{3+}$ at a bottom of the deethanizer are sent to a depropanizer.

Depropanization: The liquid-phase components from the bottom of the deethanizer are subjected to further separation in the depropanizer. A $C_3$ component obtained from the separation is collected from an upper portion of the depropanizer. At least part of resulting components at a bottom of the depropanizer is sent as a mixed $C_4$ absorbent to an absorption column, and the rest is collected as a mixed $C_4$ product.

More preferably, the separation further comprises the following step.

Propylene rectification: The $C_3$ component from the upper portion of the depropanizer is subjected to further rectification in the propylene rectifying column. A resulting gas phase at a top of the propylene rectifying column is cooled and then collected as a propylene product, and a resulting liquid phase at a bottom of the propylene rectifying column is collected as a propane product.

Process II: The separation includes the following steps in sequence.

Demethanization: The liquid phase from the bottom of the feeding tank is subjected to removal of methane and simultaneously to removal of small part of $C_2$ and $C_{2+}$ components in a demethanizer. A resulting gas phase at a top of the demethanizer is sent to the cooling unit III, and a resulting liquid phase at a bottom of the demethanizer is sent to a depropanizer.

Depropanization: The liquid phase from the bottom of the demethanizer is subjected to further separation in the depropanizer; $C_3$ and $C_{3-}$ components obtained from the separation are collected from an upper portion of the depropanizer, optionally dried, and then sent to a deethanizer. At least part of components at a bottom of the depropanizer is sent as a mixed $C_4$ absorbent to an absorption column, and the rest is collected as a mixed $C_4$ product.

Deethanization: The gas phase from the upper portion of the depropanizer is subjected to further separation in the deethanizer. A mixed $C_2$ component obtained from the separation is optionally subjected to impurity removal, and then collected from a top of the deethanizer as a mixed $C_2$ product, and a resulting liquid phase at a bottom of the deethanizer is collected as a mixed $C_3$ component.

More preferably, the separation further comprises the following step.

Propylene rectification: The mixed $C_3$ component collected from the bottom of the deethanizer is subjected to further rectification in a propylene rectifying column. A resulting gas phase at a top of the propylene rectifying column is cooled and then collected as a propylene product, and a resulting liquid phase at a bottom of the propylene rectifying column is collected as a propane product.

In the above separation method according to the present invention, when the process II is used for the separation for light hydrocarbons, the stream is first subjected to removal of $C_4$ and $C_{4+}$ components and then subjected to separation for $C_2$, by way of which the mixed $C_2$ obtained from the separation will contain about 20 v % of a mixed $C_3$ component, and the impurity-improved mixed $C_2$ component still needs to be sent to a downstream ethylene unit for continued recovery of $C_2$ and $C_3$. However, because fine separation is not used in the deethanizer, and a minimum temperature at the top of the deethanizer needs only to be around 15° C., conventional lithium bromide refrigeration can meet this requirement. When fine separation is used in the deethanizer, it can be ensured that the $C_2$ component obtained from the separation basically contains no $C_3$, and the impurity-removed stream at the top of the deethanizer can be directly sent to the downstream ethylene unit for recovery of $C_2$ or for direct use. Accordingly, due to the fine separation in the deethanizer, the minimum temperature at the top of the deethanizer needs to be as low as −20° C., and the conventional lithium bromide refrigeration cannot meet this requirement; a propylene refrigeration compressor thus needs to be provided, and a distillate at the top of the depropanizer has to be dried and then sent to the deethanizer.

According to the present invention, preferably, the deethanizer has an operating temperature of 5-15° C. and an operating pressure of 2.2-3.0 MPaG at the top thereof, and has an operating temperature of 50-110° C. at the bottom thereof. Since the recovered $C_2$ product in the present invention contains 15-20% of propylene, the $C_2$ product is first removed of impurities such as $NO_x$, $O_2$ and heavy metals by the impurity treatment unit and then sent to the ethylene unit for recovery of resources such as ethylene, ethane, and propylene. The removal of impurities can be performed by those skilled in the art according to specific situations and using a conventional impurity removal method in the art. The impurity removal method can be removal of $O_2$, alkyne, and $NO_x$ by hydrogenation, removal of $H_2O$ by molecular sieve drying, removal of COS, mercury and so on by adsorption.

In the present invention, the mixed $C_3$ component separated out can be further rectified to obtain a propylene product and a propane product. Preferably, the propylene rectifying column has an operating temperature of 45-65° C., and an operating pressure of 1.8-2.0 MPaG.

In order to further recover the mixed $C_4$ absorbent entrained in the stream at the top of the absorption column, preferably, the method further includes the following step.

(10) Recovery of absorbent: In an absorbent recovery column, at least part of the stable gasoline product collected in step (2) is used as an absorbent to absorb $C_4$ and $C_{4+}$ components present in the gas phase from the top of the absorption column, and to simultaneously absorb small amounts of $C_2/C_3$ components. A resulting gas phase at a top of the absorbent recovery column is collected as a dry gas, and a resulting liquid phase at a bottom of the absorbent recovery column is returned to the debutanizer. Preferably, the absorbent recovery column has an operation temperature of 5-25° C., and an operating pressure of 2.3-2.8 MPaG.

The present invention, in another aspect, provides a device for high-pressure desulfurization and separation of an oil gas. The device includes: an oil gas feeding pipeline, a gas-liquid separation tank I, a compressor I, a compressor II, a debutanizer, a compressor III, a cooling unit II, a gas-liquid separation tank II, a rich gas desulfurizing column, a rich gas sweetening column, a liquid hydrocarbon desulfurizing column, a liquid hydrocarbon sweetening reactor, a cooling unit III, a feeding tank, an absorption column, and a separation unit.

The oil gas feeding pipeline is connected with an inlet of the gas-liquid separation tank I. The gas-liquid separation tank I is connected at a top thereof sequentially with the compressor I, the compressor II, and the debutanizer, and is connected at a bottom thereof with the debutanizer.

The debutanizer is provided at a top thereof with a reflux tank. The reflux tank is connected at a top thereof sequentially with the compressor II, the cooling unit II, and the gas-liquid separation tank II, and is connected at a bottom thereof first with a booster pump and then with the gas-liquid separation tank II. The debutanizer is provided at a bottom thereof with a stable gasoline collecting pipeline.

The gas-liquid separation tank II is connected a top thereof sequentially with the rich gas desulfurizing column, the rich gas sweetening column, and the cooling unit III, and is connected at a bottom thereof sequentially with the liquid hydrocarbon desulfurizing column, the liquid hydrocarbon sweetening reactor, and the cooling unit III.

The rich gas desulfurizing column is provided on an upper portion thereof with a lean amine solution feeding pipeline, and the rich gas sweetening column is provided on an upper portion thereof with an alkali liquor feeding pipeline.

The cooling unit III is connected with the feeding tank.

The feeding tank is connected at a top thereof with the absorption column, and is connected at a bottom thereof with the separation unit.

The absorption column is connected at a top thereof with a downstream device, is connected at a bottom thereof with the cooling unit III, and is provided on an upper portion thereof with a mixed $C_4$ absorbent feeding pipeline.

The separation unit comprises: a demethanizer, a deethanizer, a depropanizer, and an optional propylene rectifying column. The demethanizer is connected at a top thereof with the cooling unit III. The deethanizer is provided at a top thereof with a mixed $C_2$ collecting pipeline optionally provided thereon with an impurity treatment unit. The depropanizer is provided at a bottom thereof with a mixed $C_4$ product collecting pipeline. The mixed $C_4$ product collecting pipeline is divided into two branches, one of which serves as a mixed $C_4$ absorbent feeding pipeline.

In the present invention, further separation for $C_4$ and $C_{4-}$ components is performed in the separation unit. Preferably, in the separation unit, the demethanizer is connected at a top thereof with the cooling unit III, and is connected at a bottom thereof with the deethanizer; the deethanizer is provided at a top thereof with the mixed $C_2$ collecting pipeline optionally provided thereon with the impurity treatment unit, and is connected at a bottom thereof with the depropanizer; the depropanizer is provided on an upper portion thereof with a mixed $C_3$ collecting pipeline optionally connected with a propylene rectifying column, and is provided at a bottom thereof with the mixed $C_4$ product collecting pipeline, the mixed $C_4$ product collecting pipeline being divided into two branches, one of which serves as a mixed $C_4$ absorbent feeding pipeline. Or, preferably, the demethanizer is connected at a top thereof with the cooling unit III, and is connected at a bottom thereof with the depropanizer; the depropanizer is connected on an upper portion thereof with the deethanizer, and is provided at a bottom thereof with a mixed $C_4$ product collecting pipeline, the mixed $C_4$ product collecting pipeline being divided into two branches, one of which serves as a mixed $C_4$ absorbent feeding pipeline; the deethanizer is provided at a top thereof with a mixed $C_2$ collecting pipeline optionally provided thereon with an impurity treatment unit, and is provided at a bottom thereof with a mixed $C_3$ collecting pipeline optionally connected with a propylene rectifying column. More preferably, the propylene rectifying column is provided at a top thereof with a propylene product collecting pipeline, and is provided at a bottom thereof with a propane product collecting pipeline.

According to the present invention, preferably, the downstream device further includes an absorbent recovery column. The absorbent recovery column is provided at a top thereof with a dry gas collecting pipeline, is connected at a bottom thereof with the debutanizer, and is provided on an upper portion thereof with a stable gasoline absorbent feeding pipeline. The stable gasoline collecting pipeline of the debutanizer is divided into two branches, one of which serves as the stable gasoline absorbent feeding pipeline.

In the present invention, the compressor I can be divided into multiple stages. A liquid phase collecting pipeline between the stages is connected with the debutanizer.

In the present invention, in order to maintain a uniform operating temperature throughout the absorption column and ensure absorption effects, the absorption column can be provided with two to five middle-stage refluxes. Besides, it is not necessary to provide a condenser at the top of the absorption column and to provide a reboiler at the bottom of the absorption column. The gas phase from the feeding tank is fed from the bottom of the absorption column, and the absorbent is fed from the upper portion of the absorption column.

According to the present invention, preferably, the demethanizer is not provided at the top thereof with a condenser, and is provided at the bottom thereof with a reboiler. The liquid phase from the feeding tank is fed from the top of the demethanizer. The light dydrocarbon separation device does not include a dehydration device.

In order to achieve the above objectives, the present invention provides a method for recovery of an oil gas. The method comprises the following steps.

(1) First gas-liquid separation: an oil gas from an upstream device is condensed and cooled and then sent to a gas-liquid separation tank I for gas-liquid separation. A resulting liquid phase at a bottom of the gas-liquid separation tank I is pressurized and then sent to a light-heavy gasoline separation column, and a gas phase at a top of the gas-liquid separation tank I is compressed by a compressor and then sent to the light-heavy gasoline separation column.

(2) Light-heavy gasoline separation: Materials from the gas-liquid separation tank I enter the light-heavy gasoline separation column. A gas phase distilled off at a top of the light-heavy gasoline separation column is condensed and then sent to a reflux tank at the top of the light-heavy gasoline separation column. A resulting gas phase at a top of the reflux tank is compressed and then sent to light hydrocarbon-light gasoline separation column, and a liquid phase at a bottom of the reflux tank is pressurized and then sent to the light hydrocarbon-light gasoline separation column. At least part of a resulting liquid phase at a bottom of the light-heavy gasoline separation column is collected as a heavy gasoline product.

(3) Light hydrocarbon-light gasoline separation: A stream from the reflux tank at the top of the light-heavy gasoline separation column enters the light hydrocarbon-light gasoline separation column. A gas phase distilled off at a top of the light hydrocarbon-light gasoline separation column is sent to a reflux tank at a top of the light hydrocarbon-light gasoline separation column. A resulting gas phase at the top of the reflux tank is compressed and cooled and then sent to a gas-liquid separation tank II, and a resulting liquid phase at a bottom of the reflux tank is pressurized and then sent to the gas-liquid separation tank II. A resulting liquid phase at a bottom of the light hydrocarbon-light gasoline separation column is collected as light gasoline.

(4) Second gas-liquid separation: Materials are mixed to reach gas-liquid equilibrium in the gas-liquid separation tank II, and then subjected to further separation to obtain a gas phase and a liquid phase. The gas phase and the liquid phase are then subjected to impurity removal, respectively.

(5) Gas phase impurity removal: The gas phase at a top of the gas-liquid separation tank II obtained from the separation in the gas-liquid separation tank II is sequentially subjected to removal of $H_2S$ and $CO_2$ in a rich gas desulfurizing column with a lean amine solution as an absorbent, and to removal of mercaptans in a rich gas sweetening column with an alkali liquor as an absorbent, and then sent to a cooling unit III.

(6) Liquid phase impurity removal: The liquid phase at a bottom of the gas-liquid separation tank II obtained from the separation in the gas-liquid separation tank II is sequentially subjected to removal of $H_2S$ and $CO_2$ in a liquid hydrocarbon desulfurizing column, and to removal of mercaptans in a liquid hydrocarbon sweetening reactor, and then sent to the cooling unit III.

(7) Cooling: Impurity-removed gaseous light hydrocarbons and impurity-removed liquid light hydrocarbons are mixed and cooled in the cooling unit III and then sent to a feeding tank as a mixed stream.

(8) Feeding: The mixed stream from the cooling unit III is mixed and pre-absorbed to reach gas-liquid equilibrium in the feeding tank. A resulting gas phase at a top of the feeding tank is sent to an absorption column, and a resulting liquid phase at a bottom of the feeding tank is sent to a separation column.

(9) Absorption: In the absorption column, a mixed $C_4$ is used as an absorbent to absorb $C_2$ and $C_{2+}$ components present in the gas phase from the top of the feeding tank, and to simultaneously co-absorb part of methane. A resulting gas phase at a top of the absorption column is sent to a downstream device, and a resulting liquid phase at a bottom of the absorption column is returned to the cooling unit.

(10) Separation: The liquid phase from the bottom of the feeding tank is passed through a demethanizer, a deethanizer, a depropanizer, and optionally a propylene rectifying column for further separation in the separation unit to obtain a $C_2$ component, a $C_3$ component, and a $C_4$ component. The $C_2$ component is separated out in the deethanizer by using propane and/or a mixed $C_4$ as an absorbent. The $C_2$ component and the $C_3$ component are collected as a $C_2$ product and a $C_3$ product, respectively. At least part of the $C_4$ component is sent as a mixed $C_4$ absorbent to the absorption column and optionally a deethanizer, and the rest is collected as a mixed $C_4$ product.

The present invention has a wide range of applications. Oil gas (comprising $H_2$, $C_1$-$C_4$, gasoline components, and small amounts of non-hydrocarbon components) produced in processes with high gas yields, such as catalytic cracking, catalytic pyrolysis, delayed coking and so on, can all be subjected to separation for light hydrocarbons and recovery of liquefied gases by using the device of the present invention.

In the present invention, the oil gas from the upstream device is condensed and cooled and sent to the gas-liquid separation tank I for gas-liquid separation. The liquid phase at the bottom of the feeding tank I is pressurized by a pump and sent to the light-heavy gasoline separation column, and the gas phase at the top of the feeding tank I is compressed by the compressor and then sent to the light-heavy gasoline separation column. The compressor is divided into multiple stages, and the liquid phase generated between the stages of the compressor is sent to the light-heavy gasoline separation column. the oil gas is subjected to separation in the light-heavy gasoline separation column for heavy gasoline, and then subjected to separation in the light hydrocarbon-light gasoline separation column for light gasoline, by way of which light and heavy gasoline is separated out in advance and does not participate in the downstream light hydrocarbon separation process. This can greatly reduce energy consumption during the process. Preferably, the light-heavy gasoline separation column has an operating temperature at the top thereof of 60-85° C., an operating temperature at the bottom thereof of 140-190° C., and an operating pressure of 0.25-0.5 MPaG; the light hydrocarbon-light gasoline separation column has an operating temperature of 55-80° C., and an operating pressure of 1.0-1.35 MPaG; the heavy gasoline has an initial boiling point of 60-85° C., and the light gasoline has a dry point of 65-90° C.

In the present invention, in order to meet requirements for the recovery of related products, it is necessary to remove impurities before a next step of separation. The impurity removal mainly includes amine washing for removal of $H_2S$ and alkali washing for removal of mercaptans. Desulfurization and sweetening of a gas phase conducted under a high pressure produces better effects, and to conduct the desulfurization and sweetening requires a desulfurization device of a relatively small volume; therefore, in the present invention, the compressed gas phase and the pressurized liquid phase in the gas-liquid separation tank II are mixed first to reach gas-liquid equilibrium and then subjected to further separation to obtain a gas phase and a liquid phase, and the gas phase and the liquid phase are then subjected to impurity removal, respectively. Preferably, the gas-liquid separation tank II has an operating temperature of 35-45° C., and an operating pressure of 2.3-2.9 MPaG. Due to the low content of heavy hydrocarbons in the gas phase separated out, the amounts of heavy hydrocarbons condensed into the amine solution during desulfurization are also small, which effectively avoids foam entrainment of the desulfurization device caused by foaming of the amine solution and thus avoids effects on smooth operation of the device.

In the present invention, in order to meet requirements for the recovery of related products, preferably, a composite amine solution solvent (i.e., a modified solvent based on MDEA) is used in the amine washing for removal of $H_2S$ to simultaneously remove $H_2S$ and $CO_2$. $H_2S$ can be removed to a content of less than 10 ppmv, and $CO_2$ removal efficiency can be up to 90-95 wt %. The content of $CO_2$ in the stream within the alkali washing sweetening reactor is thus effectively decreased, and further the consumption of alkali liquor is decreased.

According to the present invention, preferably, the rich gas desulfurizing column has an operating temperature of 35-45° C., and an operating pressure of 2.2-2.8 MPaG; the rich gas sweetening column has an operating temperature of 35-45° C., and an operating pressure of 2.2-2.8 MPaG; the liquid hydrocarbon desulfurizing column has an operating temperature of 35-45° C., and an operating pressure of 3.0-3.5 MPaG.

In the present invention, the impurity-removed gas phase components and the impurity-removed liquid phase components need to be cooled before being sent into the feeding tank. The cooled liquid phase and the cooled and compressed gas phase are both sent to the feeding tank. Preferably, the feeding tank has an operating temperature of 5-25° C. and an operating pressure of 2.1-2.8 MPaG.

According to the present invention, preferably, the absorption column has an operating temperature of 5-25° C., and an operating pressure of 2.1-2.7 MPaG. In the present invention, the mixed $C_4$ absorbent used in the absorption column is from the bottom of the depropanizer, and is a self-balanced $C_4$ component in the system and does not need to be introduced from outside the system.

According to the present invention, preferably, the separation in step (10) is performed according to one of the following three processes.

Process I: The separation includes the following steps in sequence.

Demethanization: The liquid phase from the bottom of the feeding tank is subjected to removal of methane and simultaneously to removal of small part of $C_2$ and $C_{2+}$ components in a demethanizer. A resulting gas phase at a top of the demethanizer is sent to the cooling unit, and a resulting liquid phase at a bottom of the demethanizer is sent to a deethanizer.

Deethanization: The liquid phase from the bottom of the demethanizer is subjected to separation in the deethanizer to obtain a $C_2$ component by using propane as an absorbent. A mixed $C_2$ component at a top of the deethanizer obtained from the separation is optionally subjected to impurity removal, and then collected as a mixed $C_2$ product, and resulting liquid-phase components of $C_3$ and $C_{3+}$ at a bottom of the deethanizer are sent to a depropanizer.

Depropanization: The liquid-phase components from the bottom of the deethanizer are subjected to further separation in the depropanizer. A $C_3$ component obtained from the separation is collected from an upper portion of the depropanizer. At least part of resulting components at a bottom of the depropanizer is sent as a mixed $C_4$ absorbent to the absorption column, and the rest is collected as a mixed $C_4$ product.

Preferably, the separation further includes the following step.

Propylene rectification: The $C_3$ component from the upper portion of the depropanizer is subjected to further rectification in a propylene rectifying column. A resulting gas phase at a top of the propylene rectifying column is cooled and then collected as a propylene product. At least part of a resulting liquid phase at a bottom of the propylene rectifying column is collected as a propane product, and the rest is heated and then sent as a propane absorbent to the deethanizer.

Process II: The separation includes the following steps in sequence.

Demethanization: The liquid phase from the bottom of the feeding tank is subjected to removal of methane and simultaneously to removal of small part of $C_2$ and $C_{2+}$ components in a demethanizer. A resulting gas phase at a top of the demethanizer is sent to the cooling unit, and a resulting liquid phase at a bottom of the demethanizer is sent to a deethanizer.

Deethanization: The liquid phase from the bottom of the demethanizer is subjected to separation in the deethanizer to obtain a $C_2$ component by using a mixed $C_4$ as an absorbent. A mixed $C_2$ component at a top of the deethanizer obtained from the separation is optionally subjected to impurity removal, and then collected as a mixed $C_2$ product, and resulting liquid-phase components of $C_3$ and $C_{3+}$ at a bottom of the deethanizer are sent to a depropanizer.

Depropanization: The liquid-phase components from the bottom of the deethanizer are subjected to further separation in the depropanizer. A $C_3$ component obtained from the separation is collected from an upper portion of the depropanizer; at least part of resulting components at a bottom of the depropanizer is sent as a mixed $C_4$ absorbent to the absorption column and the deethanizer, and the rest is collected as a mixed $C_4$ product.

More preferably, the separation further includes the following step.

Propylene rectification: The $C_3$ component from the upper portion of the depropanizer is subjected to further rectification in a propylene rectifying column. A resulting gas phase at a top of the propylene rectifying column is cooled and then collected as a propylene product, and a resulting liquid phase at a bottom of the propylene rectifying column is collected as a propane product.

Process III: The separation includes the following steps in sequence.

Demethanization: The liquid phase from the bottom of the feeding tank is subjected to removal of methane and simultaneously to removal of small part of $C_2$ and $C_{2+}$ components in a demethanizer. A resulting gas phase at a top of the demethanizer is sent to the cooling unit, and a resulting liquid phase at a bottom of the demethanizer is sent to a depropanizer.

Depropanization: The liquid phase from the bottom of the demethanizer is subjected to further separation in the depropanizer; $C_3$ and $C_{3-}$ components obtained from the separation are collected from an upper portion of the depropanizer, optionally dried, and then sent to a deethanizer. At least part of resulting components at a bottom of the depropanizer is sent as a mixed $C_4$ absorbent to the absorption column, and the rest is collected as a mixed $C_4$ product.

Deethanization: The gas phase from the upper portion of the depropanizer is subjected to further separation in the deethanizer by using propane as an absorbent. A mixed $C_2$ component at a top of the deethanizer obtained from the separation is optionally subjected to impurity removal, and then collected as a mixed $C_2$ product, and a resulting liquid phase at a bottom of the deethanizer is collected as a mixed $C_3$ component.

More preferably, the separation further includes the following step.

Propylene rectification: The mixed $C_3$ component from the bottom of the deethanizer is subjected to further rectification in a propylene rectifying column. A resulting gas phase at a top of the propylene rectifying column is cooled and then collected as a propylene product. At least part of a liquid phase at a bottom of the propylene rectifying column is collected as a propane product, and the rest is sent as a propane absorbent to the deethanizer.

When a propane absorbent or a mixed $C_4$ absorbent is used in the deethanizer for separation for the $C_2$ component, the $C_2$ component separated out basically entrains no propylene, and contains only 15-18 mol % propane or 10-13 mol % $C_4$. At this time, a minimum temperature at the top of the deethanizer is only 15° C., and a drying device is not required as conventional lithium bromide refrigeration can meet the requirement. Because the content of propylene in the $C_2$ component is greatly reduced, the $C_2$ component can be directly sent for ethylbenzene production without the need for an additional impurity removal device. Preferably, the deethanizer has an operating temperature of 15-30° C. and an operating pressure of 2.6-3.2 MPaG at the top thereof. The propane absorbent and/or the mixed $C_4$ absorbent is from the self-balanced propane and/or mixed $C_4$ components in the system, and do not need to be introduced from outside the system.

In the present invention, the separated mixed $C_3$ component can be further rectified to obtain a propylene product and a propane product. Preferably, the propylene rectifying column has an operating temperature of 45-60° C., and an operating pressure of 1.8-2.0 MPaG.

In order to further recover the mixed $C_4$ absorbent entrained in the stream at the top of the absorption column, preferably, the method further includes the following step.

(11) Recovery of absorbent: In an absorbent recovery column, the heavy gasoline product collected in step (2) is used as an absorbent to absorb $C_4$ and $C_{4+}$ components present in the gas phase from the top of the absorption column, and to simultaneously absorb small amounts of $C_2/C_3$ components. A resulting gas phase at a top of the absorbent recovery column is collected as a dry gas, and a resulting liquid phase at a bottom of the absorbent recovery column is returned to the light-heavy gasoline separation column. More preferably, the absorbent recovery column has an operating temperature of 15-40° C., and an operating pressure of 2.1-2.7 MPaG.

The present invention, in another aspect, provides a device for recovery of an oil gas. The device includes: an oil gas feeding pipeline, a gas-liquid separation tank I, a compressor I, a light-heavy gasoline separation column, a compressor II, a light hydrocarbon-light gasoline separation column, a compressor III, a cooling unit II, a gas-liquid separation tank II, a rich gas desulfurizing column, a rich gas sweetening column, a liquid hydrocarbon desulfurizing column, a liquid hydrocarbon sweetening reactor, a cooling unit III, a feeding tank, an absorption column, and a separation unit.

The oil gas feeding pipeline is connected with an inlet of the gas-liquid separation tank I. The gas-liquid separation tank I is connected at a top thereof sequentially with the compressor I and the light-heavy gasoline separation column, and is connected at a bottom thereof with the light-heavy gasoline separation column.

The light-heavy gasoline separation column is provided at a top thereof with a reflux tank I. The reflux tank I is connected at a top thereof sequentially with the compressor II and the light hydrocarbon-light gasoline separation column, and is connected at a bottom thereof first with a booster pump first and then with the light hydrocarbon-light gasoline separation column. The light-heavy gasoline separation column is provided at a bottom thereof with a heavy gasoline collecting pipeline.

The light hydrocarbon-light gasoline separation column is provided at a top thereof with a reflux tank II. The reflux tank II is connected at a top thereof sequentially with the compressor III, the cooling unit II, and the gas-liquid separation tank II, and is connected at a bottom thereof first with a booster pump and then with the gas-liquid separation tank II.

The gas-liquid separation tank II is connected at a top thereof with the rich gas desulfurizing column, the rich gas sweetening column, and the cooling unit III, and is connected at a bottom thereof with the liquid hydrocarbon desulfurizing column, the liquid hydrocarbon sweetening reactor, and the cooling unit III.

The rich gas desulfurizing column is provided on an upper portion thereof with a lean amine solution feeding pipeline, and the rich gas sweetening column is provided on an upper portion thereof with an alkali liquor feeding pipeline.

The cooling unit III is connected with the feeding tank.

The feeding tank is connected at a top thereof with the absorption column, and is connected at a bottom thereof with the separation unit.

The absorption column is connected at a top thereof with a downstream device, is connected at a bottom thereof with the cooling unit III, and is provided on an upper portion thereof with a mixed $C_4$ absorbent feeding pipeline.

The separation unit includes: a demethanizer, a deethanizer, a depropanizer, and an optional propylene rectifying column. The demethanizer is connected at a top thereof with the cooling unit III. The deethanizer is provided at a top thereof with a mixed $C_2$ collecting pipeline optionally provided thereon with an impurity treatment unit. The deethanizer is provided on an upper portion thereof with a propane or mixed $C_4$ absorbent feeding pipeline. The depropanizer is provided at a bottom thereof with a mixed $C_4$ product collecting pipeline. The mixed $C_4$ product collecting pipeline is divided into two branches, one of which serves as the mixed $C_4$ absorbent feeding pipeline.

In the present invention, further separation for $C_4$ and $C_{4-}$ components is performed in the separation unit. Preferably, in the separation unit, the demethanizer is connected at a top thereof with the cooling unit III, and is connected at a bottom thereof with the deethanizer; the deethanizer is provided at a top thereof with the mixed $C_2$ collecting pipeline optionally provided thereon with the impurity treatment unit, is connected at a bottom thereof with the depropanizer, and is provided on an upper portion thereof with a propane absorbent feeding pipeline; the depropanizer is provided on an upper portion thereof with a mixed $C_3$ collecting pipeline optionally connected with a propylene rectifying column, and is provided at a bottom thereof with the mixed $C_4$ product collecting pipeline, the mixed $C_4$ product collecting pipeline being divided into two branches, one of which serves as a mixed $C_4$ absorbent feeding pipeline. Preferably, the propylene rectifying column is provided at a top thereof with a propylene product collecting pipeline, and is provided at a bottom thereof with a propane product collecting pipeline, the propane product collecting pipeline being divided into two branches, one of which serves as the propane absorbent feeding pipeline. Or, preferably, the demethanizer is connected at a top thereof with the cooling unit III, and is connected at a bottom thereof with the deethanizer; the deethanizer is provided at a top thereof with a mixed $C_2$ collecting pipeline optionally provided thereon with an impurity treatment unit, is connected at a bottom thereof with the depropanizer, and is provided on an upper portion thereof with a mixed $C_4$ absorbent feeding pipeline; the depropanizer is provided on an upper portion thereof with a mixed $C_3$ collecting pipeline optionally connected with a propylene rectifying column, and is provided at a bottom thereof with a mixed $C_4$ product collecting pipeline, the mixed $C_4$ product collecting pipeline being divided into two branches, one of which serves as the mixed $C_4$ absorbent feeding pipeline and is connected with the absorption column and the deethanizer, respectively. More preferably, the propylene rectifying column is provided at a top thereof with a propylene product collecting pipeline, and is provided at a bottom thereof with a propane product collecting pipeline. Or, preferably, the demethanizer is connected at a top thereof with the cooling unit III, and is connected at a bottom thereof with the depropanizer; the depropanizer is connected on an upper portion thereof with an optional drying unit and then with the deethanizer, and is provided at a bottom thereof with a mixed $C_4$ product collecting pipeline, the mixed $C_4$ product collecting pipeline being divided into two branches, one of which serves as the mixed $C_4$ absorbent feeding pipeline; the deethanizer is provided on a top thereof with a mixed $C_2$ collecting pipeline optionally provided thereon with an impurity treatment unit, is provided at a bottom thereof with a mixed $C_3$ collecting pipeline optionally connected with a propylene rectifying column, and is provided on an upper portion thereof with a propane absorbent feeding pipeline. More preferably, the propylene rectifying column is provided at a top thereof with a propylene product collecting pipeline, and is provided at a bottom thereof with a propane product collecting pipeline, the propane product collecting pipeline being divided into two branches, one of which serves as the propane absorbent feeding pipeline.

According to the present invention, preferably, the downstream device further includes an absorbent recovery column. The absorbent recovery column is provided on a top thereof with a dry gas collecting pipeline, is connected at a bottom thereof with a light-heavy gasoline separation column, and is provided on an upper portion thereof with a heavy gasoline absorbent feeding pipeline. The heavy gasoline collecting pipeline of the light-heavy gasoline separation column is divided into two branches, one of which serves as the heavy gasoline absorbent feeding pipeline.

In the present invention, in order to maintain a uniform operating temperature throughout the absorption column and ensure absorption effects, the absorption column can be provided with two to five middle-stage refluxes. Besides, it is not necessary to provide a condenser at the top of the absorption column and to provide a reboiler at the bottom of the absorption column. The gas phase from the feeding tank is fed from the bottom of the absorption column, and the absorbent is fed from the upper portion of the absorption column.

According to the present invention, preferably, the demethanizer is not provided at the top thereof with a condenser, and is provided at the bottom thereof with a reboiler. The liquid phase from the feeding tank is fed from the top of the demethanizer. The device does not include a dehydration device.

The present invention will be described in detail below by way of examples. The protection scope of the present invention, however, is not limited to the following description.

In the context of the present invention, i-$C_4H_{10}$ refers to isobutane; n-$C_4H_{10}$ refers to n-butane; i-$C_4H_8$ refers to isobutene; n-$C_4H_8$ refers to n-butene; t-$C_4H_8$ refers to trans-butene; c-$C_4H_8$ refers to cis-butene; PC28C refers to all $C_5$ and $C_{5+}$ hydrocarbon components; RSH refers to a mercaptan, where R refers to hydrocarbyl, such as —$CH_3$, —$C_2H_5$, —$C_3H_7$, etc.

In the following examples, properties of a raw oil gas are shown in Table 1, and properties of $C_{5+}$ components in the oil gas are shown in Table 2.

TABLE 1

| Items | Raw material |
|---|---|
| Temperature, ° C. | 40 |
| Pressure, MPaG | 0.05 |
| Molar vapor fraction | 0.6446 |
| Flow rate, kg/h | 203666.3 |

| Components | Mass fraction |
|---|---|
| $H_2$ | 0.0020 |
| CO | 0.0005 |
| $CO_2$ | 0.0022 |
| $O_2$ | 0.0006 |
| $N_2$ | 0.0043 |
| $CH_4$ | 0.0129 |
| $C_2H_6$ | 0.0122 |
| $C_2H_4$ | 0.0126 |
| $C_3H_6$ | 0.0917 |
| $C_3H_8$ | 0.0238 |
| i-$C_4H_{10}$ | 0.0621 |
| n-$C_4H_{10}$ | 0.0136 |
| i-$C_4H_8$ | 0.0241 |
| n-$C_4H_8$ | 0.0134 |
| t-$C_4H_8$ | 0.0191 |
| c-$C_4H_8$ | 0.0141 |
| $H_2S$ | 0.0034 |
| $C_{5+}$ | 0.6874 |
| Mercaptan | 50 ppmw |
| Total | 1.000 |

TABLE 2

| Items | Numerical values |
|---|---|
| Density (20° C.), g/cm³ | 0.753 |

| Curve of D86, v % | Temperature, ° C. |
|---|---|
| 0 | 35.0 |
| 5 | 44.1 |
| 10 | 52.0 |
| 30 | 73.0 |
| 50 | 95.0 |
| 70 | 128.0 |
| 90 | 177.0 |
| 95 | 188.7 |
| 100 | 200.0 |

Example 1

Referring to FIG. 1, a device for treating an oil gas in this example comprises: a light hydrocarbon feeding pipeline, a gas-liquid separation tank 11, a compressor I 2, a compressor II 3, a debutanizer 4, a rich gas desulfurizing column 5, a rich gas sweetening column 6, a cooling unit I 7, a compressor III 8, a cooling unit II 9, a cooling unit III 10, a feeding tank 11, an absorption column 12, a demethanizer 13, a deethanizer 14, a depropanizer 15, a propylene rectifying column 16, an absorbent recovery column 17.

The light hydrocarbon feeding pipeline is connected with an inlet of the gas-liquid separation tank I 1. The gas-liquid separation tank I 1 is connected at a top thereof sequentially with the compressor I 2, the compressor II 3, and the debutanizer 4, and is connected at a bottom thereof with the debutanizer 4.

The debutanizer 4 is connected at a top thereof sequentially with the rich gas desulfurizing column 5, the rich gas sweetening column 6, the cooling unit I 7, the compressor III 8, the cooling unit II 9, the cooling unit III 10, and the feeding tank 11, and is provided at a bottom thereof with a stable gasoline collecting pipeline.

The cooling unit I 7 is directly connected with the cooling unit III 10 through a pipeline.

The feeding tank 11 is connected at a top thereof with the absorption column 12, and is connected at a bottom thereof with the demethanizer 13.

The absorption column 12 is connected at a top thereof with the absorbent recovery column 17, is connected at a bottom thereof with the cooling unit III 10, and is provided on an upper portion thereof with a mixed $C_4/C_5$ absorbent feeding pipeline.

The absorbent recovery column 17 is provided at a top thereof with a dry gas collecting pipeline, is connected at a bottom thereof with the debutanizer 4, and is provided on an upper portion thereof with a stable gasoline absorbent feeding pipeline. The stable gasoline absorbent feeding pipeline is connected with the stable gasoline collecting pipeline of the debutanizer 4.

The demethanizer 13 is connected at a top thereof with the cooling unit III 10, and is connected at a bottom thereof with the deethanizer 14.

The deethanizer 14 is provided at a top thereof with a mixed $C_2$ collecting pipeline, and is connected at a bottom thereof with the depropanizer 15.

The depropanizer 15 is connected at a top thereof with the propylene rectifying column 16, and is provided at a bottom thereof with a mixed $C_4/C_5$ product collecting pipeline connected with the mixed $C_4/C_5$ absorbent feeding pipeline.

The propylene rectifying column 16 is provided at a top thereof with a propylene product collecting pipeline, and is provided at a bottom thereof with a propane product collecting pipeline.

The above device was used for treating an oil gas. A process flow of the treatment is shown in FIG. 1.

(1) Gas-liquid separation: A gas phase raw material S-1 from a top of a catalytic cracking fractionator was condensed and cooled and then sent to the gas-liquid separation tank I 1 for gas-liquid separation (components and properties of the raw material cooled at the top of the fractionator are shown in Table 1; properties of $C_5$ and $C_{5+}$ components in the raw material cooled at the top of the fractionator are shown in Table 2). A resulting liquid phase at the bottom of the gas-liquid separation tank I 1 was sent to the debutanizer 4, and a resulting gas phase was compressed and sent to the debutanizer 4.

(2) Debutanization: The gas phase and the liquid phase from step (1) entered into the debutanizer 4. A resulting gas phase at the top of the debutanizer 4 was distilled off from the top of the debutanizer 4, treated by amine washing and alkali washing, and then sent to the cooling unit, and at least part of a resulting liquid phase at the bottom of the debutanizer 4 was collected as a stable gasoline product. The debutanizer 4 had an operating temperature of 40-70° C., and an operating pressure of 1.0-1.6 MPaG. The gas phase at the top of the debutanizer 4 had a content of the $C_5$ and $C_{5+}$ components of less than 5 wt %, and the stable gasoline S-10 at the bottom of the debutanizer 4 had a dry point of less than 204° C.

(3) Cooling: Light hydrocarbons having been treated by the amine washing and the alkali washing were cooled preliminarily in the cooling unit. A resulting cooled liquid phase was pressurized and then sent to the cooling unit III 10, and a resulting cooled gas phase was compressed, re-cooled, and then sent to the cooling unit III 10.

(4) Post-cooling: The gas phase and the liquid phase from step (3) were preliminarily mixed and cooled in the cooling unit III 10 and then sent to the feeding tank I 1 as a mixed stream.

(5) Feeding: The mixed stream from the cooling unit III 10 was mixed and pre-absorbed to reach gas-liquid equilibrium in the feeding tank I 1. A resulting gas phase at the top of the feeding tank I 1 was sent to the absorption column 12, and a resulting liquid phase at the bottom of the feeding tank I 1 was sent to the demethanizer 13. The feeding tank I 1 had an operating temperature of 5-25° C., and an operating pressure of 2.0-3.5 MPaG.

(6) Absorption: In the absorption column, a mixed $C_4/C_5$ was used as an absorbent to absorb $C_2$ and $C_{2+}$ components present in the gas phase from the top of the feeding tank I 1, and to simultaneously co-absorb part of methane. A resulting gas phase at the top of the absorption column was sent to the absorbent recovery column for further recovery of the absorbent, and a resulting liquid phase at the bottom of the absorption column was sent to the cooling unit III 10. The absorption column 12 had an operating pressure of 2.0-3.5 MPaG, and an overall operating temperature of 5-30° C. The absorbent in the absorption column 12 was from a self-balanced mixed $C_4/C_5$ component in the system and did not need to be introduced from outside the system.

(7) Demethanization: The liquid phase from the bottom of the feeding tank I 1 was subjected to removal of methane and simultaneously to removal of small part of $C_2$ and $C_{2+}$ components in the demethanizer 13. A resulting gas phase at the top of the demethanizer 13 was sent to the cooling unit III 10, and a resulting liquid phase at a bottom of the demethanizer 13 was sent to the deethanizer 14.

(8) Deethanization: The liquid phase from the bottom of the demethanizer 13 was subjected to separation in the deethanizer 14 to obtain a $C_2$ component. A mixed $C_2$ component obtained from the separation was collected from the top of the deethanizer 14 as a mixed $C_2$ product S-12, and resulting liquid-phase components of $C_3$ and $C_{3+}$ at a bottom of the deethanizer 14 were sent to the depropanizer 15. The deethanizer 14 had an operating temperature of 5-20° C. and an operating pressure of 2.5-3.8 MPaG at the top thereof. The mixed $C_2$ product S-12 at the top of the deethanizer 14 contained 10-25 vol % of propylene.

(9) Depropanization: The liquid-phase components from the bottom of the deethanizer 14 were subjected to further separation in the depropanizer 15. A $C_3$ component obtained from the separation was collected from the top of the depropanizer 15 and sent to the propylene rectifying column 16 for further rectification. At least part of resulting components at the bottom of the depropanizer 15 was sent as a mixed $C_4/C_5$ absorbent to the absorption column 12, and the rest was collected as a mixed $C_4/C_5$ product.

(10) Propylene rectification: The gas phase from the top of the depropanizer 15 was subjected to further rectification in the propylene rectifying column 16. A resulting gas phase at the top of the propylene rectifying column 16 was collected as a propylene product S-13, and a resulting liquid phase at the bottom of the propylene rectifying column 16 was collected as a propane product S-14.

column included: an operating temperature of 42-55° C. and an operating pressure of 1.6-2.0 MPaG at the top thereof, and an operating temperature of 55-63° C. at the bottom thereof.

The light hydrocarbons in a catalytic cracking reaction were separated by the above method. Composition and properties of the products separated out are shown in Table 3, and properties of the stable gasoline are shown in Table 4.

TABLE 3

|  | dry gas | mixed $C_2$ | propylene | propane | mixed $C_4$ | stable gasoline |
|---|---|---|---|---|---|---|
| Temperature, ° C. | 17 | 15 | 46 | 58 | 40 | 117 |
| Pressure, MPaG | 2.63 | 2.90 | 1.80 | 1.86 | 1.82 | 1.20 |
| Molar vapor fraction | 1 | 1 | 0 | 0 | 0 | 0 |
| Flow rate, kg/h | 4611.2 | 7521.7 | 17300.0 | 4932.6 | 28398.9 | 140801.7 |
| | | | Molar fraction | | | |
| $H_2$ | 0.4944 | | | | | |
| CO | 0.0083 | | | | | |
| $CO_2$ | 0.0020 | 0.0419 | | | | |
| $O_2$ | 0.0099 | | | | | |
| $N_2$ | 0.0757 | | | | | |
| $CH_4$ | 0.3920 | 0.0085 | | | | |
| $C_2H_6$ | 0 | 0.3735 | 0.0016 | | | |
| $C_2H_4$ | 0.0029 | 0.4139 | 0 | | | |
| $C_3H_6$ | 0 | 0.1422 | 0.9960 | 0.0153 | 0.0023 | |
| $C_3H_8$ | 0 | 0.0197 | 0.0024 | 0.9318 | 0.0043 | |
| $i-C_4H_{10}$ | 0.0003 | 0.0002 | | 0.0368 | 0.4225 | 0.0021 |
| $n-C_4H_{10}$ | 0.0002 | 0.0000 | | 0.0008 | 0.0879 | 0.0025 |
| $i-C_4H_8$ | 0.0002 | | | 0.0095 | 0.1684 | 0.0017 |
| $n-C_4H_8$ | 0.0001 | 0.0000 | | 0.0044 | 0.0931 | 0.0011 |
| $t-C_4H_8$ | 0.0003 | 0.0000 | | 0.0011 | 0.1271 | 0.0039 |
| $c-C_4H_8$ | 0.0004 | 0.0000 | | 0.0004 | 0.0876 | 0.0050 |
| $C_5+$ | 0.0134 | 0.0000 | | | 0.0070 | 0.9837 |
| Total | 1.00 | 1.00 | 1.00 | 1.00 | 1.00 | 1.00 |

(11) Recovery of absorbent: In the absorbent recovery column 17, at least part of the stable gasoline product S-10 collected in step (2) was used as an absorbent to absorb $C_4$ and $C_{4+}$ components present in the gas phase from the top of the absorption column, and simultaneously to absorb small amounts of $C_2/C_3$ components. A resulting gas phase at the top of the absorbent recovery column 17 was collected as a dry gas S-11, and a resulting liquid phase at the bottom of the absorbent recovery column 17 was sent to the debutanizer 4. The absorbent recovery column 17 had an operating temperature of 5-50° C., and an operating pressure of 1.9-3.4 MPaG.

In Example 1, the amine washing was operated at conditions comprising: using an aqueous solution of 30 wt % MDEA as amine solution, an operating temperature of 43° C., and an operating pressure of 1.2 MPaG. The alkali washing was operated at conditions comprising: using an aqueous solution of 10 wt % NaOH as alkali liquor, an operating temperature of 43° C., and an operating pressure of 1.15 MPaG. Conditions in the demethanizer included: an operating temperature of 5-25° C. and an operating pressure of 2.1-2.9 MPaG at the top thereof, and an operating temperature of 70-95° C. at the bottom thereof. Conditions in the depropanizer included: an operating temperature of 42-55° C. and an operating pressure of 1.6-1.9 MPaG at the bottom thereof, and an operating temperature of 95-120° C. at the bottom thereof. Conditions in the propylene rectifying

TABLE 4

| Items | Numerical values |
|---|---|
| Density (20° C.), g/cm³ | 0.753 |
| Content of $C_4$ component, vol % | 1.63 |
| Reid Vapor Pressure, kPa | 65.8 |
| Curve of D86, v % | Temperature, ° C. |
| 0 | 38.7 |
| 5 | 46.1 |
| 10 | 49.1 |
| 30 | 72.0 |
| 50 | 94.4 |
| 70 | 127.6 |
| 90 | 176.9 |
| 95 | 187.3 |
| 100 | 197.7 |

It can be seen from the data in the above tables that the present invention is simple in its process and operated at moderate conditions, and consumes less energy. The separation for and recovery of the light hydrocarbons in the catalytic cracking process can be accomplished with relatively few devices. The total recovery rate of the $C_2$ component is more than 98 wt %, and the recovery rate of the $C_3$ component is more than 99 wt %. The recovered $C_2$ component has a content of methane of not more than 1 vol %, and the recovered $C_3$ component has a content of ethane of not more than 2000 ppmv. Besides, the recovered $C_3$ component is further separated into propylene and propane. The recovery rates of propylene and propane are both more than 99 wt %. The recovered dry gas contains only relatively small amounts of impurities and has a content of $C_2$ and $C_{2+}$ components of not more than 2 vol %, and the purity of hydrogen is more than 40 mol %. The collected stable gasoline has a dry point of 197.7° C., and has a content of the $C_4$ component of only 1.63 vol %, and can meet quality requirements for a gasoline product after being treated by simple desulfurization.

Example 2

A device for desulfurization of an oil gas includes: an oil gas feeding pipeline, a gas-liquid separation tank 1 1, a compressor I 2, a compressor II 3, a debutanizer 4, a rich gas desulfurizing column 5, a rich gas sweetening column 6, a rich gas water washing tank 6e, and a solvent regeneration column 5c.

The oil gas feeding pipeline is connected with an inlet of the gas-liquid separation tank I 1. The gas-liquid separation tank I 1 is connected at a top thereof sequentially with the compressor I 2, the compressor II 3, and the debutanizer 4, and is connected at a bottom thereof with the debutanizer 4. A liquid phase collecting pipeline between stages of the compressor I is connected with the debutanizer 4.

The debutanizer 4 is provided at a top thereof with a reflux tank. The reflux tank is connected at a top thereof with the rich gas desulfurizing column 5, and is connected at a bottom thereof with the debutanizer 4. The debutanizer 4 is provided at a bottom thereof with a stable gasoline collecting pipeline.

The rich gas desulfurizing column 5 is provided on an upper portion thereof with a lean amine solution feeding pipeline which is optionally provided thereon with a lean amine solution cooling unit 5d. The rich gas desulfurizing column 5 is connected at a top thereof with the rich gas sweetening column 6, and is provided at a bottom thereof with a rich amine solution collecting pipeline. The rich amine solution collecting pipeline is connected with the solvent regeneration column 5c. The solvent regeneration column 5c is provided at a bottom thereof with a lean amine solution feeding pipeline, and is provided at a top thereof with an acidic gas collecting pipeline.

The rich gas sweetening column 6 is provided on an upper portion thereof with an alkali liquor feeding pipeline, is connected at a top thereof with the rich gas water washing tank 6e, and is provided at a bottom thereof with a downstream regeneration device.

The rich gas water washing tank 6e is provided at a top thereof with a light hydrocarbon collecting pipeline, and is connected at a bottom thereof first with a rich gas water washing circulating pump 6b and then with a water washing used water heating unit 6c and a water washing discharge pipeline, respectively. The water washing used water heating unit 6e is connected with an upper portion of the rich gas water washing tank 6e.

Figure 2:
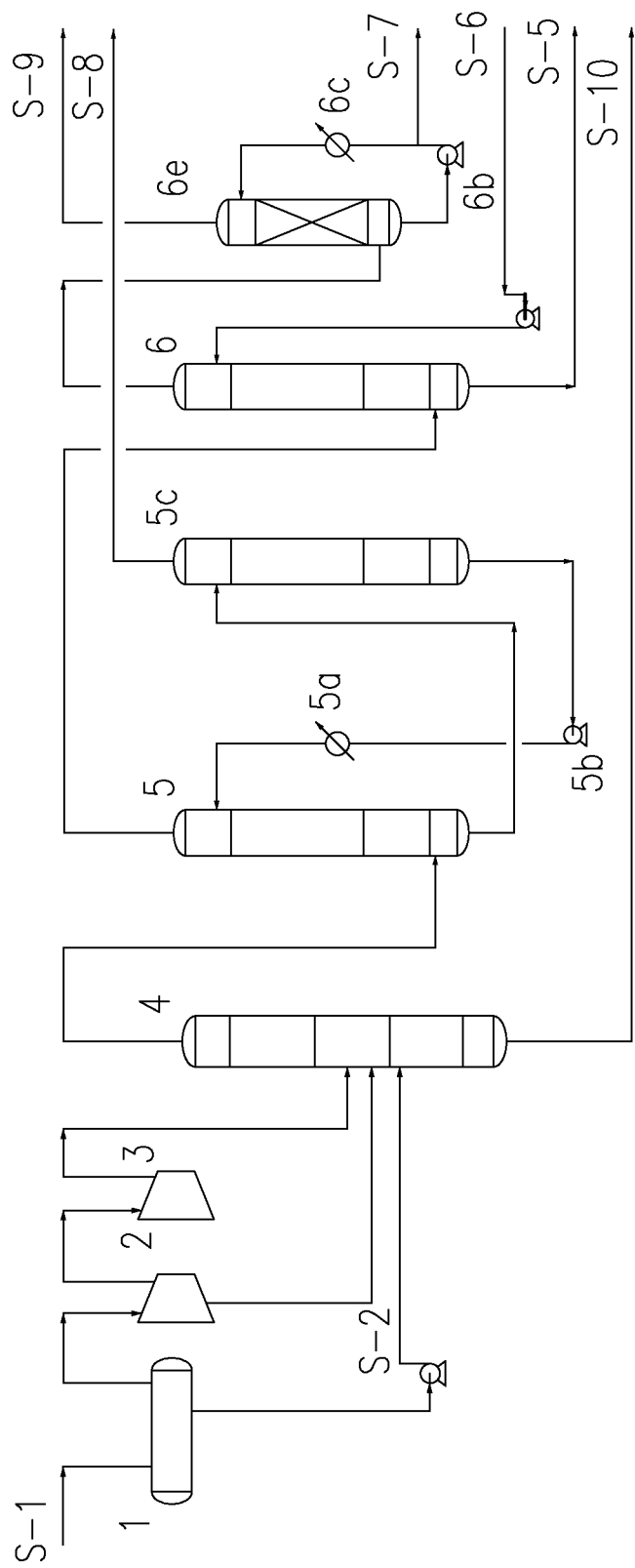
FIG. 2 is a flow diagram of a desulfurization process in oil gas treatment according to Example 2 of the present invention.

Process for desulfurization of oil gas:

The above-described device was used for desulfurization of an oil gas. A process flow is shown in FIG. 2.

(1) Gas-liquid separation: an oil gas S-1 from an upstream device was condensed and cooled and then sent to the gas-liquid separation tank I 1 for gas-liquid separation. A resulting liquid phase at a bottom of the gas-liquid separation tank 1 1 was pressurized and then sent to the debutanizer, and a resulting gas phase at a top of the gas-liquid separation tank I 1 was compressed by a compressor and then sent to the debutanizer 4. A liquid phase between stages of the compressor I was sent to the debutanizer 4.

(2) Debutanization: The gas phase and the liquid phase from step (1) entered into the debutanizer 4. The gas phase distilled off at a top of the debutanizer 4 was condensed and then sent to a reflux tank at the top of the debutanizer 4 for separation to obtain a rich gas and a liquid phase. The rich gas was subjected further to impurity removal, and the liquid phase was returned to the debutanizer 4. At least part of a resulting liquid phase at a bottom of the debutanizer 4 was collected as a stable gasoline product S-10. The debutanizer had an operating temperature of 45-65° C. and an operating pressure of 1.0-1.5 MPaG at a top thereof, and had an operating temperature of 150-200° C. at a bottom thereof. The reflux tank had a temperature of 35-50° C.

(3) Impurity removal: The rich gas from the top of the debutanizer 4 was subjected sequentially to removal of $H_2S$ and $CO_2$ in the rich gas desulfurizing column 5 with a lean amine solution S-4 (an aqueous solution of 30 wt % MDEA) as an absorbent, to removal of mercaptans in the rich gas sweetening column 6 with an alkali liquor S-6 (an aqueous solution of 10 wt % NaOH) as an absorbent, and to water washing in the rich gas water washing tank 6e to reach acid-base equilibrium. The impurity-removed rich gas was collected from a top of the rich gas water washing tank 6e. The rich gas desulfurizing column 5 had an operating temperature of 35-50° C., and an operating pressure of 1.0-1.5 MPaG. The rich gas sweetening column 6 had an operating temperature of 35-50° C., and an operating pressure of 0.9-1.4 MPaG. The rich gas washing tank 6e had an operating temperature of 35-50° C., and an operating pressure of 0.9-1.4 MPaG. The lean amine solution as the absorbent had a temperature 3-8° C. higher than a temperature of the rich gas. Water washing used water in the water washing tank had a temperature 3-8° C. higher than the temperature of the rich gas.

The rich gas was removed of impurities by the above method. Properties of the impurity-removed rich gas are shown in Table 5.

TABLE 5

| | Rich gas | |
|---|---|---|
| | Before impurity removal | After impurity removal |
| $CO_2$ | 6500 ppmw | 200 ppmw |
| $H_2S$ | 1650 ppmw | 15 ppmw |
| mercaptans | 210 ppmw | 20 ppmw |

As can be seen from the above, in the present invention, after being subjected to desulfurization, sweetening, and water washing, the rich gas has a content of $H_2S$ of 15 ppmw, and a content of mercaptans of not more than 20 ppmw; $CO_2$ removal rate is up to 96 wt %. Sulfur and mercaptan removal rate is thus improved. Besides, the removal of hydrogen sulfide and carbon dioxide is completed in a same column, which simplifies the process and saves investment in equipment.

Example 3

The rich gas obtained after the impurity removal in Example 2 was subjected to separation for light hydrocarbons. A separation unit includes: a cooling unit I 7, a gas-liquid separation tank II 7a, a compressor III 8, a cooling unit II 9, a cooling unit III 10, a feeding tank 11, an absorption column 12, a demethanizer 13, a depropanizer 15, a deethanizer 14, a propylene rectifying column 16, and an absorbent recovery column 17.

A light hydrocarbon collecting pipeline is connected sequentially the cooling unit I 7 and the gas-liquid separation tank II 7a. The gas-liquid separation tank II 7a is sequentially connected at a top thereof with the compressor III 8, the cooling unit II 9, the cooling unit III 10, and the feeding tank 11, and is connected at a bottom thereof sequentially with the cooling unit III 10 and the feeding tank 11.

The feeding tank 11 is connected at a top thereof with the absorption column 12, and is connected at a bottom thereof with the demethanizer 13.

The absorption column 12 is connected at a top thereof with the absorbent recovery column 17, is connected at a bottom thereof with the cooling unit III 10, and is provided on an upper portion thereof with a mixed $C_4$ absorbent feeding pipeline.

The absorbent recovery column 17 is provided at a top thereof with a dry gas collecting pipeline, is connected at a bottom thereof with the debutanizer 4, and is provided on an upper portion thereof with a stable gasoline absorbent feeding pipeline. A stable gasoline collecting pipeline of the debutanizer 4 is divided into two branches, one of which serves as the stable gasoline absorbent feeding pipeline.

The demethanizer 13 is connected at a top thereof with the cooling unit III 10, and is connected at a bottom thereof with the depropanizer 15.

The depropanizer 15 is connected on an upper portion thereof with the deethanizer 14, and is provided at a bottom thereof with a mixed $C_4$ product collecting pipeline. The mixed $C_4$ product collecting pipeline is divided into two branches, one of which serves as a mixed $C_4$ absorbent feeding pipeline.

The deethanizer 14 is provided at a top thereof with a mixed $C_2$ collecting pipeline provided thereon with an impurity treatment unit 18, and is provided at a bottom thereof with a mixed $C_3$ collecting pipeline. The mixed $C_3$ collecting pipeline is connected with the propylene rectifying column 16.

The propylene rectifying column 16 is provided at a top thereof with a propylene product collecting pipeline, and is provided at a bottom thereof with a propane product collecting pipeline.

Figure 3:
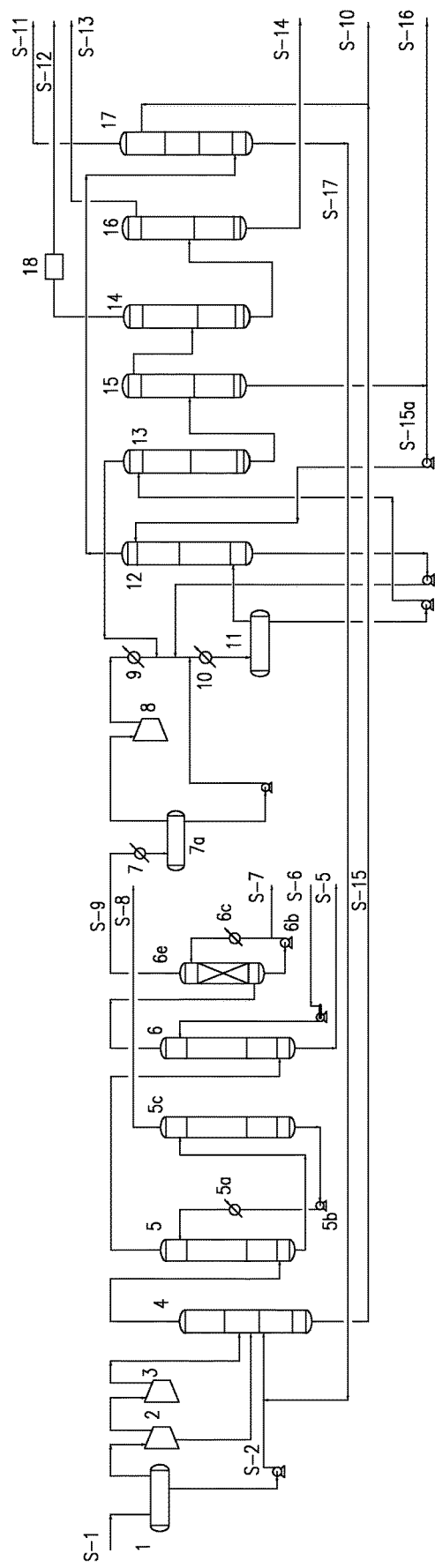
FIG. 3 is a flow diagram of a process of desulfurization as well as separation for and recovery of light hydrocarbons in oil gas treatment according to Example 3 of the present invention.

A process flow of the separation is shown in FIG. 3.

Cooling: The impurity-removed rich gas S-9 was cooled preliminarily in the cooling unit I 7 and then sent to the gas-liquid separation tank II 7a. A resulting gas phase at a top of the gas-liquid separation tank II 7a was compressed and re-cooled and then sent to the cooling unit III 10, and a resulting liquid phase at a bottom of the gas-liquid separation tank II 7a was pressurized and then sent to the cooling unit III.

Post-cooling: The preliminarily pressurized and cooled gas phase and the pressurized liquid phase were further mixed and cooled in the cooling unit III 10 and then sent to the feeding tank 11 as a mixed stream.

Feeding: The mixed stream from the cooling unit III 10 was mixed and pre-absorbed to reach gas-liquid equilibrium in the feeding tank 11. A resulting gas phase at a top of the feeding tank 11 was sent to the absorption column 12, and a resulting liquid phase at a bottom of the feeding tank 11 was sent to the demethanizer 13. The feeding tank 11 had an operating temperature of 5-25° C., and an operating pressure of 2.2-2.8 MPaG.

Absorption: In the absorption column 12, a mixed $C_4$ was used as an absorbent to absorb $C_2$ and $C_{2+}$ components present in the gas phase from the top of the feeding tank 11, and to simultaneously co-absorb part of methane. A resulting gas phase at a top of the absorption column 12 was sent to the absorbent recovery column 17, and a resulting liquid phase at a bottom of the absorption column 12 was returned to the cooling unit III. The absorption column 12 had an operating temperature of 5-25° C., and an operating pressure of 2.1-2.7 MPaG. The absorbent used in the absorption column 12 was from a self-balanced mixed $C_4$ component in the system and did not need to be introduced from outside the system.

Demethanization: The liquid phase from the bottom of the feeding tank 11 was subjected to removal of methane and simultaneously to removal of small part of $C_2$ and $C_{2+}$ components in the demethanizer 13. A resulting gas phase at a top of the demethanizer 13 was sent to the cooling unit III 10, and a resulting liquid phase at a bottom of the demethanizer 13 was sent to the depropanizer 15. The demethanizer 13 had an operating temperature of 10-40° C. at the top thereof, and had an operating temperature of 70-95° C. and an operating temperature of 2.3-2.9 MPaG at the bottom thereof.

Depropanization: The liquid phase from the bottom of the demethanizer 13 was subjected to separation in the depropanizer 15. $C_3$ and $C_{3-}$ components obtained from the separation were collected from an upper portion of the depropanizer 15 and then sent to the deethanizer 14. At least part of resulting components at a bottom of the depropanizer 15 was sent as a mixed $C_4$ absorbent to the absorption column, and the rest was collected as a mixed $C_4$ product S-16. The depropanizer had an operating temperature of 15-50° C. at the top thereof, and had an operating temperature of 80-120° C. and an operating pressure of 1.6-2.4 MPaG at the bottom thereof.

Deethanization: The gas phase from the upper portion of the depropanizer 15 was subjected to further separation in the deethanizer 14. A mixed $C_2$ component obtained from the separation was subjected to impurity removal and then collected from a top of the deethanizer 14 as a mixed $C_2$ product, and a resulting liquid phase at a bottom of the deethanizer 14 was collected as a mixed $C_3$ component. The deethanizer 14 had an operating temperature of 5-20° C. and an operating pressure of 2.6-3.2 MPaG at the top thereof, and had an operating temperature of 55-85° C. at the bottom thereof.

Propylene rectification: The mixed $C_3$ component collected from the bottom of the deethanizer 14 was sent to the propylene rectifying column 16 for further rectification. A resulting gas phase at a top of the propylene rectifying column 16 was cooled and then collected as a propylene product, and a resulting liquid phase at a bottom of the propylene rectifying column 16 was collected as a propane product. The propylene rectifying column 16 had an operating temperature of 45-60° C., and an operating pressure of 1.8-2.0 MPaG.

Recovery of absorbent: In the absorbent recovery column 17, at least part of the stable gasoline product collected in step (2) was used as an absorbent to absorb $C_4$ and $C_{4+}$ components present in the gas phase from the top of the absorption column 12, and to simultaneously absorb small amounts of $C_2/C_3$ components. A resulting gas phase at a top of the absorbent recovery column 17 was collected as a dry gas S-11, and a resulting liquid phase at a bottom of the absorbent recovery column 17 was returned to the debutanizer 4. The absorbent recovery column 17 had an operating temperature of 15-40° C., and an operating pressure of 2.1-2.7 MPaG.

The light hydrocarbons in the rich gas were separated by the above method. Composition and properties of the products separated out are shown in Table 6, and properties of stable gasoline are shown in Table 7.

TABLE 6

|  | Dry gas | Mixed $C_2$ | Propylene | Propane | Mixed $C_4$ | Stable gasoline |
|---|---|---|---|---|---|---|
| Temperature, ° C. | 17 | 15 | 46 | 58 | 40 | 117 |
| Pressure, MPaG | 2.63 | 2.90 | 1.80 | 1.86 | 1.82 | 1.20 |
| Molar vapor fraction | 1 | 1 | 0 | 0 | 0 | 0 |
| Flow rate, kg/h | 4607 | 7515 | 17306 | 4929 | 28391 | 140801 |
| Molar fraction | | | | | | |
| $H_2$ | 0.4974 | | | | | |
| CO | 0.0083 | | | | | |
| $CO_2$ | 50 ppmw | 100 ppmw | | | | |
| $H_2S$ | 10 ppmw | 10 ppmw | 10 ppmw | 10 ppmw | 10 ppmw | |
| RSH | | 1 ppmw | 20 ppmw | 20 ppmw | 20 ppmw | |
| $O_2$ | 0.0098 | | | | | |
| $N_2$ | 0.0757 | | | | | |
| $CH_4$ | 0.3910 | 0.0089 | | | | |
| $C_2H_6$ | | 0.3899 | 0.0002 | | | |
| $C_2H_4$ | 0.0029 | 0.4320 | | | | |
| $C_3H_6$ | | 0.1485 | 0.9962 | 0.0153 | 0.0023 | |
| $C_3H_8$ | | 0.0205 | 0.0036 | 0.9317 | 0.0043 | |
| $i\text{-}C_4H_{10}$ | 0.0003 | 0.0002 | | 0.0368 | 0.4224 | 0.0021 |
| $n\text{-}C_4H_{10}$ | 0.0002 | | | 0.0008 | 0.0879 | 0.0025 |
| $i\text{-}C_4H_8$ | 0.0002 | | | 0.0095 | 0.1684 | 0.0017 |
| $n\text{-}C_4H_8$ | 0.0001 | | | 0.0044 | 0.0930 | 0.0011 |
| $t\text{-}C_4H_8$ | 0.0003 | | | 0.0011 | 0.1271 | 0.0039 |
| $c\text{-}C_4H_8$ | 0.0004 | | | 0.0004 | 0.0876 | 0.0050 |
| $C_5+$ | 0.0134 | | | | 0.0070 | 0.9837 |
| Total | 1.00 | 1.00 | 1.00 | 1.00 | 1.00 | 1.00 |

TABLE 7

| Items | Numerical values |
|---|---|
| Density (20° C.), g/cm³ | 0.754 |
| Content of $C_4$ component, vol % | 1.63 |
| Reid Vapor Pressure, kPa | 67.5 |

| Curve of D86, v % | Temperature, ° C. |
|---|---|
| 0 | 38.5 |
| 5 | 46.2 |
| 10 | 49.3 |
| 30 | 72.1 |
| 50 | 94.4 |
| 70 | 127.6 |
| 90 | 176.9 |
| 95 | 187.3 |
| 100 | 197.8 |

Example 4

The rich gas obtained after the impurity removal in Example 2 was subjected to separation for light hydrocarbons. A separation unit including: a cooling unit I 7, a gas-liquid separation tank II 7a, a compressor III 8, a cooling unit II 9, a cooling unit III 10, a feeding tank 11, an absorption column 12, a demethanizer 13, a depropanizer 15, a deethanizer 14, a propylene rectifying column 16, and an absorbent recovery column 17 was used.

A light hydrocarbon collecting pipeline is connected sequentially with the cooling unit I 7 and the gas-liquid separation tank II 7a. The gas-liquid separation tank II 7a is sequentially connected at a top thereof with the compressor III 8, the cooling unit II 9, the cooling unit III 10, and the feeding tank 11, and is connected at a bottom thereof sequentially with the cooling unit III 10 and the feeding tank 11.

The feeding tank 11 is connected at a top thereof with the absorption column 12, and is connected at a bottom thereof with the demethanizer 13.

The absorption column 12 is connected at a top thereof with the absorbent recovery column 17, is connected at a bottom thereof with the cooling unit III 10, and is provided on an upper portion thereof with a mixed $C_4$ absorbent feeding pipeline.

The absorbent recovery column 17 is provided at a top thereof with a dry gas collecting pipeline, is connected at a bottom thereof with the debutanizer 4, and is provided on an upper portion thereof with a stable gasoline absorbent feeding pipeline. A stable gasoline collecting pipeline of the debutanizer 4 is divided into two branches, one of which serves as the stable gasoline absorbent feeding pipeline.

The demethanizer 13 is connected at a top thereof with the cooling unit III 10, and is connected at a bottom thereof with the depropanizer 15.

The depropanizer 15 is connected on an upper portion thereof sequentially with a drying unit 19 and the deethanizer 14, and is provided at a bottom thereof with a mixed $C_4$ product collecting pipeline. The mixed $C_4$ product collecting pipeline is divided into two branches, one of which serves as a mixed $C_4$ absorbent feeding pipeline.

The deethanizer 14 is provided at a top thereof with a mixed $C_2$ collecting pipeline provided thereon with an impurity treatment unit 18, and is provided at a bottom thereof with a mixed $C_3$ collecting pipeline. The mixed $C_3$ collecting pipeline is connected with the propylene rectifying column 16.

The propylene rectifying column 16 is provided at a top thereof with a propylene product collecting pipeline, and is provided at a bottom thereof with a propane product collecting pipeline.

Figure 4:
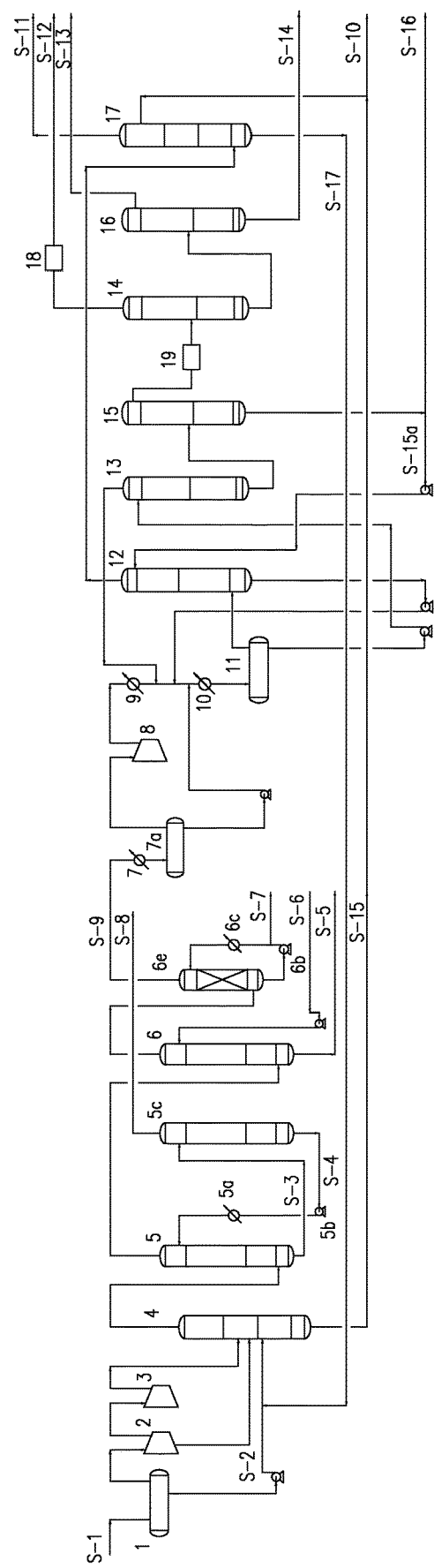
FIG. 4 is a flow diagram of a process of desulfurization as well as separation for and recovery of light hydrocarbons in oil gas treatment according to Example 4 of the present invention.

A process flow of the separation is shown in FIG. 4.

Cooling: The impurity-removed rich gas S-9 was cooled preliminarily in the cooling unit I 7 and then sent to the gas-liquid separation tank II 7a. A resulting gas phase at a top of the gas-liquid separation tank II 7a was compressed and re-cooled and then sent to the cooling unit III 10, and a resulting liquid phase at a bottom of the gas-liquid separation tank II 7a was pressurized and then sent to the cooling unit III 10.

Post-cooling: The preliminarily pressurized and cooled gas phase and the pressurized liquid phase were further mixed and cooled in the cooling unit III 10 and then sent to the feeding tank 11 as a mixed stream.

Feeding: The mixed stream from the cooling unit III 10 was mixed and pre-absorbed to reach gas-liquid equilibrium in the feeding tank 11. A resulting gas phase at a top of the feeding tank 11 was sent to the absorption column 12, and a resulting liquid phase at a bottom of the feeding tank 11 was sent to the demethanizer 13. The feeding tank 11 had an operating temperature of 5-25° C., and an operating pressure of 2.2-2.8 MPaG.

Absorption: In the absorption column 12, a mixed $C_4$ was used as an absorbent to absorb $C_2$ and $C_{2+}$ components present in the gas phase from the top of the feeding tank 11, and to simultaneously co-absorb part of methane. A resulting gas phase at a top of the absorption column 12 was sent to the absorbent recovery column 17, and a resulting liquid phase at a bottom of the absorption column 12 was returned to the cooling unit III. The absorption column 12 had an operating temperature of 5-25° C., and an operating pressure of 2.1-2.7 MPaG. The absorbent used in the absorption column 12 was from a self-balanced mixed $C_4$ component in the system and did not need to be introduced from outside the system.

Demethanization: The liquid phase from the bottom of the feeding tank 11 was subjected to removal of methane and simultaneously to removal of small part of $C_2$ and $C_{2+}$ components in the demethanizer 13. A resulting gas phase at a top of the demethanizer 13 was sent to the cooling unit III 10, and a resulting liquid phase at a bottom of the demethanizer 13 was sent to the depropanizer 15. The demethanizer 13 had an operating temperature of 10-40° C. at the top thereof, and had an operating temperature of 70-95° C. and an operating pressure of 2.3-2.9 MPaG at the bottom thereof.

Depropanization: The liquid phase from the bottom of the demethanizer 13 was subjected to separation in the depropanizer 15. $C_3$ and $C_{3-}$ components obtained from the separation were collected from an upper portion of the depropanizer 15, dried, and then sent to the deethanizer 14. At least part of resulting components at a bottom of the depropanizer 15 was sent as a mixed $C_4$ absorbent to the absorption column, and the rest was collected as a $C_4$ product S-16. The depropanizer had an operating temperature of 15-50° C. at the top thereof, and had an operating temperature of 80-120° C. and an operating pressure of 1.6-2.4 MPaG at the bottom thereof.

Drying and dehydration: The gas phase from the upper portion of the depropanizer 15 was dehydrated in the drying unit 19. The gas phase after the dehydration in the drying unit had a water dew point of less than −40° C. A 3 A/5 A molecular sieve was used as a dehydrating adsorbent in the drying unit.

Deethanization: The gas phase after being treated in the drying unit 19 was subjected to further separation in the deethanizer 14. A mixed $C_2$ component obtained from the separation was subjected to impurity removal and then collected from a top of the deethanizer as a mixed $C_2$ product, and a resulting liquid phase at a bottom of the deethanizer was collected as a mixed $C_3$ component. Fine separation was used in the deethanizer 14. The deethanizer 14 had an operating temperature of from −20° C. to −5° C. and an operating pressure of 2.2-2.8 MPaG at the top thereof, and had an operating temperature of 55-80° C. at the bottom thereof. Due to the relatively low temperature at the top of the deethanizer, it was required that a propylene refrigerant or other refrigerants from −25° C. to −15° C. be used. To meet the requirement set for the top of the deethanizer, a separate propylene refrigeration system can be designed, or other refrigerants that meet the requirements can be sued.

Propylene rectification: The mixed $C_3$ component collected from the bottom of the deethanizer 14 was sent to the propylene rectifying column 16 for further rectification. A resulting gas phase at a top of the propylene rectifying column 16 was cooled and then collected as a propylene product, and a resulting liquid phase at a bottom of the propylene rectifying column 16 was collected as a propane product. The propylene rectifying column 16 had an operating temperature of 45-60° C., and an operating pressure of 1.8-2.0 MPaG.

Recovery of absorbent: In the absorbent recovery column 17, at least part of the stable gasoline product collected in step (2) was used as an absorbent to absorb $C_4$ and $C_{4+}$ components present in the gas phase from the top of the absorption column 12, and to simultaneously absorb small amounts of $C_2/C_3$ components. A resulting gas phase at a top of the absorbent recovery column 17 was collected as a dry gas S-11, and a resulting liquid phase at a bottom of the absorbent recovery column 17 was returned to the debutanizer 4. The absorbent recovery column had an operating temperature of 15-40° C., and an operating pressure of 2.1-2.7 MPaG.

The light hydrocarbons in the rich gas were separated out by the above method. Composition and properties of the products separated out are shown in Table 8, and properties of stable gasoline are shown in Table 9.

TABLE 8

|  | Dry gas | Mixed $C_2$ | Propylene | Propane | Mixed $C_4$ | Stable gasoline |
| --- | --- | --- | --- | --- | --- | --- |
| Temperature, ° C. | 17 | −18 | 46 | 58 | 40 | 117 |
| Pressure, MPaG | 2.63 | 2.6 | 1.8 | 1.86 | 1.82 | 1.2 |
| Molar vapor fraction | 1 | 1 | 0 | 0 | 0 | 0 |
| Flow rate, kg/h | 4605 | 5239 | 18654 | 4935 | 28388 | 140826 |

TABLE 8-continued

|  | Dry gas | Mixed $C_2$ | Propylene | Propane | Mixed $C_4$ | Stable gasoline |
|---|---|---|---|---|---|---|
|  | | | Molar fraction | | | |
| $H_2$ | 0.4967 | | | | | |
| CO | 0.0083 | | | | | |
| $CO_2$ | 50 ppmw | 100 ppmw | | | | |
| $H_2S$ | 10 ppmw | 10 ppmw | 10 ppmw | 10 ppmw | 10 ppmw | |
| RSH | | 1 ppmw | 20 ppmw | 20 ppmw | 20 ppmw | |
| $O_2$ | 0.0098 | | | | | |
| $N_2$ | 0.0757 | | | | | |
| $CH_4$ | 0.3917 | 0.0088 | | | | |
| $C_2H_6$ | | 0.4672 | 0.0002 | | | |
| $C_2H_4$ | 0.0029 | 0.5177 | | | | |
| $C_3H_6$ | | 0.0062 | 0.9962 | 0.0343 | 0.0023 | |
| $C_3H_8$ | | 0.0036 | | 0.9328 | 0.0043 | |
| $i-C_4H_{10}$ | 0.0003 | | | 0.0167 | 0.4225 | 0.0021 |
| $n-C_4H_{10}$ | 0.0002 | | | 0.0008 | 0.0878 | 0.0025 |
| $i-C_4H_8$ | 0.0002 | | | 0.0095 | 0.1683 | 0.0017 |
| $n-C_4H_8$ | 0.0001 | | | 0.0044 | 0.0931 | 0.0011 |
| $t-C_4H_8$ | 0.0003 | | | 0.0011 | 0.1271 | 0.0039 |
| $c-C_4H_8$ | 0.0004 | | | 0.0004 | 0.0876 | 0.005 |
| $C_5+$ | 0.0134 | | | | 0.007 | 0.9837 |
| Total | 1.00 | 1.00 | 1.00 | 1.00 | 1.00 | 1.00 |

TABLE 9

| Items | Numerical values |
|---|---|
| Density (20° C.), g/cm³ | 0.753 |
| Content of $C_4$ component, vol % | 1.63 |
| Reid Vapor Pressure, kPa | 67.8 |
| Curve of D86, v % | Temperature, ° C. |
| 0 | 38.7 |
| 5 | 46.1 |
| 10 | 49.1 |
| 30 | 72.0 |
| 50 | 94.4 |
| 70 | 127.6 |
| 90 | 176.9 |
| 95 | 187.3 |
| 100 | 197.7 |

As can be seen from Examples 3 and 4, the treatment method of the present invention can realize high-efficiency recovery of $C_2$, $C_3$ and $C_4$ components. The total recovery rate of the $C_2$ component is more than 98 wt %, and the recovery rate of the $C_3$ component is more than 99 wt %. The recovered $C_2$ component has a content of methane of not more than 1 vol %, and a content of ethane of not more than 2000 ppmv. Besides, the recovered $C_3$ component is further separated into propylene and propane. The recovery rates of propylene and propane is both more than 99 wt %. The propylene product has a purity of not less than 99.6 v %, and can be used as polymer-grade propylene without further treatment. The recovered dry gas has relatively small amounts of impurities and a content of $C_2$ and $C_{2+}$ components of not more than 2 vol %. The dry gas after the absorption has a pressure of 2.1-2.7 MPa. The purity of hydrogen in the dry gas is up to 40-70 mol %. The hydrogen resource can be directly recovered by pressure swing adsorption. The collected stable gasoline has a dry point of 197° C. and has a content of the $C_4$ component of only 1.63 vol %, and can meet quality requirements for a gasoline product after being treated by desulfurization.

In addition, providing the drying unit above the top of the depropanizer and adopting fine treatment in the deethanizer can help to eliminate the defect that when depropanization is performed first the mixed $C_2$ component separated out will contain about 20 v % of the mixed $C_3$ component. In this way, $C_2$ component separated out will basically contain no $C_3$ component. The impurity-removed stream at the top of the deethanizer can be directly sent to a downstream ethylene unit for recovery of $C_2$ or for direct use.

Example 5

A device for high-pressure desulfurization and separation of oil gas was used.

The device for high-pressure desulfurization and separation of an oil gas includes: an oil gas feeding pipeline, a gas-liquid separation tank I 1, a compressor I 2, a compressor II 3, a debutanizer 4, a compressor III 8, a cooling unit II 9, a gas-liquid separation tank II 7a, a rich gas desulfurizing column 5, a rich gas sweetening column 6, a liquid hydrocarbon desulfurizing column 5a, a liquid hydrocarbon sweetening reactor 6a, a cooling unit III 10, a feeding tank 11, an absorption column 12, a demethanizer 13, a deethanizer 14, an impurity treatment unit 18, a depropanizer 15, a propylene rectifying column 16, and an absorbent recovery column 17, and does not include a dehydration device.

The oil gas feeding pipeline is connected with an inlet of the gas-liquid separation tank I 1. The gas-liquid separation tank I is connected at a top thereof sequentially with the compressor I 2, the compressor II 3, and the debutanizer 4. A liquid phase collecting pipeline between stages of the compressor is connected with the debutanizer. The gas-liquid separation tank I is connected at a bottom thereof with the debutanizer 4.

The debutanizer 4 is provided at a top thereof with a reflux tank. The reflux tank is connected at a top thereof sequentially with the compressor III 8, the cooling unit II 9, and the gas-liquid separation tank II 7a, and is connected at a bottom thereof first with a booster pump and then with the gas-liquid separation tank II 7a. The debutanizer 4 is provided at a bottom thereof with two stable gasoline collecting pipelines.

The gas-liquid separation tank II 7a is connected at a top thereof sequentially with the rich gas desulfurizing column 5, the rich gas sweetening column 6, and the cooling unit III 10, and is connected at a bottom thereof sequentially with the liquid hydrocarbon desulfurizing column 5a, the liquid hydrocarbon sweetening reactor 6a, and the cooling unit III 10.

The rich gas desulfurizing column 5 is connected at a top thereof with the rich-gas sweetening column 6, is provided at the top thereof with a rich amine solution collecting pipeline, and is provided on an upper portion thereof with a lean amine solution feeding pipeline. The rich gas sweetening column 6 is connected at a top thereof with the cooling unit III 10, is provided at a bottom thereof with an alkali liquor-to-be-generated collecting pipeline, and is provided on an upper portion thereof with an alkali liquor feeding pipeline.

The cooling unit III 10 is connected with the feeding tank 11.

The feeding tank 11 is connected at a top thereof with the absorption column 12, and is connected at a bottom thereof with the demethanizer 13.

The absorption column 12 is provided with two to five middle-stage reflux, is connected at a top thereof with the absorbent recovery column 17, is connected at a bottom thereof with the cooling unit III 10, and is provided on an upper portion thereof with a mixed $C_4$ absorbent feeding pipeline.

The absorbent recovery column 17 is provided at a top thereof with a dry gas collecting pipeline, is connected at a bottom thereof with the debutanizer 4, and is provided on an upper portion thereof with a stable gasoline absorbent feeding pipeline connected with the stable gasoline collecting pipeline of the debutanizer 4.

The demethanizer 13 is not provided at a top thereof with a condenser, but is provided at a bottom thereof with a reboiler. The demethanizer 13 is connected at the top thereof with the cooling unit III 10 and is connected at the bottom thereof with the deethanizer 14.

The deethanizer 14 is provided at a top thereof with a mixed $C_2$ collecting pipeline provided thereon with the impurity treatment unit 18, and is connected at a bottom thereof with the depropanizer 15.

The depropanizer 15 is connected at the top thereof with the propylene rectifying column 16, and is provided at a bottom thereof with a mixed $C_4$ product collecting pipeline connected with the mixed $C_4$ absorbent feeding pipeline.

The propylene rectifying column 16 is provided at a top thereof with a propylene product collecting pipeline, and is provided at a bottom thereof with a propane product collecting pipeline.

Figure 5:
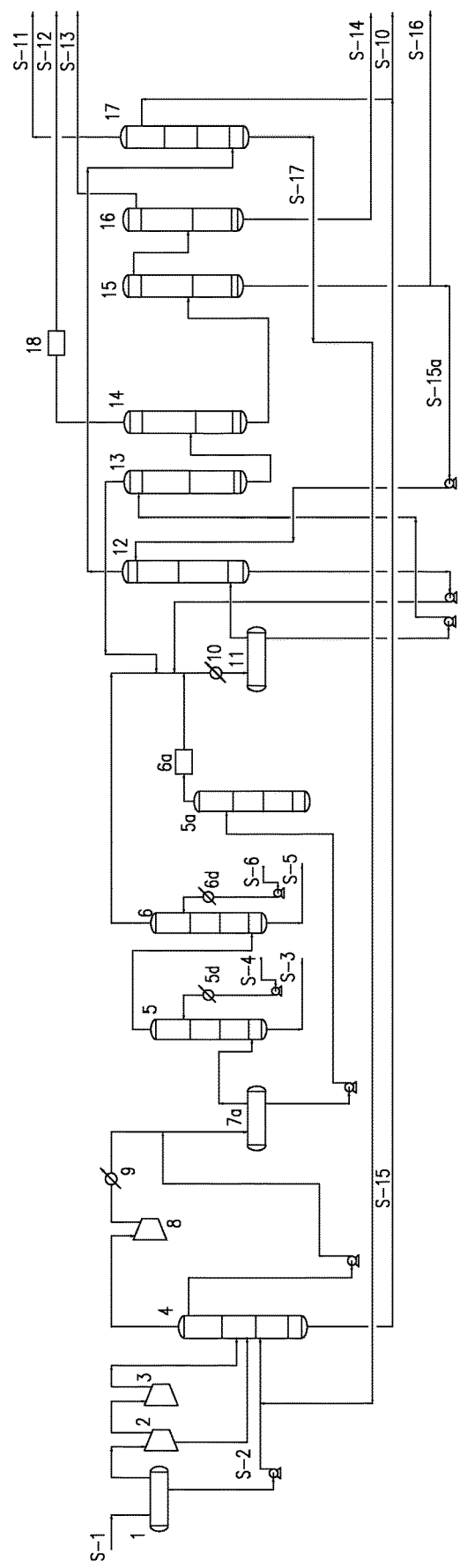
FIG. 5 is a flow diagram of a process of high-pressure desulfurization and separation of an oil gas according to Example 5 of the present invention.

Light hydrocarbons were separated out using the above device. A process flow of the separation is shown in FIG. 5.

(1) First gas-liquid separation: an oil gas S-1 from an upstream device was condensed and cooled and then sent to the gas-liquid separation tank I 1 for gas-liquid separation. A resulting liquid phase at a bottom of the gas-liquid separation tank 11 was pressurized and then sent to the debutanizer 4, and a gas phase at a top of the gas-liquid separation tank I 1 was compressed by the compressor and then sent to the debutanizer 4. A liquid phase between the stages of the compressor was sent to the debutanizer 4.

(2) Debutanization: The gas phase and the liquid phase from step (1) entered into the debutanizer 4. A gas phase distilled off at a top of the debutanizer 4 was condensed and then sent into a reflux tank at the top of the debutanizer 4. A resulting gas phase at a top of the reflux tank at the top of the debutanizer was compressed and cooled and then sent to the gas-liquid separation tank II 7a, and a resulting liquid phase at a bottom of the reflux tank was pressurized and then sent to the gas-liquid separation tank II 7a. At least part of a resulting liquid phase at a bottom of the debutanizer 4 was collected as a stable gasoline product S-10. The debutanizer 4 had an operating temperature of 45-60° C., and an operating pressure of 1.0-1.5 MPaG. The reflux tank had a temperature of 40-45° C.

(3) Second gas-liquid separation: Materials were mixed to reach gas-liquid equilibrium in the gas-liquid separation tank II 7a, and then subjected to separation to obtain a gas phase and a liquid phase. The gas phase and the liquid phase were then subjected to impurity removal, respectively. The gas phase at the top of the reflux tank was compressed to 2.5-3.0 MPaG, cooled to 35-45° C. and sent to the gas-liquid separation tank II 7a. The liquid phase at the bottom of the reflux tank was pressurized to 2.8-3.3 MPaG and then sent to the gas-liquid separation tank II 7a.

(4) Gas phase impurity removal: The gas phase at a top of the gas-liquid separation tank II 7a obtained from the separation in the gas-liquid separation tank II was sequentially subjected to removal of $H_2S$ and $CO_2$ in the rich gas desulfurizing column 5 with a lean amine solution S-4 as an absorbent, to removal of mercaptans in the rich gas sweetening column 6 with an alkali liquor S-6 as an absorbent, and then sent to the cooling unit III 10. The rich gas desulfurizing column 5 had an operating temperature of 35-45° C., an operating pressure of 2.5-3.0 MPaG. The rich gas sweetening column 6 had an operating temperature of 35-45° C., and an operating pressure of 2.4-2.9 MPaG (properties of the rich gas at the top of the rich gas sweetening column are shown in Table 10).

(5) Liquid phase impurity removal: The liquid phase at a bottom of the gas-liquid separation tank II 7a obtained from the separation in the gas-liquid separation tank II 7a was sequentially subjected to removal of $H_2S$ and $CO_2$ in the liquid hydrocarbon desulfurizing column 5a, to removal of mercaptans in the liquid hydrocarbon sweetening reactor 6a, and then sent to a cooling unit III 10. The liquid hydrocarbon desulfurizing column 5a had an operating temperature of 35-45° C., and an operating pressure of 3.0-3.5 MPaG (properties of liquid hydrocarbons at an outlet of the liquid hydrocarbon sweetening reactor are shown in Table 10).

(6) Cooling: The impurity-removed gaseous light hydrocarbons and the impurity-removed liquid hydrocarbons were mixed and cooled preliminarily in the cooling unit III 10 and then sent to the feeding tank 11 as a mixed steam.

(7) Feeding: The mixed stream from the cooling unit III 10 was mixed and pre-absorbed to reach gas-liquid equilibrium in the feeding tank 11. A resulting gas phase at a top of the feeding tank 11 was sent to the absorption column 12, and a resulting liquid phase at a bottom of the feeding tank 11 was sent to a separation unit. The feeding tank 11 had an operating temperature of 5-25° C., and an operating pressure of 2.4-2.9 MPaG.

(8) Absorption: In the absorption column 12, a mixed $C_4$ from the bottom of the debutanizer 4 was used as an absorbent to absorb $C_2$ and $C_{2+}$ components present in the gas phase from the top of the feeding tank 11, and to simultaneously co-absorb part of methane. A resulting gas phase at a top of the absorption column 12 was sent to the absorbent recovery column 17 for further recovery of the absorbent, and a resulting liquid phase at a bottom of the absorption column 12 was returned to the cooling unit III 10. The absorption column had an operating temperature of 5-25° C., and an operating pressure of 2.4-2.9 MPaG.

(9) Separation:

Demethanization: The liquid phase from the bottom of the feeding tank 11 was subjected to removal of methane and simultaneously to removal of small part of $C_2$ and $C_{2+}$ components in the demethanizer 13. A resulting gas phase at a top of the demethanizer 13 was sent to the cooling unit III 10, and a resulting liquid phase at a bottom of the demethanizer 13 was sent to the deethanizer 14. The demethanizer 13 had an operating temperature of 10-40° C. at a top thereof, and had an operating temperature of 70-95° C. and an operating pressure of 2.4-2.9 MPaG.

Deethanization: The liquid phase from the bottom of the demethanizer 13 was subjected to separation in the deethanizer 14 to obtain a $C_2$ component. A mixed $C_2$ component obtained from the separation was subjected to impurity removal, and then collected from a top of the deethanizer 14 as a mixed $C_2$ product S-12, and resulting liquid-phase components of $C_3$ and $C_{3+}$ at a bottom of the deethanizer 14 were sent to the depropanizer 15. The deethanizer 14 had an operating temperature of 5-15° C. and an operating pressure of 2.2-3.0 MPaG at the top thereof, and had an operating temperature of 50-110° C. at the bottom thereof.

Depropanization: The liquid-phase components from the bottom of the deethanizer 15 were subjected to further separation in the depropanizer 15. A $C_3$ component obtained from the separation was collected from a top of the depropanizer 15 and sent to the propylene rectifying column 16 for further rectification. At least part of components at a bottom of the depropanizer 15 was sent as a mixed $C_4$ absorbent S-15a to the absorption column 12, and the rest was collected as a mixed $C_4$ product S-16. The depropanizer 15 had an operating temperature of 43-50° C. at the top thereof, and had an operating temperature of 100-120° C. and an operating temperature of 1.6-2.0 MPaG at the bottom thereof.

Propylene rectification: The gas phase from the top of the depropanizer 15 was subjected to further rectification in the propylene rectifying column 16. A resulting gas phase at a top of the propylene rectifying column 16 was collected as a propylene product S-13, and a resulting liquid phase at a bottom of the propylene rectifying column 16 was collected as a propane product S-14. The propylene rectifying column 16 had an operating temperature of 45-65° C., and an operating pressure of 1.8-2.0 MPaG.

(10) Recovery of absorbent: In the absorbent recovery column 17, at least part of the stable gasoline product collected in step (2) was used as an absorbent to absorb $C_4$ and $C_{4+}$ components present in the gas phase from the top of the absorption column 12, and to simultaneously absorb small amounts of $C_2/C_3$ components. A resulting gas phase at a top of the absorbent recovery column 17 was collected as a dry gas S-11, and a resulting liquid phase at a bottom of the absorbent recovery column 17 was returned to the debutanizer 4. The absorbent recovery column 17 had an operating temperature of 5-25° C., and an operating pressure of 2.3-2.8 MPaG.

The light hydrocarbons in the oil gas were separated out by the above method. Composition and properties of the products separated out are shown in Table 11. Properties of the collected stable gasoline products are shown in Table 12.

TABLE 10

| Items | Rich gas (after desulfuration and sweetening) | Liquid light hydrocarbons (after desulfuration and sweetening) |
|---|---|---|
| Temperature, ° C. | 40 | 40 |
| Pressure, MPaG | 2.8 | 2.8 |
| Molar vapor fraction | 1 | 0 |
| Flow rate, kg/h | 54175 | 114531 |

| Components | Molar Fraction | |
|---|---|---|
| $H_2$ | 0.1821 | 0.0063 |
| $O_2$ | 0.0026 | 0.0003 |
| $N_2$ | 0.0486 | 0.0035 |
| $CH_4$ | 0.1780 | 0.0300 |
| $C_2H_6$ | 0.0652 | 0.0422 |
| $C_2H_4$ | 0.1415 | 0.0661 |
| $C_3H_6$ | 0.2169 | 0.3294 |
| $C_3H_8$ | 0.0351 | 0.0595 |
| i-$C_4H_{10}$ | 0.0380 | 0.1359 |
| n-$C_4H_{10}$ | 0.0097 | 0.0425 |
| i-$C_4H_8$ | 0.0297 | 0.1134 |
| n-$C_4H_8$ | 0.0120 | 0.0470 |
| t-$C_4H_8$ | 0.0147 | 0.0669 |
| c-$C_4H_8$ | 0.0100 | 0.0485 |
| $C_4H_6$ | 0.0001 | 0.0003 |
| $H_2O$ | 0.0084 | 0.0038 |
| $C_5+$ | 0.0074 | 0.0046 |
| Total | 1.000 | 1.000 |
| $CO_2$ | 50 ppmv | 110 ppmv |
| $H_2S$ | 10 ppmv | 10 ppmv |
| RSH | 20 ppmv | 20 ppmv |

TABLE 11

| | dry gas | mixed $C_2$ | propylene | propane | mixed $C_4$ | stable gasoline |
|---|---|---|---|---|---|---|
| Temperature, ° C. | 17 | 15 | 46 | 58 | 40 | 117 |
| Pressure, MPaG | 2.63 | 2.90 | 1.80 | 1.86 | 1.82 | 1.20 |
| Molar vapor fraction | 1 | 1 | 0 | 0 | 0 | 0 |
| Flow rate, kg/h | 4602 | 7518 | 17310. | 4926 | 28387 | 140813 |
| | Molar Fraction | | | | | |
| $H_2$ | 0.4964 | | | | | |
| CO | 0.0083 | | | | | |
| $CO_2$ | 50 ppmv | 100 ppmv | | | | |
| $H_2S$ | 10 ppmv | 10 ppmv | 10 ppmv | 10 ppmv | 10 ppmv | |
| RSH | | 1 ppmv | 20 ppmv | 20 ppmv | 20 ppmv | |
| $O_2$ | 0.0098 | | | | | |
| $N_2$ | 0.0757 | | | | | |
| $CH_4$ | 0.3920 | 0.0089 | | | | |

TABLE 11-continued

|  | dry gas | mixed $C_2$ | propylene | propane | mixed $C_4$ | stable gasoline |
|---|---|---|---|---|---|---|
| $C_2H_6$ |  | 0.3899 | 0.0002 |  |  |  |
| $C_2H_4$ | 0.0029 | 0.4320 |  |  |  |  |
| $C_3H_6$ |  | 0.1484 | 0.9960 | 0.0153 | 0.0023 |  |
| $C_3H_8$ |  | 0.0206 | 0.0038 | 0.9317 | 0.0043 |  |
| $i-C_4H_{10}$ | 0.0003 | 0.0002 |  | 0.0368 | 0.4224 | 0.0021 |
| $n-C_4H_{10}$ | 0.0002 |  |  | 0.0008 | 0.0879 | 0.0025 |
| $i-C_4H_8$ | 0.0002 |  |  | 0.0095 | 0.1684 | 0.0017 |
| $n-C_4H_8$ | 0.0001 |  |  | 0.0044 | 0.0930 | 0.0011 |
| $t-C_4H_8$ | 0.0003 |  |  | 0.0011 | 0.1271 | 0.0039 |
| $c-C_4H_8$ | 0.0004 |  |  | 0.0004 | 0.0876 | 0.0050 |
| $C_5+$ | 0.0134 |  |  |  | 0.0070 | 0.9837 |
| Total | 1.00 | 1.00 | 1.00 | 1.00 | 1.00 | 1.00 |

TABLE 12

| Items | Numeric Values |
|---|---|
| Density (20° C.), g/cm³ | 0.753 |
| Content of $C_4$ component, vol % | 1.63 |
| Reid Vapor Pressure, kPa | 67.8 |

| Curve of D86, v % | Temperature, ° C. |
|---|---|
| 0 | 38.7 |
| 5 | 46.1 |
| 10 | 49.1 |
| 30 | 72.0 |

TABLE 12-continued

| 50 | 94.4 |
| 70 | 127.6 |
| 90 | 176.9 |
| 95 | 187.3 |
| 100 | 197.7 |

Example 6

Figure 6:
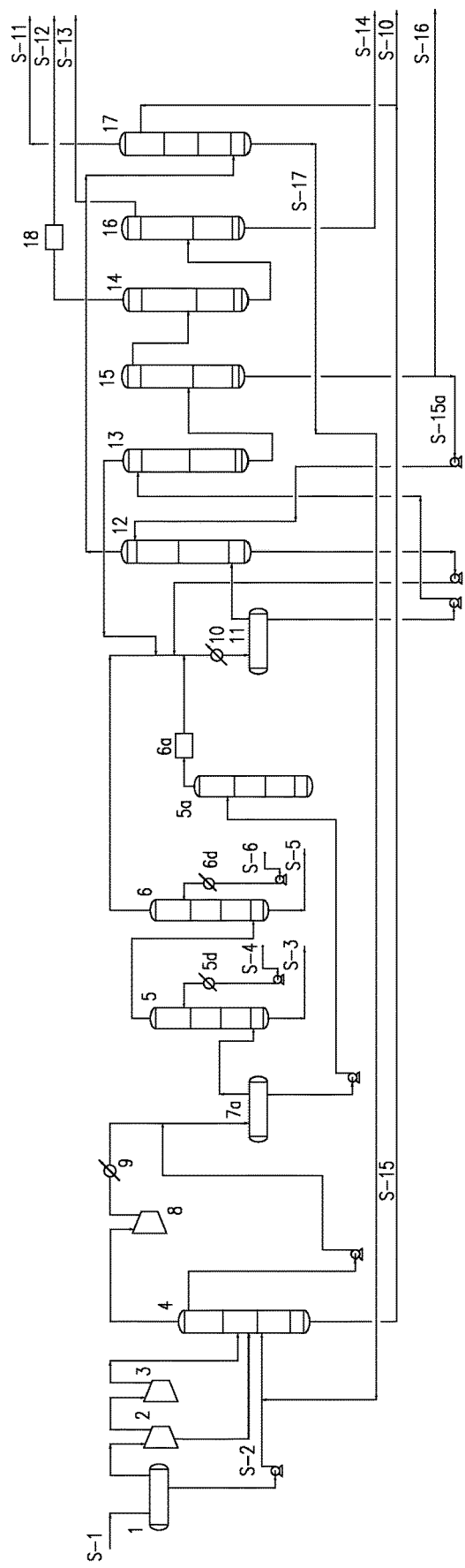
FIG. 6 is a flow diagram of a process of high-pressure desulfurization and separation of an oil gas according to Example 6 of the present invention.

High-pressure desulfurization and separation of an oil gas was performed according to a process flow shown in FIG. 6.

Example 6 differs from Example 5 in that: in step (9) of Example 6, a process II (i.e., demethanization, depropanization, deethanization, and propylene rectification were performed in sequence) was used for the separation. Composition and properties of products separated out are shown in Table 13. Properties of collected stable gasoline product are shown in Table 14.

TABLE 13

|  | Dry gas | Mixed $C_2$ | Propylene | Propane | Mixed $C_4$ | Stable gasoline |
|---|---|---|---|---|---|---|
| Temperature, ° C. | 17 | 15 | 46 | 58 | 40 | 117 |
| Pressure, MPaG | 2.63 | 2.90 | 1.80 | 1.86 | 1.82 | 1.20 |
| Molar vapor fraction | 1 | 1 | 0 | 0 | 0 | 0 |
| Flow rate, kg/h |  |  |  |  |  |  |
| Temperature, ° C. | 4602 | 7521 | 17310. | 4913 | 28389 | 140826 |
| Molar Fraction |  |  |  |  |  |  |
| $H_2$ | 0.4964 |  |  |  |  |  |
| CO | 0.0083 |  |  |  |  |  |
| $CO_2$ | 50 ppmv | 100 ppmv |  |  |  |  |
| $H_2S$ | 10 ppmv | 10 ppmv | 10 ppmv | 10 ppmv | 10 ppmv |  |
| RSH |  | 1 ppmv | 20 ppmv | 20 ppmv | 20 ppmv |  |
| $O_2$ | 0.0098 |  |  |  |  |  |
| $N_2$ | 0.0757 |  |  |  |  |  |
| $CH_4$ | 0.3920 | 0.0089 |  |  |  |  |
| $C_2H_6$ |  | 0.3899 | 0.0002 |  |  |  |
| $C_2H_4$ | 0.0029 | 0.4320 |  |  |  |  |
| $C_3H_6$ |  | 0.1484 | 0.9960 | 0.0153 | 0.0023 |  |
| $C_3H_8$ |  | 0.0206 | 0.0038 | 0.9318 | 0.0043 |  |
| $i-C_4H_{10}$ | 0.0003 | 0.0002 |  | 0.0367 | 0.4225 | 0.0021 |
| $n-C_4H_{10}$ | 0.0002 |  |  | 0.0008 | 0.0878 | 0.0025 |
| $i-C_4H_8$ | 0.0002 |  |  | 0.0095 | 0.1683 | 0.0017 |
| $n-C_4H_8$ | 0.0001 |  |  | 0.0044 | 0.0931 | 0.0011 |
| $t-C_4H_8$ | 0.0003 |  |  | 0.0011 | 0.1271 | 0.0039 |
| $c-C_4H_8$ | 0.0004 |  |  | 0.0004 | 0.0876 | 0.0050 |
| $C_5+$ | 0.0134 |  |  |  | 0.0070 | 0.9837 |
| Total | 1.00 | 1.00 | 1.00 | 1.00 | 1.00 | 1.00 |

TABLE 14

| Items | Numerical values |
|---|---|
| Density (20° C.), g/cm³ | 0.753 |
| Content of $C_4$ component, vol % | 1.64 |
| Reid Vapor Pressure, kPa | 67.3 |

TABLE 14-continued

| Curve of D86, v % | Temperature, ° C. |
|---|---|
| 0 | 38.7 |
| 5 | 46.1 |
| 10 | 49.3 |
| 30 | 71.8 |
| 50 | 94.6 |
| 70 | 127.9 |
| 90 | 177.2 |
| 95 | 187.1 |
| 100 | 197.8 |

Example 7

Figure 7:
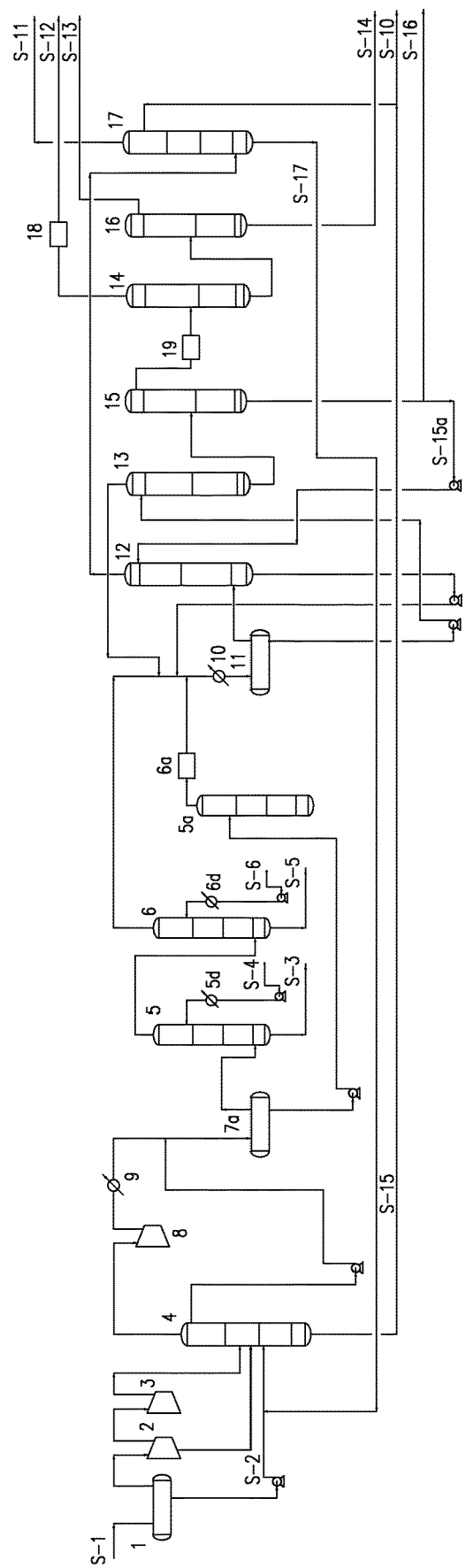
FIG. 7 is a flow diagram of a process of high-pressure desulfurization and separation of an oil gas according to Example 7 of the present invention.

High-pressure desulfurization and separation of an oil gas was performed according to a process flow shown in FIG. 7.

Example 7 differs from Example 6 in the following.

In depropanization, the $C_2$ and $C_3$ components separated out were collected from the upper portion of the depropanizer. The collected stream was dried (the dried stream had a dew point of less than −40° C.) and then sent to the deethanizer. Because the stream fed into the deethanizer was dried and dehydrated, the deethanizer adopted fine separation. A mixed $C_2$ product obtained at the top of the deethanizer from the separation had a content of propylene and heavier components of not more than 1 vol %. The deethanizer had an operating temperature of from −20° C. to −5° C. and an operating pressure of 2.2-2.8 MPaG at the top thereof, and had an operating temperature of 55-80° C. at the bottom thereof. Due to the lower temperature at the top of the deethanizer, it was required that a propylene refrigerant or other refrigerants of from −25° C. to −15° C. be used. To meet the requirement set for the top of the deethanizer, a separate propylene refrigeration system can be designed or other refrigerants that can meet the requirement can be used.

Composition and properties of products separated out are shown in Table 15, and properties of collected stable gasoline product are shown in Table 16.

TABLE 15

|  | dry gas | mixed $C_2$ | propylene | propane | mixed $C_4$ | stable gasoline |
|---|---|---|---|---|---|---|
| Temperature, ° C. | 17 | −18 | 46 | 58 | 40 | 117 |
| Pressure, MPaG | 2.63 | 2.6 | 1.8 | 1.86 | 1.82 | 1.2 |
| Molar vapor fraction | 1 | 1 | 0 | 0 | 0 | 0 |
| Flow rate, kg/h | 4602 | 5236 | 18657 | 4937 | 28389 | 140826 |
| Molar fraction | | | | | | |
| $H_2$ | 0.4964 | | | | | |
| CO | 0.0083 | | | | | |
| $CO_2$ | 50 ppmv | 100 ppmv | | | | |
| $H_2S$ | 10 ppmv | 10 ppmv | 10 ppmv | 10 ppmv | 10 ppmv | |
| RSH | | 1 ppmv | 20 ppmv | 20 ppmv | 20 ppmv | |
| $O_2$ | 0.0098 | | | | | |
| $N_2$ | 0.0757 | | | | | |
| $CH_4$ | 0.392 | 0.0088 | | | | |
| $C_2H_6$ | | 0.4672 | 0.0002 | | | |
| $C_2H_4$ | 0.0029 | 0.5177 | | | | |
| $C_3H_6$ | | 0.0062 | 0.996 | 0.0353 | 0.0023 | |
| $C_3H_8$ | | | 0.0038 | 0.9318 | 0.0043 | |
| $i$-$C_4H_{10}$ | 0.0003 | | | 0.0167 | 0.4225 | 0.0021 |
| $n$-$C_4H_{10}$ | 0.0002 | | | 0.0008 | 0.0878 | 0.0025 |
| $i$-$C_4H_8$ | 0.0002 | | | 0.0095 | 0.1683 | 0.0017 |
| $n$-$C_4H_8$ | 0.0001 | | | 0.0044 | 0.0931 | 0.0011 |
| $t$-$C_4H_8$ | 0.0003 | | | 0.0011 | 0.1271 | 0.0039 |
| $c$-$C_4H_8$ | 0.0004 | | | 0.0004 | 0.0876 | 0.005 |
| $C_5+$ | 0.0134 | | | | 0.007 | 0.9837 |
| Total | 1.00 | 1.00 | 1.00 | 1.00 | 1.00 | 1.00 |

TABLE 16

| Items | Numerical values |
|---|---|
| Density (20° C.), g/cm³ | 0.754 |
| Content of $C_4$ component, vol % | 1.63 |
| Reid Vapor Pressure, kPa | 67.8 |

| Curve of D86, v % | Temperature, ° C. |
|---|---|
| 0 | 38.9 |
| 5 | 46.2 |
| 10 | 49.3 |
| 30 | 72.0 |
| 50 | 94.7 |
| 70 | 128.2 |
| 90 | 177.1 |
| 95 | 187.6 |
| 100 | 197.7 |

It can be seen from the data in the above tables that the present invention is simple in its process and operated at moderate conditions, and consumes less energy. The separation for and recovery of the light hydrocarbons in the oil gas can be accomplished with relatively few devices. The total recovery rate of the $C_2$ component is more than 98 wt %, and the recovery rate of the $C_3$ component is more than 99 wt %. The recovered $C_2$ component has a content of methane of not more than 1 vol %, and a content of ethane of not more than 2000 ppmv. Besides, the recovered $C_3$ component is further separated into propylene and propane. Recovery rates of propylene and propane is both more than 99 wt %. The recovered dry gas contains relatively small amounts of impurities and has a content of $C_2$ and $C_{2+}$ components of not more than 2 vol %, and the purity of hydrogen is more than 40 mol %. The collected stable gasoline has a dry point of 197.7° C., and has a content of the $C_4$ component of only 1.63 vol %, and can meet quality requirements for a gasoline product after being treated by desulfurization.

Because desulfurization and sweetening performed on the gas phases and the liquid phases in Examples 5 to 7 were conducted at same conditions, capacities for impurity removal thereof were also the same. See Table 17 for details.

TABLE 17

| | Rich gas | | Liquid light hydrocarbons | |
| --- | --- | --- | --- | --- |
| Categories | Before desulfuration and sweetening | After desulfuration and sweetening | Before desulfuration and sweetening | After desulfuration and sweetening |
| $CO_2$ | 5952 ppmv | 50 ppmv | 2271 ppmv | 110 ppmv |
| $H_2S$ | 1260 ppmv | 10 ppmv | 1071 ppmv | 10 ppmv |
| RSH | 110 ppmv | 20 ppmw | 200 ppmv | 20 ppmw |

As can be seen from Table 17 above, by using the desulfurization and sweetening process of the present invention, the light hydrocarbons, after the gas phase undergoes the high-pressure desulfurization, has a content of $H_2S$ of not more than 10 ppmw and a content of mercaptans of not more than 20 ppmw, and $CO_2$ removal rate can reach 99.2 wt %; and the liquid light hydrocarbons has a content of $H_2S$ of 10 ppmw and a content of mercaptans of not more than 20 ppmw, and $CO_2$ removal rate can reach 95.2 wt %.

Example 8

A device for recovery of the oil gas comprises: an oil gas feeding pipeline, a gas-liquid separation tank 11, a compressor I 2, a light-heavy gasoline separation column 4a, a compressor II 3, a light hydrocarbon-light gasoline separation column 4b, a compressor III 8, a cooling unit II 9, a gas-liquid separation Tank II 7a, a rich gas desulfurizing column 5, a rich gas sweetening column 6, a liquid hydrocarbon desulfurizing column 5a, liquid hydrocarbon sweetening reactor 6a, a cooling unit III 10, a feeding tank 11, an absorption column 12, a demethanizer 13, a deethanizer 14, a depropanizer 15, a propylene rectifying column 16, and an absorbent recovery column 17.

The oil gas feeding pipeline is connected with an inlet of the gas-liquid separation tank I 1. The gas-liquid separation tank 11 is connected at a top thereof sequentially with the compressor I 2 and the light-heavy gasoline separation column 4a, and is connected at a bottom thereof with the light-heavy gasoline separation column 4b.

The light-heavy gasoline separation column 4a is provided at a top thereof with a reflux tank I. The reflux tank I is connected at a top thereof sequentially with the compressor II 3 and the light hydrocarbon-light gasoline separation column 4b, and is connected at a bottom thereof first with a booster pump first and then with the light hydrocarbon-light gasoline separation column 4b. The light-heavy gasoline separation column 4a is provided at a bottom thereof with a heavy gasoline collecting pipeline.

The light hydrocarbon-light gasoline separation column 4b is provided at a top thereof with a reflux tank II. The reflux tank II is connected at a top thereof sequentially with the compressor III 8, the cooling unit II 9, and the gas-liquid separation tank II 7a, and is connected at a bottom thereof first with a booster pump and then with the gas-liquid separation tank II 7a.

The gas-liquid separation tank II 7a is connected at a top thereof with the rich gas desulfurizing column 5, the rich gas sweetening column 6, and the cooling unit III 10, and is connected at a bottom thereof with the liquid hydrocarbon desulfurizing column 5a, the liquid hydrocarbon sweetening reactor 6a, and the cooling unit III 10.

The rich gas desulfurizing column 5 is provided on an upper portion thereof with a lean amine solution feeding pipeline, and the rich gas sweetening column 6 is provided on an upper portion thereof with an alkali liquor feeding pipeline.

The cooling unit III 10 is connected with the feeding tank 11.

The feeding tank 11 is connected at a top thereof with the absorption column, and is connected at a bottom thereof with the demethanizer 15.

The absorption column 12 is connected at a top thereof with the absorbent recovery column 17, is connected at a bottom thereof with the cooling unit III 10, and is provided on an upper portion thereof with a mixed $C_4$ absorbent feeding pipeline.

The demethanizer 15 is connected at a top thereof with the cooling unit III 10, and is connected at a bottom thereof with the deethanizer 14.

The deethanizer 14 is provided at a top thereof with a mixed $C_2$ collecting pipeline optionally provided thereon with an impurity treatment unit, is connected at a bottom thereof with the depropanizer 15, and is provided on an upper portion thereof a propane absorbent collecting pipeline.

The depropanizer 15 is provided on an upper portion thereof with a mixed $C_3$ collecting pipeline optionally connected with the propylene rectifying column 16, and is provided at a bottom thereof with a mixed $C_4$ product collecting pipeline. The mixed $C_4$ product collecting pipeline is divided into two branches, one of which serves as the mixed $C_4$ absorbent feeding pipeline.

The propylene rectifying column 16 is provided at a top thereof with a propylene product collecting pipeline, and is provided at a bottom thereof with a propane product collecting pipeline. The propane product collecting pipeline is divided into two branches, one of which serves as the propane absorbent feeding pipeline.

The absorbent recovery column 17 is provided on a top thereof with a dry gas collecting pipeline, is connected at a bottom thereof with a light-heavy gasoline separation column 4a, and is provided on an upper portion thereof with a heavy gasoline absorbent feeding pipeline. The heavy gasoline collecting pipeline of the light-heavy gasoline separation column 4a is divided into two branches, one of which serves as the heavy gasoline absorbent feeding pipeline.

Figure 8:
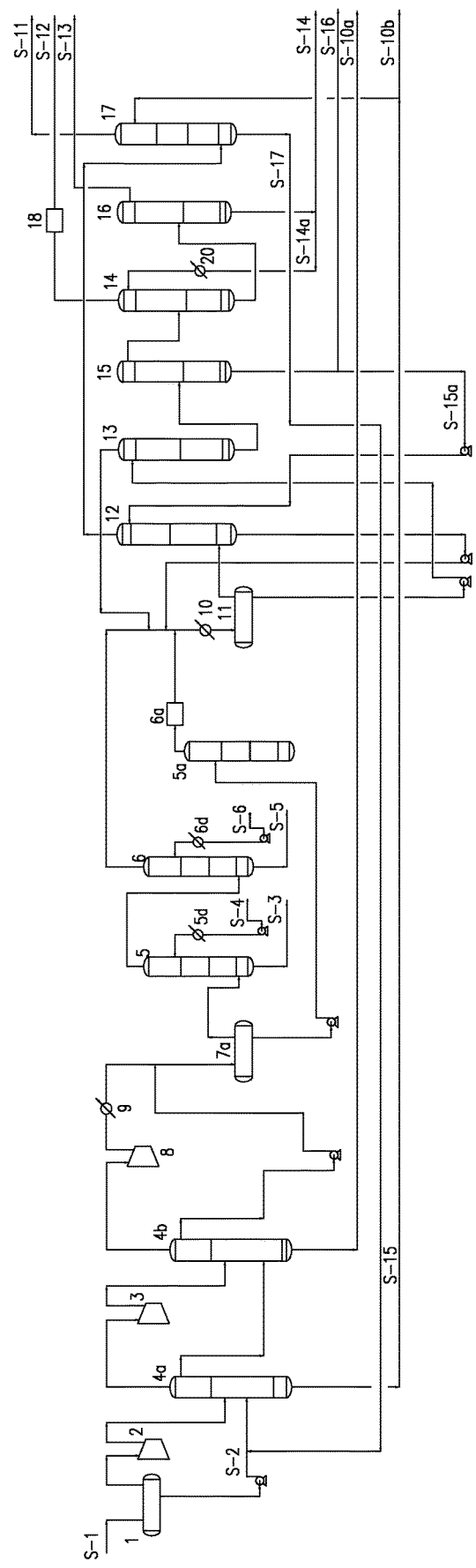
FIG. 8 is a flow diagram of a process of oil gas recovery according to Example 8 of the present invention.

The above device was used for recovery of an oil gas. A process flow of the recovery is shown in FIG. 8.

(1) First gas-liquid separation: an oil gas from an upstream device was condensed and cooled and then sent to the gas-liquid separation tank I 1 for gas-liquid separation. A resulting liquid phase at a bottom of the gas-liquid separation tank 11 was pressurized and then sent to the light-heavy gasoline separation column 4a, and a gas phase at a top of the gas-liquid separation tank I 1 was compressed by a compressor and then sent to the light-heavy gasoline separation column 4a.

(2) Light-heavy gasoline separation: Materials from the gas-liquid separation tank I 1 entered the light-heavy gasoline separation column 4a. A gas phase distilled off at a top of the light-heavy gasoline separation column 4a was condensed and then sent to a reflux tank at the top of the light-heavy gasoline separation column 4a. A resulting gas phase at a top of the reflux tank was compressed and then sent to light hydrocarbon-light gasoline separation column 4b, and a liquid phase at a bottom of the reflux tank was pressurized and then sent to the light hydrocarbon-light gasoline separation column 4b. At least part of a resulting liquid phase at a bottom of the light-heavy gasoline separation column 4a was collected as a heavy gasoline product S-10b. The light-heavy gasoline separation column 4a had an operating temperature of 60-85° C. at the top thereof, and had an operating temperature of 140-190° C. and an operating pressure of 0.25-0.5 MPaG at the bottom thereof. The heavy gasoline had an initial boiling point of 60-85° C.

(3) Light hydrocarbon-light gasoline separation: A stream from the reflux tank at the top of the light-heavy gasoline separation column 4a entered the light hydrocarbon-light gasoline separation column 4b. A gas phase distilled off at a top of the light hydrocarbon-light gasoline separation column 4b was sent to a reflux tank at a top of the light hydrocarbon-light gasoline separation column 4b. A resulting gas phase at the top of the reflux tank was compressed and cooled and then sent to the gas-liquid separation tank II 7a, and a resulting liquid phase at a bottom of the reflux tank was pressurized and then sent to the gas-liquid separation tank II 7a. A resulting liquid phase at a bottom of the light hydrocarbon-light gasoline separation column 4b was collected as a light gasoline product S-10a. The light hydrocarbon-light gasoline separation column 4b had an operating temperature of 55-80° C., and an operating pressure of 1.0-1.35 MPaG. The light gasoline had a dry point of 65-90° C.

(4) Second gas-liquid separation: Materials were mixed to reach gas-liquid equilibrium in the gas-liquid separation tank II 7a, and then subjected to further separation to obtain a gas phase and a liquid phase. The gas phase and the liquid phase were then subjected to impurity removal, respectively. The gas-liquid separation tank II 7a had an operating temperature of 35-45° C., and an operating pressure of 2.3-2.9 MPaG.

(5) Gas phase impurity removal: The gas phase at a top of the gas-liquid separation tank II 7a obtained from the separation in the gas-liquid separation tank II 7a was sequentially subjected to removal of $H_2S$ and $CO_2$ in the rich gas desulfurizing column 5 with a lean amine solution S-4 as an absorbent, and to removal of mercaptans in the rich gas sweetening column 6 with an alkali liquor S-6 as an absorbent, and then sent to the cooling unit. The rich gas desulfurizing column 5 had an operating temperature of 35-45° C., and an operating pressure of 2.2-2.8 MPaG. The rich gas sweetening column 6 had an operating temperature of 35-45° C., and an operating pressure of 2.2-2.8 MPaG.

(6) Liquid phase impurity removal: The liquid phase at a bottom of the gas-liquid separation tank II 7a obtained from the separation in the gas-liquid separation tank II 7a was sequentially subjected to removal of $H_2S$ and $CO_2$ in the liquid hydrocarbon desulfurizing column 5a, and to removal of mercaptans in the liquid hydrocarbon sweetening reactor 6a, and then sent to the cooling unit III 10. The liquid hydrocarbon desulfurizing column 5a had an operating temperature of 35-45° C., and an operating pressure of 3.0-3.5 MPaG.

(7) Cooling: Impurity-removed gaseous light hydrocarbons and impurity-removed liquid light hydrocarbons were mixed and cooled in the cooling unit III 10 and then sent to the feeding tank 11 as a mixed stream.

(8) Feeding: The mixed stream from the cooling unit was mixed and pre-absorbed to reach gas-liquid equilibrium in the feeding tank 11. A resulting gas phase at a top of the feeding tank 11 was sent to the absorption column 12, and a resulting liquid phase at a bottom of the feeding tank 11 was sent to the demethanizer 13. The feeding tank 11 had an operating temperature of 5-25° C., and an operating pressure of 2.2-2.8 MPaG.

(9) Absorption: In the absorption column 12, a mixed $C_4$ was used as an absorbent to absorb $C_2$ and $C_{2+}$ components present in the gas phase from the top of the feeding tank 11, and to simultaneously co-absorb part of methane. A resulting gas phase at a top of the absorption column 12 was sent to the absorbent recovery column 17, and a resulting liquid phase at a bottom of the absorption column 12 was returned to the cooling unit. The absorption column 12 had an operating temperature of 5-25° C., and an operating pressure of 2.1-2.7 MPaG.

(10) Separation:

Demethanization: The liquid phase from the bottom of the feeding tank 11 was subjected to removal of methane and simultaneously to removal of small part of $C_2$ and $C_{2+}$ components in the demethanizer 13. A resulting gas phase at a top of the demethanizer 13 was sent to the cooling unit, and a resulting liquid phase at a bottom of the demethanizer 13 was sent to the deethanizer 14. The demethanizer 13 had an operating temperature of 10-40° C. at the top thereof, and had an operating temperature of 70-90° C. and an operating pressure of 2.3-2.9 MPaG at the bottom thereof.

Deethanization: The liquid phase from the bottom of the demethanizer 13 was subjected to separation in the deethanizer 14 to obtain a $C_2$ component by using the propane product S-14 as an absorbent. A mixed $C_2$ component at a top of the deethanizer 14 obtained from the separation was subjected to impurity removal, and then collected as a mixed $C_2$ product S-12, and resulting liquid-phase components of $C_3$ and $C_{3+}$ at a bottom of the deethanizer 14 were sent to the depropanizer 15. The deethanizer had an operating temperature of 15-30° C. and an operating pressure of 2.6-3.2 MPaG at the top thereof.

Depropanization: The liquid-phase components from the bottom of the deethanizer 14 were subjected to further separation in the depropanizer 15. A $C_3$ component obtained from the separation was sent to the propylene rectifying column 16. At least part of resulting components at a bottom of the depropanizer 15 was sent as a mixed $C_4$ absorbent to the absorption column, and the rest was collected as a mixed $C_4$ product S-16. The depropanizer 15 had an operating temperature of 42-50° C. at the top thereof, and had an operating temperature of 95-120° C. and an operating pressure of 1.6-2.0 MPaG at the bottom thereof.

Propylene rectification: The $C_3$ component from the upper portion of the depropanizer 15 was subjected to further rectification in the propylene rectifying column 16. A resulting gas phase at a top of the propylene rectifying column 16 was cooled and then collected as a propylene product S-13. At least part of a resulting liquid phase at a bottom of the propylene rectifying column 16 was collected as a propane product S-14, and the rest was heated and then sent as a propane absorbent S-14a to the deethanizer 14. The propylene rectifying column 16 had an operating temperature of 45-60° C., and an operating pressure of 1.8-2.0 MPaG.

(11) Recovery of absorbent: In the absorbent recovery column 17, the heavy gasoline product S-10b collected in step (2) was used as an absorbent to absorb $C_4$ and $C_{4+}$ components present in the gas phase from the top of the absorption column 12, and to simultaneously absorb small amounts of $C_2/C_3$ components. A resulting gas phase at a top of the absorbent recovery column 17 was collected as a dry gas S-11, and a resulting liquid phase at a bottom of the absorbent recovery column 17 was returned to the light-heavy gasoline separation column 4a. The absorbent recovery column had an operating temperature of 15-40° C., and an operating pressure of 2.1-2.7 MPaG.

The propane absorbent S-14a collected from the bottom of the propylene rectifying column was sent back to the deethanizer 14 at a flow rate of 6500 kg/h. Composition and flow rates of the recovered products are shown in Table 18 and Table 19.

TABLE 18

| | Dry gas | Mixed $C_2$ | Propylene | Propane | Mixed $C_4$ | Light gasoline | Heavy gasoline |
|---|---|---|---|---|---|---|---|
| Temperature, °C. | 17 | 15 | 46 | 58 | 40 | 40 | 40 |
| Pressure, MPaG | 2.63 | 2.90 | 1.80 | 1.86 | 1.82 | 0.6 | 0.6 |
| Molar vapor fraction | 1 | 1 | 0 | 0 | 0 | 0 | 0 |
| Flow rate, kg/h | 4667 | 6481 | 18487 | 3865 | 28056 | 32387 | 108426 |
| Components | | | Molar fraction | | | | |
| $H_2$ | 0.4964 | | | | | | |
| CO | 0.0083 | | | | | | |
| $CO_2$ | 50 ppmv | 100 ppmv | | | | | |
| $H_2S$ | 10 ppmv | 10 ppmv | 10 ppmv | 10 ppmv | 10 ppmv | | |
| RSH | | 1 ppmv | 20 ppmv | 20 ppmv | 20 ppmv | | |
| $O_2$ | 0.0098 | | | | | | |
| $N_2$ | 0.0757 | | | | | | |
| $CH_4$ | 0.3920 | 0.0089 | | | | | |
| $C_2H_6$ | | 0.4012 | 0.0002 | | | | |
| $C_2H_4$ | 0.0029 | 0.4256 | | | | | |
| $C_3H_6$ | | 0298 ppm | 0.9960 | 0.0100 | 0.0028 | | |
| $C_3H_8$ | | 0.1643 | 0.0038 | 0.9724 | 0.0038 | | |
| i-$C_4H_{10}$ | 0.0003 | | | 0.0131 | 0.4242 | 0.0021 | |
| n-$C_4H_{10}$ | 0.0002 | | | 0.0001 | 0.0886 | 0.0025 | |
| i-$C_4H_8$ | 0.0002 | | | 0.0029 | 0.1697 | 0.0017 | |
| n-$C_4H_8$ | 0.0001 | | | 0.0013 | 0.0938 | 0.0011 | |
| t-$C_4H_8$ | 0.0003 | | | 0.0002 | 0.1281 | 0.0039 | |
| c-$C_4H_8$ | 0.0004 | | | | 0.0889 | 0.0050 | |
| $C_5$+ | 0.0134 | | | | | 0.9837 | 1.000 |
| Total | 1.00 | 1.00 | 1.00 | 1.00 | 1.00 | 1.00 | 1.00 |

TABLE 19

| | Numerical values | |
|---|---|---|
| Items | Light gasoline | Heavy gasoline |
| Density (20° C.), g/cm³ | 0.655 | 0.779 |
| Content of $C_4$ component, vol % | 1.63 | 0 |
| Curve of D86, v % | Temperature, °C. | |
| 0 | 35.2 | 72.5 |
| 5 | 39.3 | 82.6 |
| 10 | 43.5 | 91.6 |
| 30 | 48.5 | 106.5 |
| 50 | 53.6 | 128.9 |
| 70 | 56.9 | 145.6 |
| 90 | 61.3 | 176.9 |
| 95 | 65.6 | 185.3 |
| 100 | 68.3 | 199.8 |

Example 9

Figure 9:
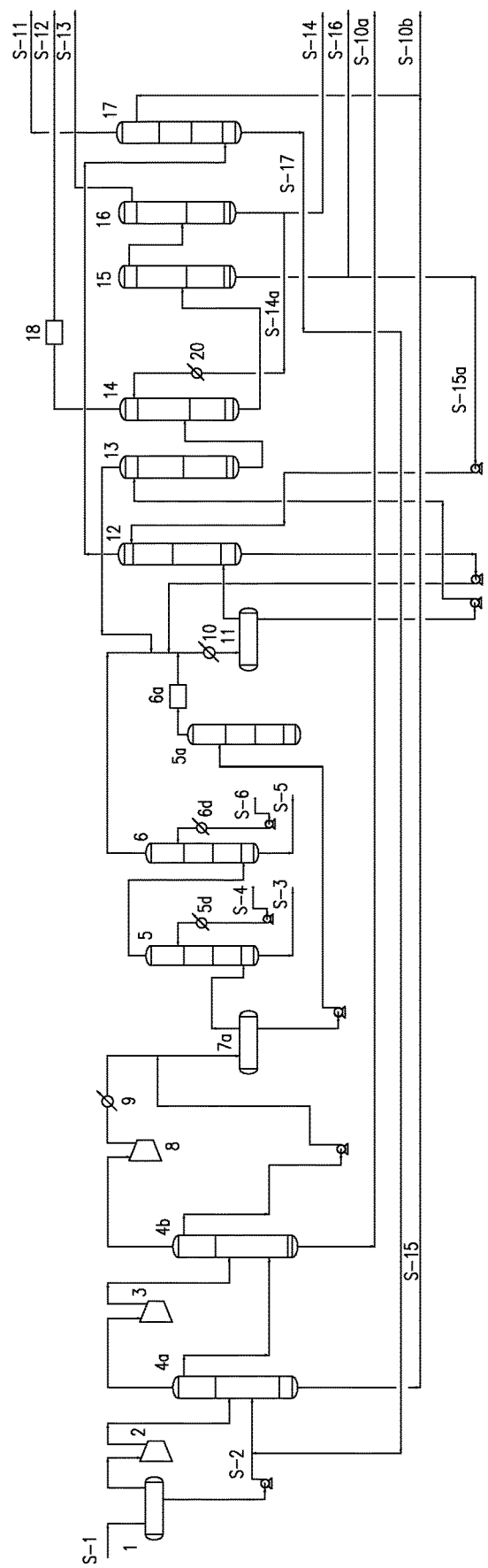
FIG. 9 is a flow diagram of a process of oil gas recovery according to Example 9 of the present invention.

An oil gas was recovered according to a process flow shown in FIG. 9. Example 9 differs from Example 8 in that: in Example 9, part of the circulated propane S-14*a* collected from the bottom of the propylene rectifying column 16 was returned as an absorbent to the deethanizer 14 and used in the deethanizer 14 for separation for the $C_2$ component, so that the mixed $C_2$ product at the top of the deethanizer can has a greatly reduced content of propylene.

The circulated propane S-14*a* collected from the bottom of the propylene rectifying column 16 was returned to the deethanizer 14 at a flow rate of 5000 kg/h. Composition, flow rates, and properties of the recovered products are shown in Table 20 and Table 21.

TABLE 20

| Items | Dry gas | Mixed $C_2$ | Propylene | Propane | Mixed $C_4$ | Light gasoline | Heavy gasoline |
|---|---|---|---|---|---|---|---|
| Temperature, °C. | 17 | 15 | 46 | 58 | 40 | 40 | 40 |
| Pressure, MPaG | 2.63 | 2.90 | 1.80 | 1.86 | 1.82 | 0.6 | 0.6 |
| Molar vapor fraction | 1 | 1 | 0 | 0 | 0 | 0 | 0 |
| Flow rate, kg/h | 4658 | 5968 | 17310 | 4875 | 27349 | 32387 | 108426 |
| Components | | | Molar fraction | | | | |
| $H_2$ | 0.4964 | | | | | | |
| CO | 0.0083 | | | | | | |
| $CO_2$ | 50 ppmv | 100 ppmv | | | | | |
| $H_2S$ | 10 ppmv | 10 ppmv | 10 ppmv | 10 ppmv | 10 ppmv | | |
| RSH | | 1 ppmv | 20 ppmv | 20 ppmv | 20 ppmv | | |
| $O_2$ | 0.0098 | | | | | | |
| $N_2$ | 0.0757 | | | | | | |
| $CH_4$ | 0.392 | 0.0088 | | | | | |

TABLE 20-continued

| Items | Dry gas | Mixed $C_2$ | Propylene | Propane | Mixed $C_4$ | Light gasoline | Heavy gasoline |
|---|---|---|---|---|---|---|---|
| $C_2H_6$ | | 0.4214 | 0.0002 | | | | |
| $C_2H_4$ | 0.0029 | 0.4463 | | | | | |
| $C_3H_6$ | | 550 ppm | 0.996 | 0.01 | 0.0025 | | |
| $C_3H_8$ | | 0.0002 | 0.0038 | 0.9724 | 0.0043 | | |
| i-$C_4H_{10}$ | 0.0003 | 0.0520 | | 0.0131 | 0.4221 | 0.0021 | |
| n-$C_4H_{10}$ | 0.0002 | 0.0120 | | 0.0001 | 0.0875 | 0.0025 | |
| i-$C_4H_8$ | 0.0002 | 0.0209 | | 0.0029 | 0.1689 | 0.0017 | |
| n-$C_4H_8$ | 0.0001 | 0.0116 | | 0.0013 | 0.097 | 0.0011 | |
| t-$C_4H_8$ | 0.0003 | 0.0158 | | 0.0002 | 0.1294 | 0.0039 | |
| c-$C_4H_8$ | 0.0004 | 0.0110 | | 0 | 0.0883 | 0.005 | |
| $C_5+$ | 0.0134 | | | | | 0.9837 | 1 |
| Total | 1.00 | 1.00 | 1.00 | 1.00 | 1.00 | 1.00 | 1.00 |

TABLE 21

| Items | Numerical values | |
|---|---|---|
| | Light gasoline | Heavy gasoline |
| Density (20° C.), g/cm³ | 0.655 | 0.779 |
| Content of $C_4$ component, vol % | 1.63 | 0 |
| Curve of D86, v % | Temperature, ° C. | |
| 0 | 35.2 | 72.5 |
| 5 | 39.3 | 82.6 |
| 10 | 43.5 | 91.6 |
| 30 | 48.5 | 106.5 |
| 50 | 53.6 | 128.9 |
| 70 | 56.9 | 145.6 |
| 90 | 61.3 | 176.9 |
| 95 | 65.6 | 185.3 |
| 100 | 68.3 | 199.8 |

Example 10

Figure 10:
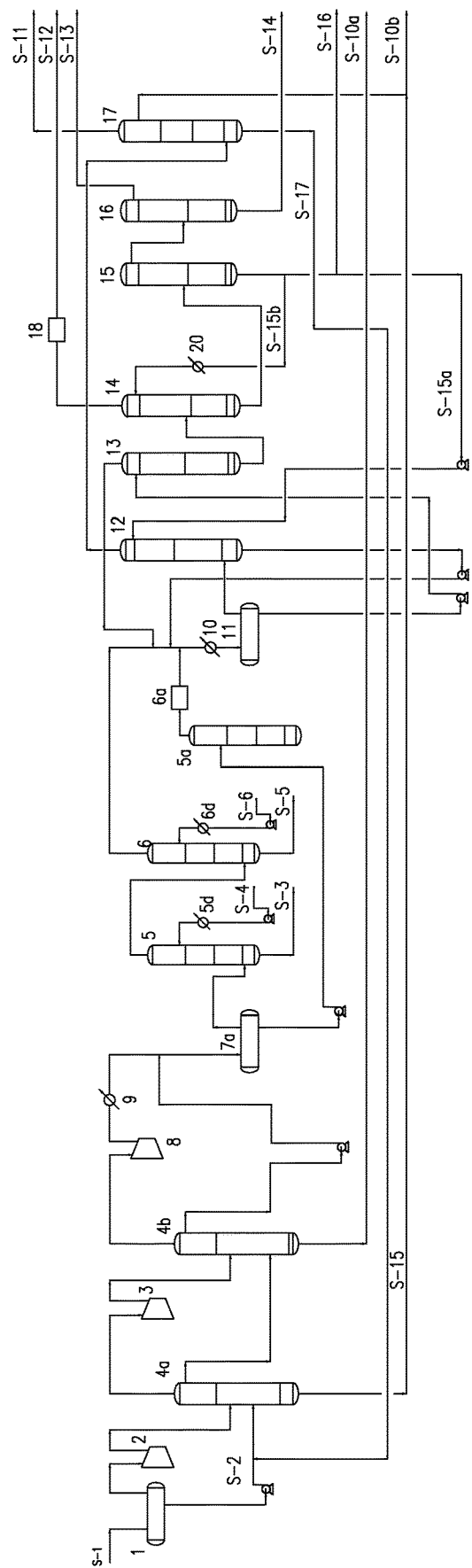
FIG. 10 is a flow diagram of a process of oil gas recovery according to Example 10 of the present invention.

An oil gas was recovered according to a process flow shown in FIG. 10. Example 10 differs from Example 9 in that: in Example 10, demethanization, depropanization, and deethanization were used in sequence to conduct the separation for light hydrocarbons. Part of propane collected from the bottom of the propylene rectifying column 16 was used as an absorbent S-15b at the top of the deethanizer 14 to perform the separation for the $C_2$ component, so that the mixed $C_2$ product at the top of the deethanizer can have a greatly reduced content of propylene.

The propane absorbent S-15b collected from the bottom of the propylene rectifying column 16 was returned to the deethanizer 14 at a flow rate of 6500 kg/h. Composition, flow rates, and properties of the recovered products are shown in Table 22 and Table 23.

TABLE 22

| Items | Dry gas | Mixed $C_2$ | Propylene | Propane | Mixed $C_4$ | Light gasoline | Heavy gasoline |
|---|---|---|---|---|---|---|---|
| Temperature, ° C. | 17 | 15 | 46 | 58 | 40 | 40 | 40 |
| Pressure, MPaG | 2.63 | 2.90 | 1.80 | 1.86 | 1.82 | 0.6 | 0.6 |
| Molar vapor fraction | 1 | 1 | 0 | 0 | 0 | 0 | 0 |
| Flow rate, kg/h | 4667 | 6481 | 18494 | 3849 | 28079 | 32387 | 108426 |
| Components | | | Molar fraction | | | | |
| $H_2$ | 0.4964 | | | | | | |
| CO | 0.0083 | | | | | | |
| $CO_2$ | 50 ppmv | 100 ppmv | | | | | |
| $H_2S$ | 10 ppmv | 10 ppmv | 10 ppmv | 10 ppmv | 10 ppmv | | |
| RSH | | 1 ppmv | 20 ppmv | 20 ppmv | 20 ppmv | | |
| $O_2$ | 0.0098 | | | | | | |
| $N_2$ | 0.0757 | | | | | | |
| $CH_4$ | 0.3920 | 0.0089 | | | | | |
| $C_2H_6$ | | 0.4012 | 0.0002 | | | | |
| $C_2H_4$ | 0.0029 | 0.4256 | | | | | |
| $C_3H_6$ | | 298 ppm | 0.9960 | 0.0100 | 0.0029 | | |
| $C_3H_8$ | | 0.1643 | 0.0038 | 0.9724 | 0.0037 | | |
| i-$C_4H_{10}$ | 0.0003 | | | 0.0131 | 0.4242 | 0.0021 | |
| n-$C_4H_{10}$ | 0.0002 | | | 0.0001 | 0.0886 | 0.0025 | |
| i-$C_4H_8$ | 0.0002 | | | 0.0029 | 0.1697 | 0.0017 | |
| n-$C_4H_8$ | 0.0001 | | | 0.0013 | 0.0938 | 0.0011 | |
| t-$C_4H_8$ | 0.0003 | | | 0.0002 | 0.1281 | 0.0039 | |
| c-$C_4H_8$ | 0.0004 | | | | 0.0889 | 0.0050 | |
| $C_5+$ | 0.0134 | | | | | 0.9837 | 1.000 |
| Total | 1.00 | 1.00 | 1.00 | 1.00 | 1.00 | 1.00 | 1.00 |

TABLE 23

| Items | Numerical values | |
|---|---|---|
| | Light gasoline | Heavy gasoline |
| Density (20° C.), g/cm³ | 0.655 | 0.779 |
| Content of C₄ component, vol % | 1.63 | 0 |
| Curve of D86, v % | Temperature, ° C. | |
| 0 | 35.2 | 72.5 |
| 5 | 39.3 | 82.6 |
| 10 | 43.5 | 91.6 |
| 30 | 48.5 | 106.5 |
| 50 | 53.6 | 128.9 |
| 70 | 56.9 | 145.6 |
| 90 | 61.3 | 176.9 |
| 95 | 65.6 | 185.3 |
| 100 | 68.3 | 199.8 |

It can be seen from the data in the above tables that the present invention is simple in its process and is operated at moderate conditions, and consumes less energy. The present invention can realize separation for and recovery of light gasoline and heavy gasoline in the oil gas with relatively few devices, and in particular realize high-efficiency recovery of components such as $C_2$ and propylene at subcooled conditions. The recovered $C_2$ contains basically no propylene, and a second separation between $C_2$ and various other components is not needed. Meanwhile, the present invention ensures a total recovery rate of the $C_2$ component of more than 98 wt %, and a recovery rate of propylene of more than 99 wt %. The recovered $C_2$ has a content of methane of not more than 1 vol %, and a content of ethane of not more than 2000 ppmv. Besides, the recovered dry gas contains relatively small amounts of impurities and has a content of $C_2$ and $C_{2+}$ components of not more than 2 vol %, and the purity of hydrogen is more than 40 mol %.

Comparative Example 1

This comparative example is provided for a comparison with Example 5, so as to illustrate the effects of separating out gasoline components before impurity removal in the present invention on impurity removal. The main difference between Comparative Example 1 and Example 5 is that: in Comparative Example 1, the gas phase and the liquid phase were subjected to impurity removal, respectively, and then subjected to separation for gasoline.

Figure 11:
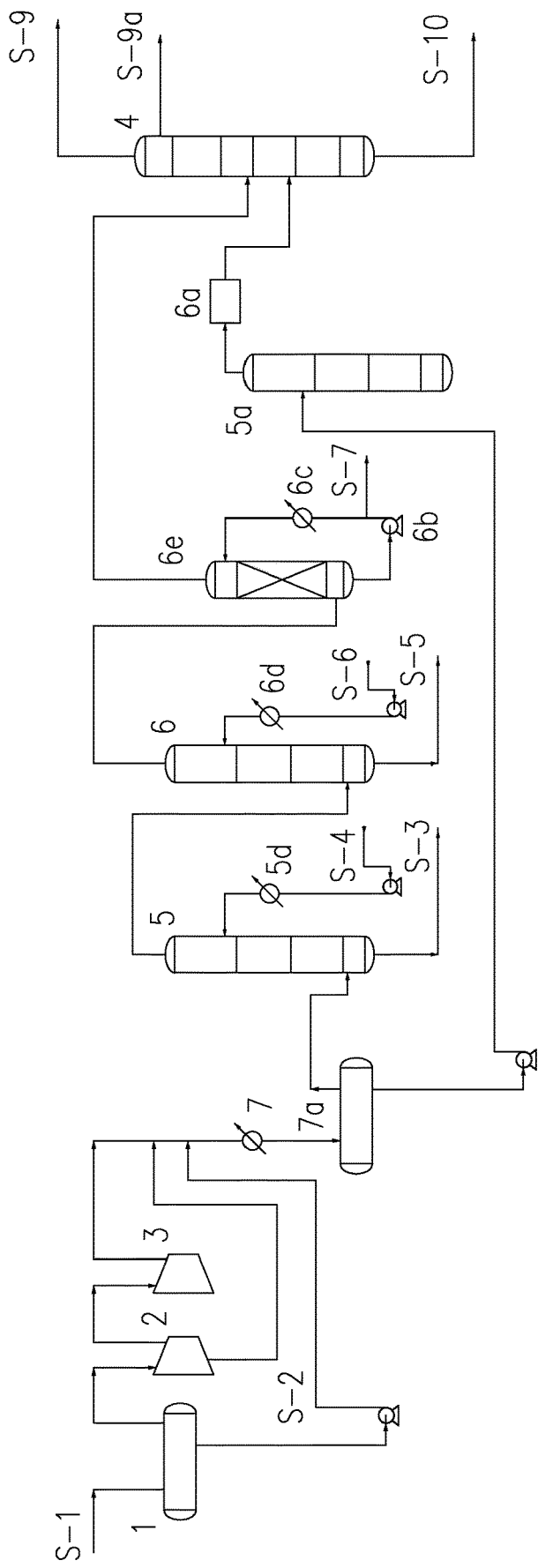
FIG. 11 is a flow diagram of a process of oil gas recovery according to Comparative Example 1 of the present invention.

A process flow of Comparative Example 1 is shown in FIG. 11.

(1) Gas-liquid separation: an oil gas S-1 from an upstream device was condensed and cooled and sent to a gas-liquid separation tank I 1 for gas-liquid separation. A resulting liquid phase at a bottom of the gas-liquid separation tank 11 was pressurized and then sent to a cooling unit, and a resulting gas phase at a top of the gas-liquid separation tank 11 was compressed by a compressor and then sent to the cooling unit. A liquid phase between stages of the compressor was sent to the cooling unit.

(2) Cooling and gas-liquid separation: One gas phase and two liquid phases from step (1) entered a gas-liquid separation tank II 7a. A gas phase separated out at a top of the gas-liquid separation tank II 7a entered into a downstream gas phase impurity removal device, and a liquid phase separated out at a bottom of the gas-liquid separation tank II 7a was pressurized and then sent to the downstream liquid phase impurity removal device.

(3) Gas phase impurity removal: The gas phase separated out at the top of the gas-liquid separation tank II 7a was sequentially subjected to removal of $H_2S$ and $CO_2$ in a rich gas desulfurizing column 5 with a lean amine solution S-4 as an absorbent, to removal of mercaptans in a rich gas sweetening column 6 with an alkali liquor S-6 as an absorbent, and then sent to a rich gas water washing tank 6e for water washing and then sent to a debutanizer 4. The rich gas desulfurizing column 5 had an operating temperature of 35-45° C., and an operating pressure of 1.0-1.3 MPaG. The rich gas sweetening column 6 had an operating temperature of 35-45° C., and an operating pressure of 0.9-1.2 MPaG.

(4) Liquid phase impurity removal: The liquid phase separated out at the bottom of the gas-liquid separation tank II 7a was sequentially subjected to removal of $H_2S$ and $CO_2$ in a liquid hydrocarbon desulfurizing column 5a, to removal of mercaptans in a liquid hydrocarbon sweetening reactor 6a, and then sent to the debutanizer 4. The liquid hydrocarbon desulfurizing column 5a had an operating temperature of 35-45° C., and an operating pressure of 1.5-2.0 MPaG.

(5) Debutanization: The gas phase and the liquid phase from step (1) entered into the debutanizer 4. A gas phase distilled off from a top of the debutanizer 4 was condensed and then sent a reflux tank at the top of the debutanizer 4 for separation to obtain a rich gas and liquid hydrocarbons. At least part of a resulting liquid phase at a bottom of the debutanizer 4 was collected as a stable gasoline product S-10. The debutanizer had an operating temperature of 45-65° C. and an operating pressure of 0.9-1.2 MPaG at the top thereof, and had an operating temperature of 150-200° C. at the bottom thereof. The reflux tank had an operating temperature of 35-50° C.

The above method was used to perform impurity removal on the rich gas. Properties of the rich gas after the impurity removal are shown in Table 24.

TABLE 24

| Categories | Rich gas | | Liquid hydrocarbons | |
|---|---|---|---|---|
| | Before desulfuration and sweetening | After desulfuration and sweetening | Before desulfuration and sweetening | After desulfuration and sweetening |
| CO₂ | 8653 ppmv | 150 ppmv | 1371 ppmv | 230 ppmv |
| H₂S | 1560 ppmv | 17 ppmv | 787 ppmv | 18 ppmv |
| RSH | 340 ppmv | 87 ppmw | 450 ppmv | 120 ppmw |

As can be seen from the above table, the effects of desulfurization of the rich gas and the liquid hydrocarbons in Comparative Example 1 are not as good as those of the desulfurization in Example 2, and the rich gas and the liquid hydrocarbons contain a large amounts of gasoline components, which brings the following adverse effects. First, the gasoline components will disperse to the rich gas and the liquid hydrocarbons, resulting in a higher content of mercaptans in the rich gas and the liquid hydrocarbons. Second, due to the relatively large mercaptan molecules in gasoline and the difficulty to remove such large molecular mercaptans, effects of desulfurization and sweetening of the rich gas and the liquid hydrocarbons can be affected. Third, the presence of gasoline in the liquid hydrocarbons may cause stratification of the amine solution and the liquid hydrocarbons when the liquid hydrocarbons are desulfurized, which affects effects of the desulfurization.

It shall be noted that the above-described examples are only used to explain the present invention, and do not constitute any limitation to the present invention. Although the present invention has been described with reference to typical examples, it shall be appreciated that the terms used herein are descriptive and explanatory, rather than restrictive. The present invention can be amended within the scope of the claims of the present invention as required, and can be modified without departing from the scope and spirit of the present invention. Although the present invention described herein relates to specific methods, materials, and examples, it does not mean that the present invention is limited to the specific examples disclosed herein. On the contrary, the present invention can be extended to all other methods and applications having the same functions.

The invention claimed is:

1. A method for treating an oil gas, comprising the following steps:
    (1) subjecting a hydrocarbon material to a first gas-liquid separation to obtain a first gas-phase material mainly containing $H_2$ and C1-C4 and a first liquid-phase material mainly containing C5+; and
    (2) subjecting the first gas-phase material to impurity removal to obtain an impurity-removed first gas-phase material, subjecting the impurity-removed first gas-phase material to a second gas-liquid separation to obtain a second gas-phase material mainly containing $H_2$ and C1-C2 and a second liquid-phase material mainly containing C3-C4; subjecting the second gas-phase material to gas phase impurity removal to obtain an impurity-removed second gas-phase material, and subjecting the second liquid-phase material to liquid phase impurity removal to obtain an impurity-removed second liquid-phase material; the impurity-removed second gas-phase material and the impurity-removed second liquid-phase material being mixed and then subjected to a separation treatment to obtain a dry gas product mainly containing $H_2$ and C1, a $C_2$ product mainly containing C2, a C3 product mainly containing C3, and a C4 product mainly containing C4.

2. The method for treating an oil gas according to claim 1, wherein in step (2), the impurity removal is used to remove an acidic substance and a mercaptan, the acidic substance being specifically hydrogen sulfide and/or carbon dioxide.

3. The method for treating an oil gas according to claim 1, wherein in step (2),
    the impurity removal comprises treating the first gas-phase material sequentially by amine washing and/or alkali washing and/or water washing.

4. The method for treating an oil gas according to claim 1, wherein in step (2),
    the gas phase impurity removal includes treating the second gas-phase material sequentially by gas phase amine washing and/or gas phase alkali washing and/or gas phase water washing, and the liquid phase impurity removal comprises treating the second liquid-phase material sequentially by liquid phase amine washing and/or liquid phase alkali washing and/or liquid phase water washing.

5. The method for treating an oil gas according to claim 1, wherein in step (2), the separation treatment specifically comprises the following steps:
    (a) cooling an impurity-removed first gas-phase material or a mixture material of an impurity-removed second gas-phase material and an impurity-removed second liquid-phase material, and then subjecting the cooled impurity-removed first gas-phase material or the cooled mixture material of the impurity-removed second gas-phase material and the impurity-removed second liquid-phase material to first separation, to obtain a gas-phase material mainly containing $H_2$ and C1 and a liquid-phase material mainly containing C1-C4;
    (b) subjecting the liquid-phase material mainly containing C1-C4 to second separation to obtain a gas-phase material mainly containing C1 and a liquid-phase material mainly containing C2-C4;
    (c) subjecting the liquid-phase material mainly containing C2-C4 to third separation to obtain the C2 product mainly containing C2 and a liquid-phase material mainly containing C3-C4 or obtain the C3 product mainly containing C3 and a liquid-phase material mainly containing C2 and C4;
    (d) subjecting the liquid-phase material mainly containing C3-C4 or the liquid-phase material mainly containing C2 and C4 to fourth separation to obtain the C4 product mainly containing C4 and the C3 product mainly containing C3 or the C2 product mainly containing C2; and
    (e) subjecting the C3 product to rectification to obtain a propane product mainly containing propane and a propylene product mainly containing propylene.

6. The method for treating an oil gas according to claim 5, wherein in step (a), the gas-phase material mainly containing $H_2$ and C1 is treated with an absorbent to obtain the dry gas product containing $H_2$ and C1 and a liquid-phase material mainly containing the absorbent; the absorbent is a mixture of C4/C5; the liquid-phase material mainly containing the absorbent is recycled to step (d).

7. The method for treating an oil gas according to claim 5, wherein the gas-phase material mainly containing C1 is recycled to step (a); in step (a), the cooling is conducted one or more times, and the gas-phase material mainly containing C1 is recycled to a first cooling step.

8. The method for treating an oil gas according to claim 1, wherein the hydrocarbon material is derived from a top of a fluid catalytic cracking fractionator, a top of a deep catalytic cracking fractionator, a top of a catalytic pyrolysis fractionator, a top of a delayed coking fractionator or a top of a flexicoking fractionator; the hydrocarbon material is a condensed and cooled material; the condensed and cooled material has a temperature of 30-60° C. and a pressure of 0.01-0.3 MPaG.

9. The method for treating an oil gas according to claim 1, wherein:
    in step (1), the first gas-liquid separation is selected from mode I and mode II, wherein the mode I is to directly separate the hydrocarbon material into the first gas-phase material mainly containing $H_2$ and C1-C4 and the first liquid-phase material mainly containing C5+, and the mode II is to first separate the hydrocarbon material into a gas-phase material mainly containing $H_2$, light hydrocarbons and light gasoline, and a liquid-phase material mainly containing heavy gasoline, and then separate the gas-phase material mainly containing $H_2$, light hydrocarbons and light gasoline into the first gas-phase material mainly containing $H_2$ and C1-C4 and the first liquid-phase material mainly containing C5+.

10. The method for treating an oil gas according to claim 5, wherein:
- in step (a), the first separation is performed at conditions comprising: a temperature of 5-25° C., a pressure of 2.0-3.5 MPaG; and/or,
- in step (b), the second separation is performed in a demethanizer, wherein the demethanizer has a temperature at a top thereof of 10-40° C., a temperature at a bottom thereof of 70-95° C., and an internal pressure of 2.3-2.9 MPaG; and/or,
- in step (c), when it is intended to obtain the C2 product mainly containing C2 and the liquid-phase material mainly containing C3-C4, the third separation is performed in a deethanizer, the deethanizer having a temperature at a top thereof of −20-30° C., a temperature at a bottom thereof of 50-110° C., and an internal pressure of 2.2-3.8 M PaG; when it is intended to obtain the C3 product mainly containing C3 and the liquid-phase material mainly containing C2 and C4, the third separation is performed in a depropanizer, the depropanizer having a temperature at a top thereof of 20-60° C., a temperature at a bottom thereof of 70-120° C., and an internal pressure of 1.2-2.5 MPaG; and/or,
- in step (d), when it is intended to obtain the C4 product mainly containing C4 and the C3 product mainly containing C3, the fourth separation is performed in a depropanizer, the depropanizer having a temperature at a top thereof of 20-60° C., a temperature at a bottom thereof of 70-120° C., and an internal pressure of 1.2-2.5 MPaG; when it is intended to obtain the C44 product mainly containing C4 and the C2 product mainly containing C2, the fourth separation is performed in a deethanizer, the deethanizer having a temperature at a top thereof of −20-30° C., a temperature at a bottom thereof of 50-110° C., and an internal pressure of 2.2-3.8 MPaG; and/or,
- in step (e), the rectification is performed at conditions comprising: a temperature of 45-65° C., and a pressure of 1.8-2.0 MPaG.

11. The method for treating an oil gas according to claim 6, wherein the gas-phase material mainly containing $H_2$ and C1 is treated with the absorbent at conditions comprising: a temperature of 5-25° C., a pressure of 2.0-3.5 MPaG.

12. The method for treating an oil gas according to claim 9, wherein the mode I is performed in a debutanizer, and the mode II is performed in a light-heavy gasoline separation column and a light hydrocarbon-light gasoline separation column; and/or
- the debutanizer has an operating temperature at a top thereof of 40-70° C., and/or an operating temperature at a bottom thereof of 180-220° C., and/or an internal operating pressure of 1.0-1.6 MPa G; and/or,
- the light-heavy gasoline separation column has an operating temperature at a top thereof of 60-85° C., and/or an operating temperature at a bottom thereof of 140-190° C., and/or an internal operating pressure 0.25-0.5 MPaG; and/or,
- the light hydrocarbon-light gasoline separation column has an operating temperature of 55-90° C., and/or an internal operating pressure of 1.0-1.35 MPaG.

13. The method for treating an oil gas according to claim 10, wherein in step (a), the first separation is performed in a feeding tank; and/or,
- in step (e), the rectification is performed in a rectifying column.

* * * * *

UNITED STATES PATENT AND TRADEMARK OFFICE
CERTIFICATE OF CORRECTION

PATENT NO. : 11,946,002 B2
APPLICATION NO. : 17/281980
DATED : April 2, 2024
INVENTOR(S) : Mengqi Huang et al.

Page 1 of 1

It is certified that error appears in the above-identified patent and that said Letters Patent is hereby corrected as shown below:

In the Claims
Column 69, Line 30, "when it is intended to obtain the C44" should read "when it is intended to obtain the C4"

Signed and Sealed this
Eleventh Day of June, 2024

Katherine Kelly Vidal
*Director of the United States Patent and Trademark Office*